United States Patent
Pollack et al.

(10) Patent No.: US 10,842,230 B2
(45) Date of Patent: Nov. 24, 2020

(54) REEL BASED CLOSURE SYSTEM

(71) Applicant: Boa Technology Inc., Denver, CO (US)

(72) Inventors: Thomas Pollack, Golden, CO (US);
Eric Whewell, Denver, CO (US);
Randon Kruse, Denver, CO (US);
Mark Clementi, Denver, CO (US);
Josef Duller, Louisville, CO (US);
Brendan Hoskens, Denver, CO (US);
David Roland, Golden, CO (US);
Mark Soderberg, Conifer, CO (US)

(73) Assignee: Boa Technology Inc., Denver, CO (US)

( * ) Notice: Subject to any disclaimer, the term of this patent is extended or adjusted under 35 U.S.C. 154(b) by 195 days.

(21) Appl. No.: 15/836,475

(22) Filed: Dec. 8, 2017

(65) Prior Publication Data

US 2018/0160775 A1 Jun. 14, 2018

Related U.S. Application Data

(60) Provisional application No. 62/432,175, filed on Dec. 9, 2016, provisional application No. 62/438,288, filed on Dec. 22, 2016.

(51) Int. Cl.
*A43C 11/16* (2006.01)
*A43C 11/14* (2006.01)
(Continued)

(52) U.S. Cl.
CPC .............. *A43C 11/165* (2013.01); *A43C 7/00* (2013.01); *A43C 11/20* (2013.01);
(Continued)

(58) Field of Classification Search
CPC ......... A43C 11/165; A43C 7/00; A43C 11/20; A43C 11/1493; F16G 11/046;
(Continued)

(56) References Cited

U.S. PATENT DOCUMENTS

| 59,332 A | 10/1866 | White et al. |
| 80,834 A | 8/1868 | Prussia |

(Continued)

FOREIGN PATENT DOCUMENTS

| CA | 2112789 | 8/1994 |
| CA | 2114387 | 8/1994 |

(Continued)

OTHER PUBLICATIONS

Invitation to Pay Additional Fees and Communication Relating to the Results of the Partial International Search Report for PCT/US2017/065355 dated Mar. 23, 2018, 19 pages.

(Continued)

*Primary Examiner* — Robert Sandy
*Assistant Examiner* — Louis A Mercado
(74) *Attorney, Agent, or Firm* — Kilpatrick Townsend & Stockton, LLP

(57) ABSTRACT

A reel based closure device includes a housing, a tension member, a spool that is rotatably positioned within the housing, and a tightening component that is positioned axially above the spool and that is operably coupled therewith so that an operation of the tightening component causes the spool to rotate within the housing to wind the tension member about the spool. The reel based closure device also includes a coupling component that is separate from the tension member and that frictionally engages with a distal end of the tension member so that the coupling component is removably fixed to the tension member. The spool component includes a coupling feature within which the coupling component is positioned to attach the tension member to the spool.

20 Claims, 41 Drawing Sheets

(51) Int. Cl.
  *A43C 11/20* (2006.01)
  *B65H 75/44* (2006.01)
  *A43C 7/00* (2006.01)
  *F16G 11/04* (2006.01)
  *F16G 11/12* (2006.01)
  *A61F 5/01* (2006.01)

(52) U.S. Cl.
  CPC ..... *B65H 75/4449* (2013.01); *B65H 75/4492* (2013.01); *F16G 11/046* (2013.01); *F16G 11/12* (2013.01); *A43C 11/1493* (2013.01); *A61F 5/01* (2013.01)

(58) Field of Classification Search
  CPC ....... F16G 11/12; A61F 5/01; B65H 75/4449; B65H 75/4492
  See application file for complete search history.

(56) References Cited

U.S. PATENT DOCUMENTS

| | | |
|---|---|---|
| 117,530 A | 8/1871 | Foote |
| 228,946 A | 6/1880 | Schulz |
| 230,759 A | 8/1880 | Drummond |
| 379,113 A | 3/1888 | Hibberd |
| 746,563 A | 12/1903 | McMahon |
| 819,993 A | 5/1906 | Haws et al. |
| 908,704 A | 1/1909 | Sprinkle |
| 1,060,422 A | 4/1913 | Bowdish |
| 1,062,511 A | 5/1913 | Short |
| 1,083,775 A | 1/1914 | Thomas |
| 1,090,438 A | 3/1914 | Worth et al. |
| 1,170,472 A | 2/1916 | Barber |
| 1,288,859 A | 12/1918 | Feller et al. |
| 1,390,991 A | 9/1921 | Fotchuk |
| 1,393,188 A | 10/1921 | Whiteman |
| 1,412,486 A | 4/1922 | Paine |
| 1,416,203 A | 5/1922 | Hobson |
| 1,429,657 A | 9/1922 | Trawinski |
| 1,466,673 A | 9/1923 | Solomon et al. |
| 1,469,661 A | 10/1923 | Migita |
| 1,481,903 A | 1/1924 | Hart |
| 1,502,919 A | 7/1924 | Seib |
| 1,530,713 A | 3/1925 | Clark |
| 1,862,047 A | 6/1932 | Boulet et al. |
| 1,995,243 A | 3/1935 | Clarke |
| 2,088,851 A | 8/1937 | Gantenbein |
| 2,109,751 A | 3/1938 | Matthias et al. |
| 2,124,310 A | 7/1938 | Murr, Jr. |
| 2,316,102 A | 4/1943 | Preston |
| 2,539,026 A | 1/1951 | Mangold |
| 2,611,940 A | 9/1952 | Cairns |
| 2,673,381 A | 3/1954 | Dueker |
| 2,907,086 A | 10/1959 | Ord |
| 2,926,406 A | 3/1960 | Zahnor |
| 2,991,523 A | 7/1961 | Del Conte |
| 3,028,602 A | 4/1962 | Miller |
| 3,035,319 A | 5/1962 | Wolff |
| 3,106,003 A | 10/1963 | Herdman |
| 3,112,545 A | 12/1963 | Williams |
| 3,122,810 A | 3/1964 | Lawrence et al. |
| 3,163,900 A | 1/1965 | Martin |
| D200,394 S | 2/1965 | Hakim |
| 3,169,325 A | 2/1965 | Fesl |
| 3,193,950 A | 7/1965 | Liou |
| 3,197,155 A | 7/1965 | Chow |
| 3,214,809 A | 11/1965 | Zahnor |
| 3,221,384 A | 12/1965 | Aufenacker |
| 3,276,090 A | 10/1966 | Nigon |
| D206,146 S | 11/1966 | Hendershot |
| 3,345,707 A | 10/1967 | Rita |
| D210,649 S | 4/1968 | Getgay |
| 3,401,437 A | 9/1968 | Christpohersen |
| 3,430,303 A | 3/1969 | Perrin et al. |
| 3,491,465 A | 1/1970 | Martin |
| 3,545,106 A | 12/1970 | Martin |
| 3,618,232 A | 11/1971 | Shnuriwsky |
| 3,668,791 A | 6/1972 | Salzman et al. |
| 3,678,539 A | 7/1972 | Graup |
| 3,703,775 A | 11/1972 | Gatti |
| 3,729,779 A | 5/1973 | Porth |
| 3,738,027 A | 6/1973 | Schoch |
| 3,793,749 A | 2/1974 | Gertsch et al. |
| 3,808,644 A | 5/1974 | Schoch |
| 3,934,346 A | 1/1976 | Sasaki et al. |
| 3,975,838 A | 8/1976 | Martin |
| 4,084,267 A | 4/1978 | Zadina |
| 4,130,949 A | 12/1978 | Seidel |
| 4,142,307 A | 3/1979 | Martin |
| 4,227,322 A | 10/1980 | Annovi |
| 4,261,081 A | 4/1981 | Lott |
| 4,267,622 A | 5/1981 | Burnett-Johnston |
| 4,408,403 A | 10/1983 | Martin |
| 4,417,703 A | 11/1983 | Weinhold |
| 4,433,456 A | 2/1984 | Baggio |
| 4,452,405 A | 6/1984 | Adomeit |
| 4,463,761 A | 8/1984 | Pols et al. |
| 4,480,395 A | 11/1984 | Schoch |
| 4,507,878 A | 4/1985 | Semouha |
| 4,516,576 A | 5/1985 | Kirchner |
| 4,551,932 A | 11/1985 | Schoch |
| 4,555,830 A | 12/1985 | Petrini et al. |
| 4,574,500 A | 3/1986 | Aldinio et al. |
| 4,616,432 A | 10/1986 | Bunch et al. |
| 4,616,524 A | 10/1986 | Biodia |
| 4,619,057 A | 10/1986 | Sartor et al. |
| 4,620,378 A | 11/1986 | Sartor |
| 4,631,839 A | 12/1986 | Bonetti et al. |
| 4,631,840 A | 12/1986 | Gamm |
| 4,633,599 A | 1/1987 | Morell et al. |
| 4,644,938 A | 2/1987 | Yates et al. |
| 4,654,985 A | 4/1987 | Chalmers |
| 4,660,300 A | 4/1987 | Morell et al. |
| 4,660,302 A | 4/1987 | Arieh et al. |
| 4,680,878 A | 7/1987 | Pozzobon et al. |
| 4,719,670 A | 1/1988 | Kurt |
| 4,719,709 A | 1/1988 | Vaccari |
| 4,719,710 A | 1/1988 | Pozzobon |
| 4,722,477 A | 2/1988 | Floyd |
| 4,741,115 A | 5/1988 | Pozzobon |
| 4,748,726 A | 6/1988 | Schoch |
| 4,760,653 A | 8/1988 | Baggio |
| 4,780,969 A | 11/1988 | White, Jr. |
| 4,787,124 A | 11/1988 | Pozzobon et al. |
| 4,790,081 A | 12/1988 | Benoit et al. |
| 4,796,829 A | 1/1989 | Pozzobon et al. |
| 4,799,297 A | 1/1989 | Baggio et al. |
| 4,802,291 A | 2/1989 | Sartor |
| 4,811,503 A | 3/1989 | Iwama |
| 4,826,098 A | 5/1989 | Pozzobon et al. |
| 4,841,649 A | 6/1989 | Baggio et al. |
| 4,856,207 A | 8/1989 | Datson |
| 4,862,878 A | 9/1989 | Davison |
| 4,870,723 A | 10/1989 | Pozzobon et al. |
| 4,870,761 A | 10/1989 | Tracy |
| 4,884,760 A | 12/1989 | Baggio et al. |
| 4,901,938 A | 2/1990 | Cantley et al. |
| 4,924,605 A | 5/1990 | Spademan |
| D308,282 S | 6/1990 | Bergman et al. |
| 4,937,953 A | 7/1990 | Walkhoff |
| 4,961,544 A | 10/1990 | Biodia |
| 4,979,953 A | 12/1990 | Spence |
| 4,989,805 A | 2/1991 | Burke |
| 5,001,817 A | 3/1991 | De Bortoli et al. |
| 5,016,327 A | 5/1991 | Klausner |
| 5,042,177 A | 8/1991 | Schoch |
| 5,062,225 A | 11/1991 | Gorza |
| 5,065,480 A | 11/1991 | DeBortoli |
| 5,065,481 A | 11/1991 | Walkhoff |
| 5,108,216 A | 4/1992 | Geyer et al. |
| 5,117,567 A | 6/1992 | Berger |
| 5,152,038 A | 10/1992 | Schoch |
| 5,157,813 A | 10/1992 | Carroll |
| 5,158,428 A | 10/1992 | Gessner et al. |

(56) References Cited

U.S. PATENT DOCUMENTS

| | | |
|---|---|---|
| 5,177,882 A | 1/1993 | Berger |
| 5,181,331 A | 1/1993 | Berger |
| 5,184,378 A | 2/1993 | Batra |
| D333,552 S | 3/1993 | Berger et al. |
| 5,205,055 A | 4/1993 | Harrell |
| 5,233,767 A | 8/1993 | Kramer |
| 5,249,377 A | 10/1993 | Walkhoff |
| 5,259,094 A | 11/1993 | Zepeda |
| 5,315,741 A | 5/1994 | Debberke |
| 5,319,868 A | 6/1994 | Hallenbeck |
| 5,319,869 A | 6/1994 | McDonald et al. |
| 5,325,613 A | 7/1994 | Sussmann |
| 5,327,662 A | 7/1994 | Hallenbeck |
| 5,335,401 A | 8/1994 | Hanson |
| 5,341,583 A | 8/1994 | Hallenbeck |
| 5,345,697 A | 9/1994 | Quellais |
| 5,355,596 A | 10/1994 | Sussmann |
| 5,357,654 A | 10/1994 | Hsing-Chi |
| 5,371,957 A | 12/1994 | Gaudio |
| 5,381,609 A | 1/1995 | Hieblinger |
| 5,392,535 A | 2/1995 | Van Noy et al. |
| D357,576 S | 4/1995 | Steinweis |
| 5,425,161 A | 6/1995 | Schoch |
| 5,425,185 A | 6/1995 | Gansler |
| 5,430,960 A | 7/1995 | Richardson |
| 5,433,648 A | 7/1995 | Fryd Man |
| 5,463,822 A | 11/1995 | Miller |
| 5,477,593 A | 12/1995 | Leick |
| D367,755 S | 3/1996 | Jones |
| D367,954 S | 3/1996 | Dion |
| 5,502,902 A | 4/1996 | Sussmann |
| 5,511,325 A | 4/1996 | Hieblinger |
| 5,526,585 A | 6/1996 | Brown et al. |
| 5,535,531 A | 7/1996 | Karabed et al. |
| 5,537,763 A | 7/1996 | Donnadieu et al. |
| 5,557,864 A | 9/1996 | Marks |
| 5,566,474 A | 10/1996 | Leick et al. |
| D375,831 S | 11/1996 | Perry |
| 5,596,820 A | 1/1997 | Edauw et al. |
| 5,599,000 A | 2/1997 | Bennett |
| 5,599,288 A | 2/1997 | Shirley et al. |
| 5,600,874 A | 2/1997 | Jungkind |
| 5,606,778 A | 3/1997 | Jungkind |
| 5,607,448 A | 3/1997 | Stahl et al. |
| D379,113 S | 5/1997 | McDonald et al. |
| 5,638,588 A | 6/1997 | Jungkind |
| 5,640,785 A | 6/1997 | Egelja |
| 5,647,104 A | 7/1997 | James |
| 5,651,198 A | 7/1997 | Sussmann |
| 5,669,116 A | 9/1997 | Jungkind |
| 5,692,319 A | 12/1997 | Parker et al. |
| 5,718,021 A | 2/1998 | Tatum |
| 5,718,065 A | 2/1998 | Locker |
| 5,720,084 A | 2/1998 | Chen |
| 5,732,483 A | 3/1998 | Cagliari |
| 5,732,648 A | 3/1998 | Aragon |
| 5,736,696 A | 4/1998 | Del Rosso |
| 5,737,854 A | 4/1998 | Sussmann |
| 5,755,044 A | 5/1998 | Veylupek |
| 5,756,298 A | 5/1998 | Burczak |
| 5,761,777 A | 6/1998 | Leick |
| 5,772,146 A | 6/1998 | Kawamoto et al. |
| 5,784,809 A | 7/1998 | McDonald |
| 5,791,068 A | 8/1998 | Bernier et al. |
| 5,819,378 A | 10/1998 | Doyle |
| 5,833,640 A | 11/1998 | Vazquez, Jr. et al. |
| 5,839,210 A | 11/1998 | Bernier et al. |
| 5,845,371 A | 12/1998 | Chen |
| 5,909,946 A | 6/1999 | Okajima |
| D413,197 S | 8/1999 | Faye |
| 5,934,599 A | 8/1999 | Hammerslag |
| 5,937,542 A | 8/1999 | Bourdeau |
| 5,956,823 A | 9/1999 | Borel |
| 5,971,946 A | 10/1999 | Quinn et al. |
| 6,015,110 A | 1/2000 | Lai |
| 6,038,791 A | 3/2000 | Cornelius et al. |
| 6,052,921 A | 4/2000 | Oreck |
| 6,070,886 A | 6/2000 | Cornelius et al. |
| 6,070,887 A | 6/2000 | Cornelius et al. |
| 6,083,857 A | 7/2000 | Bottger |
| 6,088,936 A | 7/2000 | Bahl |
| 6,102,412 A | 8/2000 | Staffaroni |
| D430,724 S | 9/2000 | Matis et al. |
| 6,119,318 A | 9/2000 | Maurer |
| 6,119,372 A | 9/2000 | Okajima |
| 6,128,835 A | 10/2000 | Ritter et al. |
| 6,128,836 A | 10/2000 | Barret |
| 6,148,489 A | 11/2000 | Dickie et al. |
| 6,202,953 B1 | 3/2001 | Hammerslag |
| 6,219,891 B1 | 4/2001 | Maurer et al. |
| 6,240,657 B1 | 6/2001 | Weber et al. |
| 6,256,798 B1 | 7/2001 | Egolf et al. |
| 6,267,390 B1 | 7/2001 | Maravetz et al. |
| 6,286,233 B1 | 9/2001 | Gaither |
| 6,289,558 B1 | 9/2001 | Hammerslag |
| 6,311,633 B1 | 11/2001 | Keire |
| D456,130 S | 4/2002 | Towns |
| 6,370,743 B2 | 4/2002 | Choe |
| 6,401,364 B1 | 6/2002 | Burt |
| 6,416,074 B1 | 7/2002 | Maravetz et al. |
| 6,467,195 B2 | 10/2002 | Pierre et al. |
| 6,477,793 B1 | 11/2002 | Pruitt et al. |
| 6,502,286 B1 | 1/2003 | Dubberke |
| 6,543,159 B1 | 4/2003 | Carpenter et al. |
| 6,568,103 B2 | 5/2003 | Durocher |
| 6,606,804 B2 | 8/2003 | Kaneko et al. |
| 6,694,643 B1 | 2/2004 | Hsu |
| 6,708,376 B1 | 3/2004 | Landry |
| 6,711,787 B2 | 3/2004 | Jungkind et al. |
| 6,735,829 B2 | 5/2004 | Hsu |
| 6,757,991 B2 | 7/2004 | Sussmann |
| 6,775,928 B2 | 8/2004 | Grande et al. |
| 6,792,702 B2 | 9/2004 | Borsoi et al. |
| 6,802,439 B2 | 10/2004 | Azam et al. |
| 6,823,610 B1 | 11/2004 | Ashley |
| 6,871,812 B1 | 3/2005 | Chang |
| 6,877,256 B2 | 4/2005 | Martin et al. |
| 6,899,720 B1 | 5/2005 | McMillan |
| 6,922,917 B2 | 8/2005 | Kerns et al. |
| 6,938,913 B2 | 9/2005 | Elkington |
| 6,945,543 B2 | 9/2005 | De Bertoli et al. |
| D510,183 S | 10/2005 | Tresser |
| 6,976,972 B2 | 12/2005 | Bradshaw |
| 6,993,859 B2 | 2/2006 | Martin et al. |
| D521,226 S | 5/2006 | Douglas et al. |
| 7,073,279 B2 | 7/2006 | Min |
| 7,076,843 B2 | 7/2006 | Sakabayashi |
| 7,082,701 B2 | 8/2006 | Dalgaard et al. |
| 7,096,559 B2 | 8/2006 | Johnson et al. |
| 7,134,224 B2 | 11/2006 | Elkington et al. |
| 7,266,911 B2 | 9/2007 | Holzer et al. |
| 7,281,341 B2 | 10/2007 | Reagan et al. |
| 7,293,373 B2 | 11/2007 | Reagan et al. |
| 7,331,126 B2 | 2/2008 | Johnson |
| 7,343,701 B2 | 3/2008 | Pare et al. |
| 7,367,522 B2 | 5/2008 | Chen |
| 7,386,947 B2 | 6/2008 | Martin et al. |
| 7,392,602 B2 | 7/2008 | Reagan et al. |
| 7,401,423 B2 | 7/2008 | Reagan et al. |
| 7,490,458 B2 | 2/2009 | Ford |
| 7,516,914 B2 | 4/2009 | Kovacevich et al. |
| 7,568,298 B2 | 8/2009 | Kerns |
| 7,582,102 B2 | 9/2009 | Heinz et al. |
| 7,584,528 B2 | 9/2009 | Hu |
| 7,591,050 B2 | 9/2009 | Hammerslag |
| 7,597,675 B2 | 10/2009 | Ingimundarson et al. |
| 7,600,660 B2 | 10/2009 | Kasper et al. |
| 7,617,573 B2 | 11/2009 | Chen |
| 7,624,517 B2 | 12/2009 | Smith |
| 7,648,404 B1 | 1/2010 | Martin |
| 7,650,705 B2 | 1/2010 | Donnadieu et al. |
| 7,694,354 B2 | 4/2010 | Philpott et al. |
| 7,752,774 B2 | 7/2010 | Ussher |
| 7,757,412 B2 | 7/2010 | Farys |

(56) References Cited

U.S. PATENT DOCUMENTS

| | | |
|---|---|---|
| 7,774,956 B2 | 8/2010 | Dua et al. |
| D626,322 S | 11/2010 | Servettaz |
| 7,841,106 B2 | 11/2010 | Farys |
| 7,871,334 B2 | 1/2011 | Young et al. |
| 7,877,845 B2 | 2/2011 | Signori |
| 7,900,378 B1 | 3/2011 | Busse |
| 7,908,769 B2 | 3/2011 | Pellegrini |
| 7,947,061 B1 | 5/2011 | Reis |
| 7,950,112 B2 | 5/2011 | Hammerslag et al. |
| 7,954,204 B2 | 6/2011 | Hammerslag et al. |
| 7,963,049 B2 | 6/2011 | Messmer |
| 7,992,261 B2 | 8/2011 | Hammerslag et al. |
| D646,790 S | 10/2011 | Castillo et al. |
| 8,056,150 B2 | 11/2011 | Stokes et al. |
| 8,074,379 B2 | 12/2011 | Robinson, Jr. et al. |
| 8,091,182 B2 | 1/2012 | Hammerslag et al. |
| 8,109,015 B2 | 2/2012 | Signori |
| D663,850 S | 7/2012 | Joseph |
| D663,851 S | 7/2012 | Joseph |
| 8,215,033 B2 | 7/2012 | Carboy et al. |
| 8,231,074 B2 | 7/2012 | Hu et al. |
| D665,088 S | 8/2012 | Joseph |
| 8,235,321 B2 | 8/2012 | Chen |
| 8,245,371 B2 | 8/2012 | Chen |
| 8,257,293 B2 | 9/2012 | Ingimundarson et al. |
| 8,266,827 B2 | 9/2012 | Dojan et al. |
| 8,277,401 B2 | 10/2012 | Hammerslag et al. |
| 8,302,329 B2 | 11/2012 | Hurd et al. |
| 8,303,527 B2 | 11/2012 | Joseph |
| 8,308,098 B2 | 11/2012 | Chen |
| 8,353,087 B2 | 1/2013 | Chen |
| 8,353,088 B2 | 1/2013 | Ha |
| D677,045 S | 3/2013 | Voskuil |
| D679,019 S | 3/2013 | Siddle et al. |
| 8,434,200 B2 | 5/2013 | Chen |
| 8,490,299 B2 | 7/2013 | Dua et al. |
| 8,516,662 B2 | 8/2013 | Goodman et al. |
| 8,578,632 B2 | 11/2013 | Bell et al. |
| 8,652,164 B1 | 2/2014 | Aston |
| 8,713,820 B2 | 5/2014 | Kerns et al. |
| 8,984,719 B2 | 3/2015 | Soderberg et al. |
| 9,072,341 B2 | 7/2015 | Jungkind |
| D735,987 S | 8/2015 | Hsu |
| 9,101,181 B2 | 8/2015 | Soderberg et al. |
| 9,125,455 B2 | 9/2015 | Kerns et al. |
| 9,138,030 B2 | 9/2015 | Soderberg et al. |
| 2002/0050076 A1 | 5/2002 | Borsoi et al. |
| 2002/0062579 A1 | 5/2002 | Caeran |
| 2002/0095750 A1 | 7/2002 | Hammerslag |
| 2002/0129518 A1 | 9/2002 | Borsoi et al. |
| 2002/0148142 A1 | 10/2002 | Oorei et al. |
| 2002/0166260 A1 | 11/2002 | Borsoi |
| 2002/0178548 A1 | 12/2002 | Freed |
| 2003/0079376 A1 | 5/2003 | Oorei et al. |
| 2003/0144620 A1 | 7/2003 | Sieller |
| 2003/0150135 A1 | 8/2003 | Liu |
| 2003/0177662 A1 | 9/2003 | Elkington et al. |
| 2003/0204938 A1 | 11/2003 | Hammerslag |
| 2004/0041452 A1 | 3/2004 | Williams |
| 2004/0211039 A1 | 10/2004 | Livingston |
| 2005/0054962 A1 | 3/2005 | Bradshaw |
| 2005/0060912 A1 | 3/2005 | Holzer et al. |
| 2005/0081339 A1 | 4/2005 | Sakabayashi |
| 2005/0081403 A1 | 4/2005 | Mathiew |
| 2005/0087115 A1 | 4/2005 | Martin |
| 2005/0098673 A1 | 5/2005 | Huang |
| 2005/0102861 A1 | 5/2005 | Martin |
| 2005/0126043 A1 | 6/2005 | Reagan et al. |
| 2005/0172463 A1 | 8/2005 | Rolla |
| 2005/0178872 A1 | 8/2005 | Hyun |
| 2005/0184186 A1 | 8/2005 | Tsoi et al. |
| 2005/0198866 A1 | 9/2005 | Wiper et al. |
| 2006/0015988 A1 | 1/2006 | Philpott et al. |
| 2006/0135901 A1 | 6/2006 | Ingimundarson et al. |
| 2006/0156517 A1 | 7/2006 | Hammerslag et al. |
| 2006/0179685 A1 | 8/2006 | Borel et al. |
| 2006/0185193 A1 | 8/2006 | Pellegrini |
| 2006/0287627 A1 | 12/2006 | Johnson |
| 2007/0006489 A1 | 1/2007 | Case Jr., et al. |
| 2007/0063459 A1 | 3/2007 | Kavarsky |
| 2007/0068040 A1 | 3/2007 | Farys |
| 2007/0084956 A1 | 4/2007 | Chen |
| 2007/0113524 A1 | 5/2007 | Lander |
| 2007/0128959 A1 | 6/2007 | Cooke |
| 2007/0169378 A1 | 7/2007 | Sodeberg et al. |
| 2008/0016717 A1 | 1/2008 | Ruban |
| 2008/0060167 A1 | 3/2008 | Hammerslag et al. |
| 2008/0060168 A1 | 3/2008 | Hammerslag et al. |
| 2008/0066272 A1 | 3/2008 | Hammerslag et al. |
| 2008/0066345 A1 | 3/2008 | Hammerslag et al. |
| 2008/0066346 A1 | 3/2008 | Hammerslag et al. |
| 2008/0068204 A1 | 3/2008 | Carmen et al. |
| 2008/0083135 A1 | 4/2008 | Hammerslag et al. |
| 2008/0092279 A1 | 4/2008 | Chiang |
| 2008/0172848 A1 | 7/2008 | Chen |
| 2008/0196224 A1 | 8/2008 | Hu |
| 2009/0019734 A1 | 1/2009 | Reagan et al. |
| 2009/0071041 A1 | 3/2009 | Hooper |
| 2009/0090029 A1 | 4/2009 | Kishino |
| 2009/0172928 A1 | 7/2009 | Messmer et al. |
| 2009/0184189 A1 | 7/2009 | Soderberg et al. |
| 2009/0272007 A1 | 11/2009 | Beers et al. |
| 2009/0277043 A1 | 11/2009 | Graser et al. |
| 2010/0064547 A1 | 3/2010 | Kaplan |
| 2010/0101061 A1 | 4/2010 | Ha |
| 2010/0139057 A1 | 6/2010 | Soderberg et al. |
| 2010/0154254 A1 | 6/2010 | Fletcher |
| 2010/0175163 A1 | 7/2010 | Litke |
| 2010/0251524 A1 | 10/2010 | Chen |
| 2010/0299959 A1 | 12/2010 | Hammerslag |
| 2010/0319216 A1 | 12/2010 | Grenzke et al. |
| 2011/0000173 A1 | 1/2011 | Lander |
| 2011/0071647 A1 | 3/2011 | Mahon |
| 2011/0162236 A1 | 7/2011 | Voskuil et al. |
| 2011/0167543 A1 | 7/2011 | Kovacevich et al. |
| 2011/0191992 A1 | 8/2011 | Chen |
| 2011/0197362 A1 | 8/2011 | Chella et al. |
| 2011/0225843 A1 | 9/2011 | Kerns et al. |
| 2011/0258876 A1 | 10/2011 | Baker et al. |
| 2011/0266384 A1 | 11/2011 | Goodman et al. |
| 2011/0303782 A1 | 12/2011 | Hu et al. |
| 2012/0000091 A1 | 1/2012 | Cotterman et al. |
| 2012/0004587 A1 | 1/2012 | Nickel et al. |
| 2012/0005995 A1 | 1/2012 | Emery |
| 2012/0023717 A1 | 2/2012 | Chen |
| 2012/0047620 A1 | 3/2012 | Ellis et al. |
| 2012/0101417 A1 | 4/2012 | Joseph |
| 2012/0102783 A1 | 5/2012 | Swigart et al. |
| 2012/0138882 A1 | 6/2012 | Moore et al. |
| 2012/0157902 A1 | 6/2012 | Castillo et al. |
| 2012/0167290 A1 | 7/2012 | Kovacevich et al. |
| 2012/0174437 A1 | 7/2012 | Heard |
| 2012/0228419 A1 | 9/2012 | Chen |
| 2012/0246974 A1 | 10/2012 | Hammerslag et al. |
| 2012/0310273 A1 | 12/2012 | Thorpe |
| 2013/0012856 A1 | 1/2013 | Hammerslag et al. |
| 2013/0014359 A1 | 1/2013 | Chen |
| 2013/0019501 A1 | 1/2013 | Gerber |
| 2013/0025100 A1 | 1/2013 | Ha |
| 2013/0091667 A1 | 4/2013 | Chen |
| 2013/0091674 A1 | 4/2013 | Chen |
| 2013/0092780 A1 | 4/2013 | Soderberg et al. |
| 2013/0239303 A1 | 9/2013 | Cotterman |
| 2013/0269219 A1 | 10/2013 | Burns et al. |
| 2013/0277485 A1 | 10/2013 | Soderberg et al. |
| 2013/0340283 A1 | 12/2013 | Bell et al. |
| 2013/0345612 A1 | 12/2013 | Bannister et al. |
| 2014/0082963 A1 | 3/2014 | Beers |
| 2014/0094728 A1 | 4/2014 | Soderberg et al. |
| 2014/0117140 A1 | 5/2014 | Goodman et al. |
| 2014/0123440 A1 | 5/2014 | Capra et al. |
| 2014/0123449 A1 | 5/2014 | Soderberg et al. |
| 2014/0208550 A1 | 7/2014 | Neiley |
| 2014/0221889 A1 | 8/2014 | Burns et al. |

(56) References Cited

U.S. PATENT DOCUMENTS

| | | |
|---|---|---|
| 2014/0257156 A1 | 9/2014 | Capra et al. |
| 2014/0290016 A1 | 10/2014 | Lovett et al. |
| 2014/0359981 A1 | 12/2014 | Cotterman et al. |
| 2015/0007422 A1 | 1/2015 | Cavanagh et al. |
| 2015/0014463 A1 | 1/2015 | Converse et al. |
| 2015/0026936 A1 | 1/2015 | Kerns et al. |
| 2015/0033519 A1 | 2/2015 | Hammerslag et al. |
| 2015/0059206 A1 | 3/2015 | Lovett et al. |
| 2015/0076272 A1 | 3/2015 | Trudel et al. |
| 2015/0089779 A1 | 4/2015 | Lawrence et al. |
| 2015/0089835 A1 | 4/2015 | Hammerslag et al. |
| 2015/0101160 A1 | 4/2015 | Soderberg et al. |
| 2015/0150705 A1 | 6/2015 | Capra et al. |
| 2015/0151070 A1 | 6/2015 | Capra et al. |
| 2015/0190262 A1 | 7/2015 | Capra et al. |
| 2015/0223608 A1 | 8/2015 | Capra et al. |
| 2015/0237962 A1 | 8/2015 | Soderberg et al. |
| 2015/0335458 A1 | 11/2015 | Romo |
| 2016/0120267 A1 | 5/2016 | Burns et al. |
| 2016/0206047 A1 | 7/2016 | Hammerslag et al. |

FOREIGN PATENT DOCUMENTS

| | | |
|---|---|---|
| CH | 199766 | 9/1938 |
| CH | 204 834 A | 5/1939 |
| CN | 2613167 | 4/2004 |
| CN | 201015448 | 2/2008 |
| DE | 515 435 C | 5/1931 |
| DE | 641976 | 2/1937 |
| DE | 23 41 658 | 3/1974 |
| DE | 29 00 077 A1 | 7/1980 |
| DE | 31 01 952 A1 | 9/1982 |
| DE | 38 13 470 | 11/1989 |
| DE | 43 02 401 A1 | 8/1994 |
| DE | 43 05 671 A1 | 9/1994 |
| DE | 9308037 | 10/1994 |
| DE | 43 26 049 A1 | 2/1995 |
| DE | 9315776 | 3/1995 |
| DE | 29503552.8 | 5/1995 |
| DE | 196 24 553 | 1/1998 |
| DE | 19945045 A1 | 3/2001 |
| DE | 20 2010 000 354 U1 | 6/2010 |
| DE | 11 2013 005 273 T5 | 9/2015 |
| EP | 0 056 953 | 8/1982 |
| EP | 0 099 504 | 2/1984 |
| EP | 0 123 050 | 10/1984 |
| EP | 0 155 596 | 9/1985 |
| EP | 0 201 051 | 11/1986 |
| EP | 0 255 869 | 2/1988 |
| EP | 0 393 380 | 10/1990 |
| EP | 0 589 232 A1 | 3/1994 |
| EP | 0 589 233 A1 | 3/1994 |
| EP | 0 614 625 A1 | 9/1994 |
| EP | 0 651 954 A1 | 5/1995 |
| EP | 0 679 346 | 11/1995 |
| EP | 0 693 260 B1 | 1/1996 |
| EP | 0 734 662 A1 | 10/1996 |
| EP | 0 848 917 | 6/1998 |
| EP | 0 923 965 | 6/1999 |
| EP | 0 937 467 | 8/1999 |
| EP | 1163860 | 12/2001 |
| EP | 1 219 195 | 7/2002 |
| EP | 1 236 412 A | 9/2002 |
| EP | 2298107 B1 | 3/2011 |
| EP | 2359708 | 8/2011 |
| FR | 610 582 A | 9/1926 |
| FR | 1 404 799 | 5/1965 |
| FR | 2 019 991 A | 7/1970 |
| FR | 2 598 292 A1 | 11/1987 |
| FR | 2 726 440 A1 | 5/1996 |
| FR | 2 770 379 A1 | 5/1999 |
| FR | 2 814 919 A1 | 4/2002 |
| GB | 189911673 | 7/1899 |
| GB | 216400 | 5/1924 |
| GB | 2 449 722 A | 12/2008 |
| IT | 1220811 | 6/1990 |
| IT | 2003 A 000197 | 4/2003 |
| IT | 2003 A 000198 | 4/2003 |
| JP | 51-121375 | 10/1976 |
| JP | 53-124987 | 3/1977 |
| JP | 54-108125 | 2/1978 |
| JP | H02-236025 | 9/1990 |
| JP | 6-284906 | 10/1994 |
| JP | 08-308608 A | 11/1996 |
| JP | 3030988 | 11/1996 |
| JP | 3031760 | 12/1996 |
| JP | 10-199366 | 7/1998 |
| JP | 2004-016732 | 1/2004 |
| JP | 2004-041666 | 2/2004 |
| JP | 2009-504210 | 2/2009 |
| KR | 20-0367882 | 11/2004 |
| KR | 20-0400568 | 8/2005 |
| KR | 10-0598627 | 7/2006 |
| KR | 10-0953398 | 4/2010 |
| KR | 10-1025134 B1 | 3/2011 |
| KR | 10-1028468 | 4/2011 |
| KR | 10-1053551 | 7/2011 |
| WO | 94/27456 | 12/1994 |
| WO | 95/11602 | 5/1995 |
| WO | 1995/03720 | 9/1995 |
| WO | 98/33408 | 8/1998 |
| WO | 98/37782 | 9/1998 |
| WO | 99/09850 | 3/1999 |
| WO | 99/15043 | 4/1999 |
| WO | 99/43231 | 9/1999 |
| WO | 00/53045 | 9/2000 |
| WO | 2000/76337 A1 | 12/2000 |
| WO | 01/08525 | 2/2001 |
| WO | 01/15559 | 3/2001 |
| WO | 02/051511 | 7/2002 |
| WO | 2004/093569 | 11/2004 |
| WO | 2005/013748 A1 | 2/2005 |
| WO | 2007/016983 | 2/2007 |
| WO | 2008/015214 | 2/2008 |
| WO | 2008/033963 | 3/2008 |
| WO | 2009/134858 | 11/2009 |
| WO | 2010/059989 A2 | 5/2010 |
| WO | 2012/165803 A2 | 12/2012 |
| WO | 2015/035885 | 3/2015 |
| WO | 2015/179332 A1 | 11/2015 |
| WO | 2015/181928 A1 | 12/2015 |

OTHER PUBLICATIONS

International Search Report and Written Opinion for PCT/US2017/065355 dated May 24, 2018, 23 pages.
U.S. Appl. No. 09/956,601, filed Sep. 18, 2001, Hammerslag.
ASOLO® Boot Brochure Catalog upon information and belief date is as early as Aug. 22, 1997, 12 pages.
La Sportiva, A Technical Lightweight Double Boot for Cold Environments, 1 page. Accessed on May 27, 2015. Retrieved from http://www.sportiva.com/products/footwear/mountain/spantik.
"Strength of materials used to make my Safety Harnesses," Elaine, Inc. Jul. 9, 2012. Retrieved from <https://web.archive.org/web/20120709002720/http://www.childharness.ca/strength_data. html> on Mar. 17, 2014, 2 pages.
International Search Report and Written Opinion for PCT/US2013/032326 dated Jun. 14, 2013, 27 pages.
International Preliminary Report on Patentability for PCT/US2013/032326 dated Sep. 16, 2014, 6 pages.
International Search Report and Written Opinion for PCT/US2013/057637 dated Apr. 7, 2014, 34 pages.
International Preliminary Report on Patentability for PCT/US2013/057637 dated Mar. 3, 2015, 9 pages.
International Search Report and Written Opinion for PCT/US2013/068342 dated Apr. 7, 2014, 29 pages.
International Preliminary Report on Patentability for PCT/US2013/068342 dated May 5, 2015, 9 pages.
International Search Report and Written Opinion for PCT/US2014/014952 dated Apr. 25, 2014, 17 pages.

(56) References Cited

OTHER PUBLICATIONS

International Preliminary Report on Patentability for PCT/US2014/014952 dated Aug. 11, 2015, 9 pages.
International Search Report and Written Opinion for PCT/US2014/066212 dated Apr. 22, 2015, 16 pages.
International Search Report and Written Opinion for PCT/US2014/032574 dated Oct. 31, 2014, 19 pages.
International Search Report and Written Opinion for PCT/US2014/045291 dated Nov. 6, 2014, 12 pages.
International Search Report and Written Opinion for PCT/US2014/013458 dated May 19, 2014, 12 pages.
International Preliminary Report on Patentability for PCT/US2014/013458 dated Jul. 28, 2015, 7 pages.
International Search Report and Written Opinion for PCT/US2013/068814 dated Jun. 9, 2014, 18 pages.
International Preliminary Report on Patentability for PCT/US2013/068814 dated May 12, 2015, 12 pages.
Notice of Reasons for Rejection from the Japanese Patent Office dated Feb. 26, 2015 for design application No. 2014-015570, 4 pages.
Receipt of Certificate of Design Registration No. 1529678 from the Japanese Patent Office for design application No. 2014-015570 dated Jun. 26, 2015, 1 page.
International Search Report and Written Opinion for PCT/US2014/055710 dated Jul. 6, 2015, 19 pages.
International Search Report and Written Opinion for PCT/US2014/054420 dated Jul. 6, 2015, 21 pages.
The Preliminary Rejections from the Korean Intellectual Property Office for Application No. 30-2014-34959 dated Aug. 7, 2015, is not translated into English. The document requests a renaming of the application to be in accordance with Korean patent law, 5 pages total.
The Preliminary Rejections from the Korean Intellectual Property Office for Application No. 30-2014-34959 dated Apr. 7, 2015, is not translated into English. The document requests a revision of the drawings to be in accordance with Korean patent law, 6 pages total.
Certificate of Design Registration No. 30-809409 on Aug. 3, 2015 from the Korean Intellectual Property Office for Appln No. 30-2015-11475, 2 pages.
Certificate of Design Registration No. 30-809410 on Aug. 3, 2015 from the Korean Intellectual Property Office for Appln No. 30-2015-11476, 2 pages.
European Search Report for EP 14168875 dated Oct. 29, 2014, 9 pages.
International Search Report and Written Opinion for PCT/US2014/020894 dated Jun. 20, 2014, 12 pages.
International Preliminary Report on Patentability for PCT/US2014/020894 dated Sep. 8, 2015, 7 pages.
International Search Report and Written Opinion for PCT/US2014/041144 dated Dec. 10, 2014, 13 pages.
International Preliminary Report on Patentability for PCT/US2014/032574 dated Oct. 6, 2015, 12 pages.
International Search Report and Written Opinion for PCT/US2014/046238 dated Nov. 21, 2014, 17 pages.
Office Action received Oct. 8, 2015 from the German Patent and Trademark Office for Appln No. 402015100191.2, regarding the title of the invention, 2 pages.
Anonymous, "Shore durometer," Wikipedia, the free encyclopedia, Mar. 10, 2012, XP002747470, Retrieved from the Internet: URL: https://en.wikipedia.org/w/index.php?title=Shore_durometer&oldid=481128180 [retrieved on Oct. 20, 2015] * shore A, shore D, durometer, polymer, rubber, gel; the whole document *, 6 pages.
Notice of Reasons for Rejection from the Japanese Patent Office dated Oct. 5, 2015 for design application No. 2015-004923, 4 pages.
"Save Tourniquet," 3 pages. Copyright 2015. Accessed on Dec. 11, 2015. Retrieved from http://www.savetourniquet.com/.
International Preliminary Report on Patentability for PCT/US2014/041144 dated Dec. 8, 2015, all pages.
Supplementary European Search Report for EP 13761841 dated Oct. 21, 2015, all pages.
Notice of Reasons for Rejection for Japanese Patent Application No. 2016-518004 dispatched Jan. 27, 2017, 9 pages.
European Search Report for EP 14 80 6796 dated May 11, 2017, all pages.

REEL BASED CLOSURE SYSTEM

CROSS-REFERENCE TO RELATED APPLICATIONS

This application claims priority to Provisional U.S. Patent Application No. 62/438,288 filed Dec. 22, 2016, entitled "Reel Based Closure System" and Provisional U.S. Patent Application No. 62/432,175 filed Dec. 9, 2016, entitled "Reel Based Closure Systems." The entire disclosure of both of the aforementioned Provisional U.S. patent applications are hereby incorporated by reference, for all purposes, as if fully set forth herein.

BACKGROUND OF THE INVENTION

The present disclosure is related to reel based closure devices for various articles, such as braces, medical devices, shoes, clothing, apparel, and the like. Such articles typically include some closure system, which allows the article to be placed about a body part and closed or tightened about the body part. The closure systems are typically used to maintain or secure the article about the body part. For example, shoes are typically placed over an individual's foot and the shoelace is tensioned and tied to close and secure the shoe about the foot. Conventional closure systems have been modified in an effort to increase the fit and/or comfort of the article about the body part. For example, shoe lacing configurations and/or patterns have been modified in an attempt to increase the fit and/or comfort of wearing shoes. Conventional closure systems have also been modified in an effort to decrease the time in which an article may be closed and secured about the body part. These modifications have resulted in the use of various pull cords, straps, and tensioning devices that enable the article to be quickly closed and secured to the foot.

BRIEF DESCRIPTION OF THE INVENTION

The embodiments described herein provide reel based closure devices, and components therefor, that may be used to tension a lace or tension member and thereby tighten an article or other item. According to one aspect, a closure device for tightening an article includes a housing component having an interior region, a tension member, a spool component rotatably positioned within the interior region of the housing, and a tightening component positioned axially above the spool component and operably coupled therewith so that an operation of the tightening component causes the spool component to rotate within the housing component's interior region to wind the tension member about the spool component. The closure device also includes a coupling component that is separate from the tension member and that frictionally engages with a distal end of the tension member so that the coupling component is removably fixed about the tension member. The spool component includes a coupling feature within which the coupling component is positioned to attach the tension member to the spool.

According to another aspect, a coupling component that is securable to a tension member of a reel based closure system includes a main body that is separate from the tension member and at least one aperture that is positioned about the main body so that a distal end of the tension member is insertable through the aperture of the main body. The coupling component is configured so that the coupling component frictionally engages with the distal end of the tension member to fixedly secure the coupling component to the coupling component. The coupling component frictionally engages with the tension member without require a knot to be tied in the tension member and without require any other alteration of the tension member.

According to another aspect, a method of coupling a tension member with a reel based closure device includes inserting the tension member through a channel of a spool component of the reel based closure device. The method also includes coupling a distal end of the tension member with a coupling component that is separate from the tension member and that frictionally engages with the distal end of the tension member to fix the coupling component about the distal end of the tension member. The method further includes retracting the tension member through the channel of the spool component so that the coupling component engages with the channel and thereby prevents the tension member from being pulled through the spool component's channel.

According to another aspect, a reel based closure system includes a base member that defines an interior region and a housing component that is positionable within the interior region of the base member and that is releasably coupleable with the base member. The reel based closure system also includes a spool component that is rotatably positioned within the housing component. The spool component is configured so that a tension member is windable about the spool component. The reel based closure system further includes a tightening component that is rotatably coupled with the housing component and that is operably coupled with the spool component so that an operation of the tightening component causes the spool component to rotate within the housing component to wind the tension member about the spool component and thereby tighten an article. The housing component is coupleable with the base component by axially inserting the housing component within the interior region of the base member and by rotating the housing component relative to the base member. The housing component is detachable from the base component without requiring a rotation of the housing component relative to the base member.

According to another aspect, a reel based closure system includes a base member that defines an interior region and a housing component that is positionable within the interior region of the base member and that is releasably coupleable with the base member. The reel based closure system also includes a spool component that is rotatably positioned within the housing component. The spool component is configured so that a tension member is windable about the spool component. The reel based closure system further includes a tightening component that is rotatably coupled with the housing component and that is operably coupled with the spool component so that an operation of the tightening component causes the spool component to rotate within the housing component to wind the tension member about the spool component. The housing component is rotatable relative to the base member to secure the housing component within the interior region of the base member and the housing component is axially moveable relative to the base member to detach the housing component from the base member.

According to another aspect, a method of assembly of a reel based closure system includes providing a reel based closure system that includes: a base member that defines an interior region, a housing component, a spool component that is rotatably positioned within the housing component, and a tightening component that is rotatably coupled with the housing component and that is operably coupled with the spool component to cause the spool component to rotate within the housing component upon an operation of the tightening component. The method also includes axially inserting a bottom end of the housing component within the interior region of the base member and rotating the housing component relative to the base member to secure the housing component about the base member. After the housing component is secured to the base member, the housing component is detachable from the base component without requiring a counter rotation of the housing component relative to the base member.

According to another aspect, a reel based closure device for tightening an article includes a housing component having an interior region and a spool component that is rotatably positioned within the interior region of the housing component. The spool component is configured so that a tension member is windable about the spool component to tighten the article. The reel based closure device also includes a drive component that is positioned axially above the spool component and that is operably coupled therewith to allow the spool component to rotate in a first direction within the housing component's interior region while preventing rotation of the spool component in a second direction. The reel based closure device further includes a tightening component that is rotatably coupled with the housing and that is positioned axially above the drive component and coupled with the drive component so that an operation of the tightening component causes the spool component to rotate within the housing component's interior region in the first direction to wind the tension member about the spool component. The reel based closure device additionally includes a coupling component that is positioned axially below the spool component. The coupling component has a central boss that protrudes axially upward into the interior region of the housing component and through an aperture of the spool component and through an aperture of the drive component so that the spool component and the drive component are rotatable about the central boss. The coupling component also includes a pair of arms that extend radially outward from the central boss and that attach to a bottom end of the housing component. A distal end of each arm includes an upward turned lip or tab that curves around a bottom edge of the housing component when the pair of arms are attached to the bottom end of the housing component.

According to another aspect, a reel based closure device includes a housing having an interior region, a spool that is rotatably positioned within the interior region of the housing, and a tightening member that is rotatably coupled with the housing and that is operably coupled with the spool so that an operation of the tightening member causes the spool to rotate within the housing in a first direction to wind a tension member about the spool. The reel based closure device also includes a coupling member that is positioned axially below the spool. The coupling member has a central boss that protrudes axially upward into the interior region of the housing and a pair of arms that extend radially outward from the central boss and that attach to a bottom end of the housing. A distal end of each arm includes a lip or tab that curves upward and that detachably couples with the housing when the pair of arms are attached to the bottom end of the housing.

According to another aspect, a method of assembling a reel based closure device includes coupling a drive component with a tightening component and coupling the tightening component with a top end of a housing component so that the drive component faces an interior region of the housing component. The method also includes inserting a spool component within the housing component so that a top end of the spool component faces a bottom surface of the drive component and coupling a coupling component with a bottom end of the housing component so that a central boss of the coupling component extends into the interior region of the housing component. The coupling component includes a pair of arms that extend radially outward from the central boss and that attach to the bottom end of the housing component. A distal end of each arm includes a lip or tab that curves upward and that detachably couples with the housing component when the pair of arms are attached to the bottom end of the housing component.

BRIEF DESCRIPTION OF THE DRAWINGS

The present invention is described in conjunction with the appended figures.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

The embodiments described herein provide reel based closure devices (hereinafter closure system or reel based device/system) that may be used to tension a lace or tension member and thereby tighten an article or other item. The article may be a variety of items including a pack (i.e., back pack, book bag, etc.), an article of clothing (i.e., hats, gloves, belt, etc.), sports apparel (boots, snowboard boots, ski boots, etc.), medical braces (i.e., back braces, knee braces, wrist brace, ankle brace, etc.), and various other items or apparel. A specific embodiment in which the closure system may be employed involves footwear, such as shoes, boots, sandals, etc.

Figure 1:
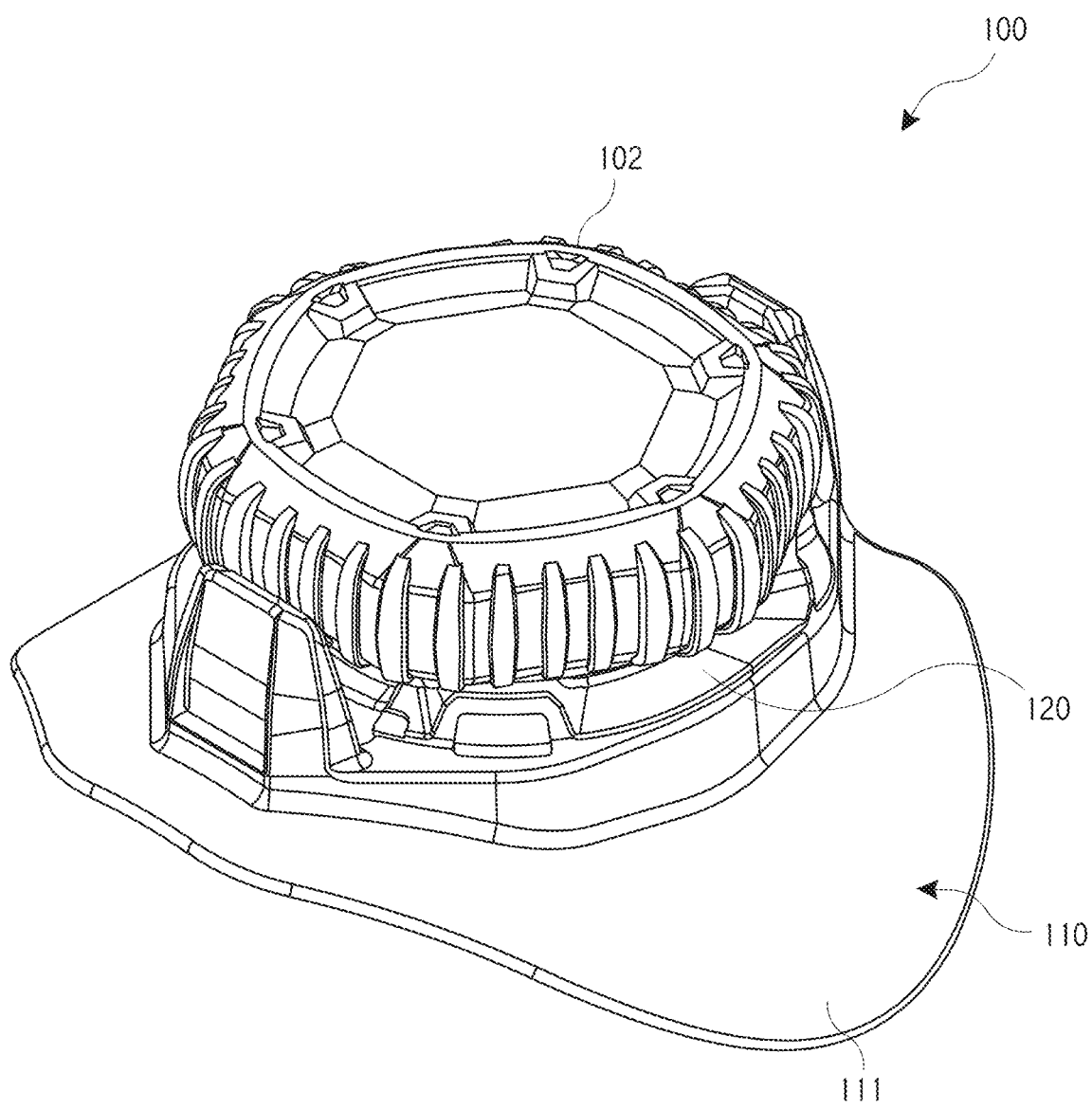
FIG. 1 illustrates a perspective view of a reel based closure device or system in an assembled state.

Referring now to FIG. 1, illustrated is a perspective view of the reel based closure device or system 100 (hereinafter closure system 100) in an assembled state. The closure system 100 includes a tightening component 102, such as a reel or knob (hereinafter knob 102), that is designed to be grasped and rotated by a user. The knob 102 is positioned with respect to the closure system 100 so that it is easily accessible to a user. The knob 102 is illustrated as having a hexagonal profile or shape when viewed from a top surface, although various other knob shapes or configurations may be employed, such as circular, octagonal, triangular, and the like. The knob 102 is attached to a housing or housing component 120 (hereinafter housing 120) that is in turn attached to a base member or bayonet 110 (hereinafter base member 110). The housing 120 includes an interior region within which one or more components of the closure system 100 are positioned. The base member 110 is configured to be attached to the article (e.g., shoe, boot, etc.) that employs the closure system 100 for adjusting the tightness or fit of the article. For example, the base member 100 includes a flange 111 that may be stitched, adhered, adhesively bonded, welded (RF, ultrasonic, etc.), or otherwise attached to the article. In some instances, the base member 110 or flange 111 may be inserted molded onto the article that employs the closure system 100. Details of the attachment or coupling of the knob 102, housing 120, and base member 110 are provided in greater detail below.

Figure 2A:
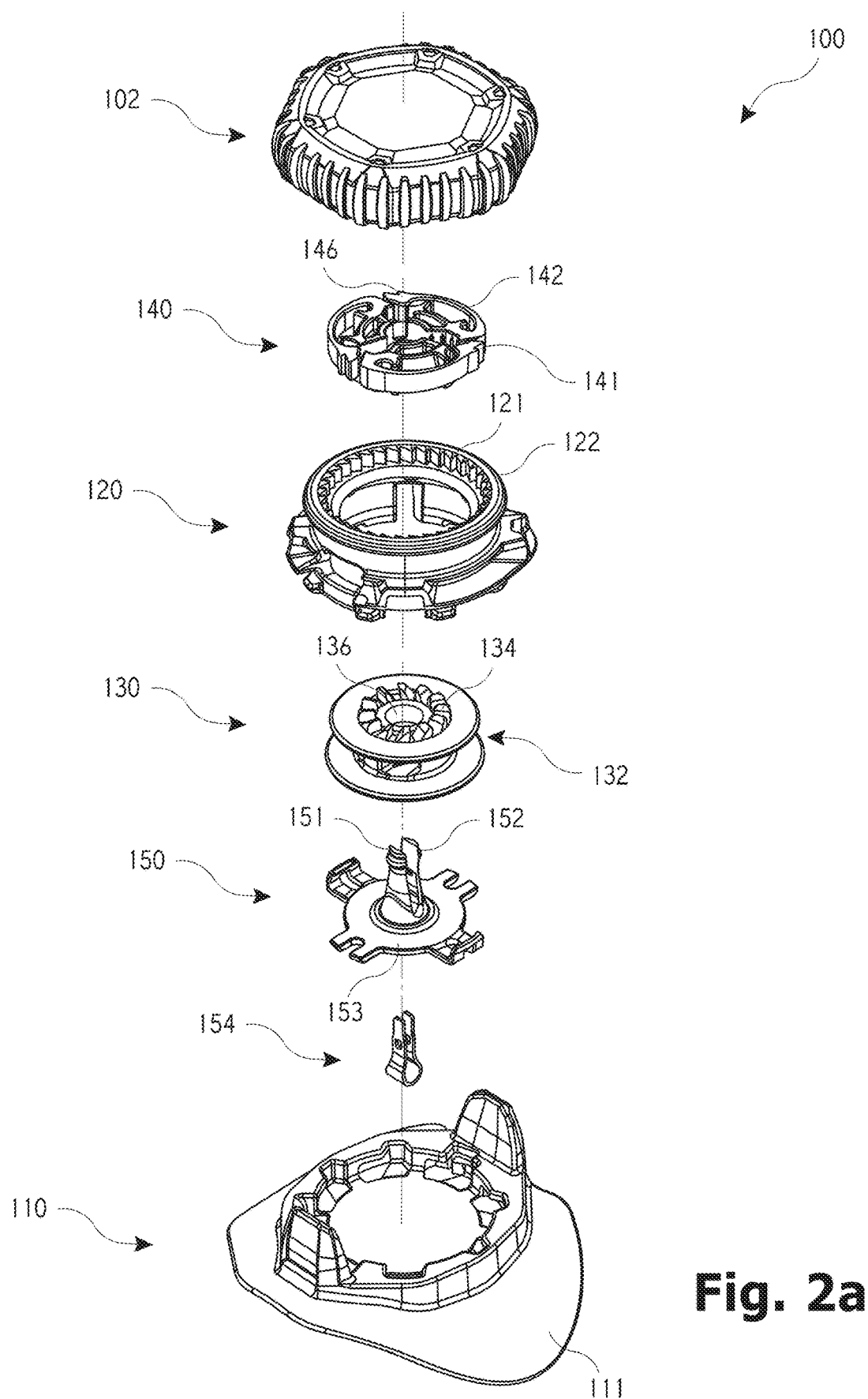
FIGS. 2a-b illustrate exploded perspective views of the closure system of FIG. 1.
Figure 2B:
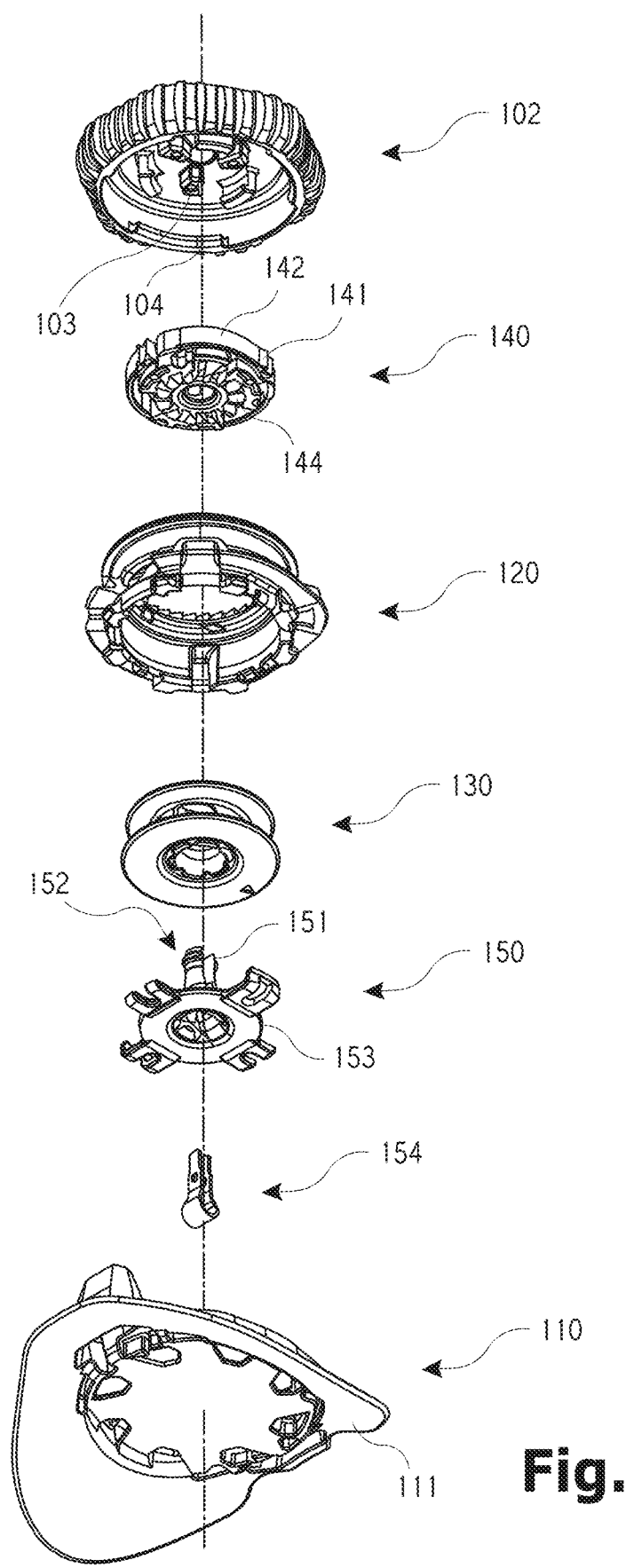

FIGS. 2a and 2b illustrate exploded perspective views of the closure system 100. Additional details of the knob 102, housing 120, and base member 110 are evident in the exploded perspective views of FIGS. 2a-b. Additional components of the closure system 100 are also illustrated in the exploded perspective views of FIGS. 2a-b. These additional components are housed or contained within the housing 120 of the closure system 100 when the system is assembled and thus, these additional components are typically not visible in the assembled view of the closure system 100. The additional components include a drive component (e.g., a pawl disc or mechanism 140), a spool component 130, and a coupling component or member 150. The spool component 130 (hereinafter spool 130) is rotatably positioned within the interior region of the housing 120 and is configured so that a tension member (not shown) is windable about the spool 130 in order to tension the tension member and tighten the article. The drive component (hereinafter pawl disc 140) is positioned axially above the spool 130 and is operably coupled with the spool 130 to allow the spool to rotate in a first direction within the interior region of the housing 120 while preventing rotation of the spool 130 in a second direction within the housing 120. The knob 102 is rotatably coupled with the housing 102 and is positioned axially above the pawl disc 140 and operably coupled therewith so that an operation of the knob 102 (e.g., rotation of the knob 102) causes the spool 130 to rotate within the interior region of the housing 120 in the first direction to wind the tension member about the spool 130. The coupling component or member 150 is positioned axially below the spool 130. A central boss 152 of the coupling component or member 150 protrudes axially upward into the interior region of the housing 120.

As briefly described above, the pawl disc 140 is configured to allow rotation of the spool 130 in one direction (i.e., a tightening direction) while preventing rotation of the spool 130 in an opposite direction (i.e., loosening direction) within the housing 120. The tightening direction may be a clockwise or counterclockwise direction as desired while the loosening direction would be the opposite direction. To enable rotation of the spool 130, the pawl disc 140 includes pawl teeth 141 that are positioned on the distal end of cantilevered arms 142. The pawl teeth 141 engage with housing teeth 121 of the housing 120 in a ratchet like manner to enable a one-way winding motion of the spool 130 within the housing 120. The pawl disc 140 is positioned within, and attached to, an interior region of the knob 102 so that the knob 102 and pawl disc 140 function as a unitary component. Drive member 103 of the knob 102 engage with, and are positioned within, apertures on the top surface of the pawl disc 140. The drive members 103 transfer rotational forces or torque from the knob 102 to the pawl disc 140.

Thus, as the knob 102 is rotated in the tightening direction, the pawl disc 140 is likewise rotated in the tightening direction.

Rotation of the pawl disc 140 in the tightening direction causes the pawl teeth 141 to deflect radially inward about the housing teeth 121 due to a spring like flexing or displacement of the cantilevered arms 142. The pawl teeth 141 are biased radially outward so that they engage with the housing teeth 121. A sloped surface of the housing teeth 121 causes the pawl teeth 141 to deflect radially inward as the pawl disc 140 is rotated in the tightening direction and engagement of the housing teeth 121 and pawl teeth 141 prevents rotation of the pawl disc 140 in the loosening direction.

Although the pawl teeth 141 are illustrates as projecting radially outward, in some embodiments the pawl teeth 141 may project radially inward or axially upward or downward. In such embodiments, the teeth 121 that engage with the pawl teeth 141 would also be positioned somewhere other than on the inner wall of the housing 120, such as on an exterior wall of an inner cylindrical wall, or on a separate toothed component or disc that is attachable to the housing 120. In such embodiments, the teeth 121 would face radially outward, axially upward, or axially downward in order to engage with the pawl teeth 141 of the pawl disc 140. In yet another embodiment, the pawl disc 140 may be integrally formed with the knob 102, spool 130, or with the housing 120.

In the embodiment of FIGS. 2a and 2b, the pawl disc 140 includes a plurality of axially oriented teeth 144 that are positioned on the bottom surface of the pawl disc 140. The axially oriented teeth 144 engage with corresponding axially oriented teeth 134 positioned on the top surface of the spool 130. The axially oriented teeth, 134 and 144, of the spool 130 and pawl disc 140 engage so that the rotational forces or torque is transferred from the pawl disc 140 to the spool 130, which causes the spool 130 to rotate in the tightening direction in response to rotation of the pawl disc 140 in the tightening direction.

As the spool 130 is rotated in the tightening direction, a lace, cord, or tension member (not shown) that is attached to the spool 130 is wound around a central portion or channel 132 of the spool 130. The spool 130 is rotationally positioned about the coupling component or member 150 (hereinafter coupling member 150) by inserting the central boss 152 through a central aperture or opening 136 of the spool 130. The spool 130 is able to spin or rotation about the boss 152 with negligible friction or drag. A top or distal end of the boss 152 is inserted through an aperture or opening 146 of the pawl disc 140 to rotationally position the spool 130 about the boss 152.

The pawl disc 140 is operationally engaged with the top end of the boss 152 in a manner that enables the pawl disc 140 and/or knob 102 to be supported in one of two positions: an engaged position and a disengaged position. In the engaged position, the knob 102 and pawl disc 140 are positioned axially downward with respect to the housing 120 and spool 130 so that the axially oriented teeth, 134 and 144, of the spool 130 and pawl disc 140 contact and engage with one another. In the disengaged position, the pawl disc 140 is positioned axially upward with respect to the housing 120 and spool 130 so that the axially oriented teeth, 134 and 144, of the spool 130 and pawl disc 140 disengage and do not contact one another. Since the axially oriented teeth, 134 and 144, of the spool 130 and pawl disc 140 are disengaged, the spool 130 is able to spin or rotate freely within the housing 120 in the loosening direction. In the disengaged position, the pawl teeth 141 of the pawl disc 140 may disengage from the housing teeth 121, which may allow the knob 102 and pawl disc 140 to be rotated in the loosening direction. In other embodiments, the pawl teeth 141 of the pawl disc 140 may remain engaged with the housing teeth 121 in the disengaged position, which may prevent rotation of the pawl disc 140 and/or knob 102 in the loosening direction.

In some embodiments, the knob 102 may likewise be positioned axially upward with respect to the housing 120 and spool 130 in the disengaged position. In such embodiments, axially upward movement of the knob 102 and pawl disc 140 into the disengaged position may be achieved by pulling axially upward on the knob 102. In other embodiments, the knob 102 may remain axially stationary with respect to the housing 120 and spool 130 while the pawl disc 140 is moved to the axially upward position. In such embodiments, axially upward movement of the pawl disc 140 may be achieved by rotating the knob 102 in the loosening direction and/or by employing a separate release mechanism or button, such as a lever, button, clamp, and the like. To move the pawl disc 140 axially upward, the knob 102 and pawl disc 140 may include cammed, ramped, or sloped surfaces, or another mechanism, that moves the pawl disc 140 axially upward as the knob 102 is rotated in the loosening direction.

The top end of the boss 152 supports and maintains the pawl disc 140 and/or knob 102 in the engaged and disengaged positions via an annular projection or member 151. The annular projection 151 has a diameter that is greater than the diameter of the central aperture 146 of the pawl disc 140, which causes the annular projection 151 to interfere with and impede axially upward and downward movement of the pawl disc 140 about the top end of the boss 152. While the annular projection 151 impedes axial movement of the pawl disc 140, the annular projection 151 does not prevent axial movement of the pawl disc 140 due to the ability of the boss 152 to displace or flex radially inward. Specifically, the boss 152 is formed of a pair of fingers or members that extend axially upward from a base 153 of the coupling member 150. The pair of fingers flex inward toward one another to allow the top end of the boss 152 to displace and flex radially inward as the central opening 146 of the pawl disc 140 is moved axially upward or downward about and over the annular projection 151. After the pawl disc 140 is moved axially upward or downward about the annular projection 151, the pair of fingers resiliently flex outward to resume an un-deflected configuration. In operation, the central opening 146 of the pawl disc 140 is positioned above or below the annular projection 151, which supports and maintains the pawl disc 140 and/or knob 102 in either the engaged or disengaged position.

The knob 102 is coupled to the housing 120 by axially aligning the knob 102 and the housing 102 and by snapping the knob 102 atop a annular flange or rib 122 of the housing 120. Specifically, the inner wall or surface of the knob 102 includes a plurality of projections 104, or a radial lip, that snaps over the annular rib 122 of the housing 120 as the knob 102 is pressed and moved axially downward relative to the housing. The projections 104 of the knob 102 define an inner diameter that is smaller than an outer diameter of the annular rib 122. As such, in coupling the knob 102 with the housing 120, the inner wall of the knob 102 must flex outward to some degree and/or the housing 120 must flex inward to some degree to allow the knob 102 to be moved axially downward about and snap over the housing 120. After the knob 102 is moved axially downward, the projections 104 are positioned axially below the annular rib 122 of the housing 120. Due to the interference between the projections 104 and the annular rib 122, uncoupling of the knob 102 from the housing 120 via axially upward movement of the knob 102 is prevented or significantly impeded. Additional details of the coupling of the pawl disc 140, knob 102, and housing 120 are provided in U.S. patent application Ser. No. 14/991,788, filed Jan. 8, 2016, entitled "Integrated Closure Device Components and Methods," the entire disclosure of which is incorporated by reference herein.

Figure 3:
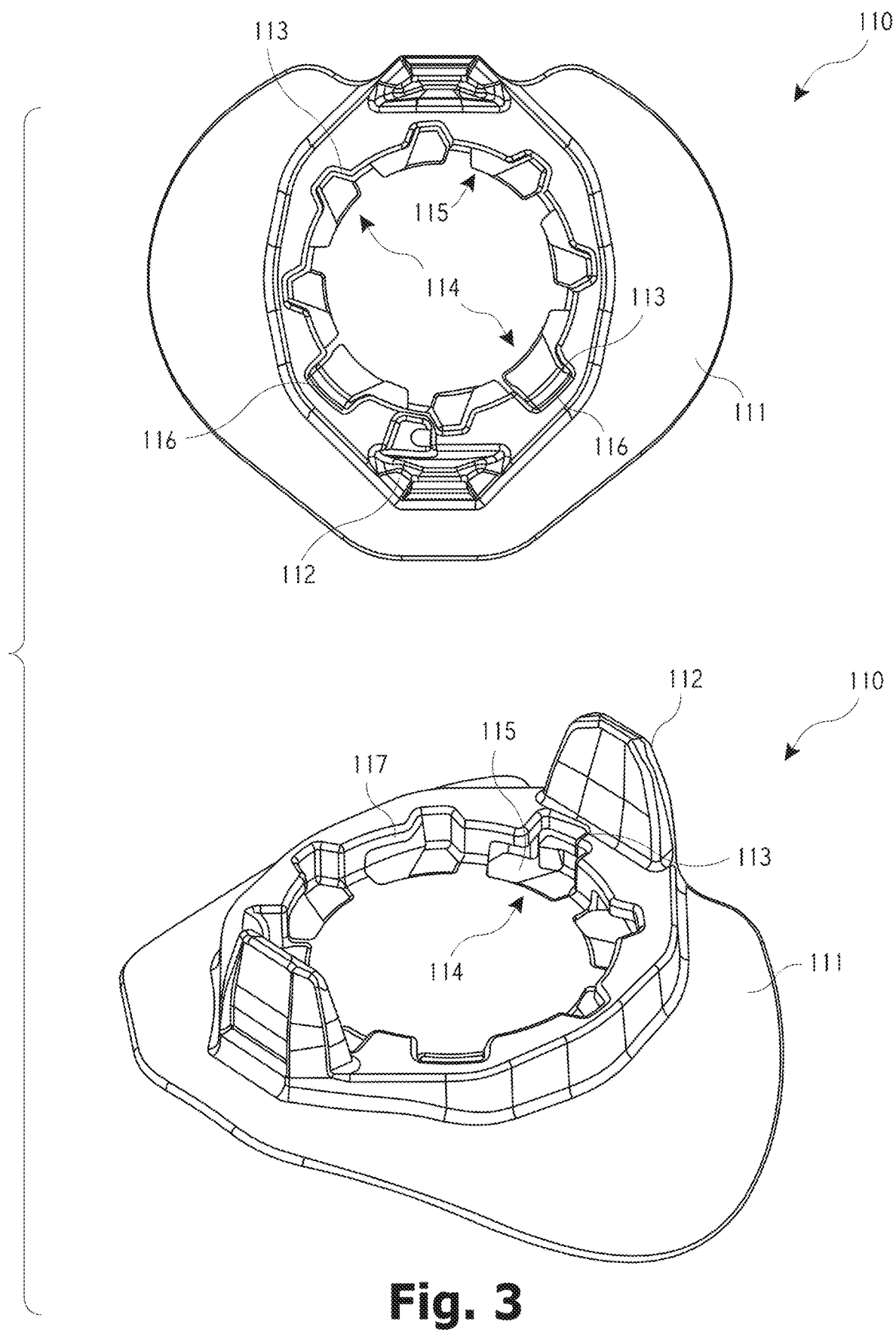
FIG. 3 illustrates a top view and a perspective view of a base member of the closure system of FIG. 1.

Referring now to FIG. 3, illustrated is a top view and a perspective view of the base member 110. The flange 111 that allows the base member 110 to be attached to the article is illustrated in greater detail, as are various other features of the base member 110. The base member 110 includes a pair of axially extending walls 112 that are positioned on opposite sides of the base member 110. When the closure system 100 is assembled, the walls 112 partially surround the housing 120 and knob 102 and may shield or protect the knob 102 from accidental contact with external objects. Shielding of the knob 102 by the walls 112 may prevent or limit accidental opening of the closure system 100 by preventing external objects from contacting the knob 102 and moving the knob 102 and pawl disc 140 axially upward into the disengaged position. The walls 112 may be positioned with respect to the knob 102 and/or article in a position where contact from external objects is most likely to occur or is anticipated. In some embodiments, the base member 110 may include no walls, one wall, or three or more walls as desired. The walls 112 are typically made of the same material as the base member 110, although other materials may be used for the walls 112.

The base member 110 defines an interior region and includes one or more recessed members or radially extending channels 114 (typically a plurality of recessed members/radially extending channels 114) that formed within a bottom inner surface of the base member 110 and on the exterior edge of the interior region. In the illustrated embodiment, the base member 110 includes eight recessed members or radially extending channels 114 (hereinafter recessed member(s) 114). Each recessed member 114 includes an axially extending opening 113 and a channel or groove 115 that extends circumferentially from the opening 113 and that is cut radially into the inner surface or wall of the base member 110. The channels 115 are formed into the inner wall of the base member 110 so that a material lip or protrusion 117 is formed above each of the channels 115. As described in greater detail below, the recessed members 114 are employed in attaching the housing 120 to the base member 110. One or more of the recessed members 114 may have a larger opening 116. In the illustrated embodiment, two of the recessed members 114 include larger openings 116. The larger openings 116 of the two recessed members 114 may be used in detaching the housing 120 from the base member 110.

Figure 4A:
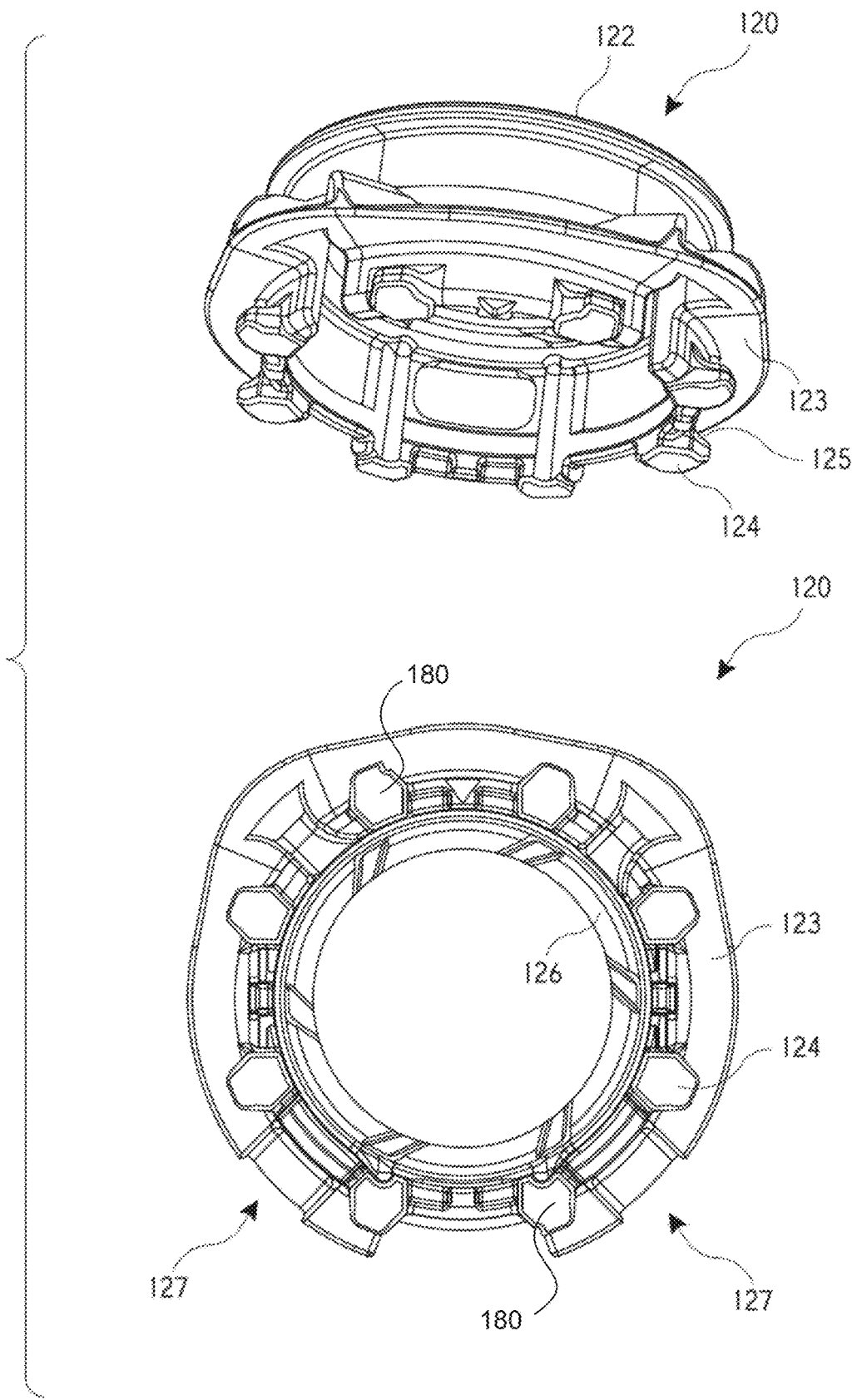
FIG. 4a illustrates a bottom view and a perspective view of a housing of the closure system of FIG. 1.

Referring now to FIG. 4a, illustrated is a bottom view and a perspective view of the housing 120. The annular rib 122 of the housing 120 is illustrated in greater detail, as are other features of the housing 120. In particular, one or more coupling tabs 124 extend axially downward from a bottom surface 123 of the housing 120. Each coupling tab 124 is configured to matingly engage with a recessed member 114 of the base member 110 and thus, the housing 120 typically includes a number of coupling tabs 124 that corresponds to the number of recessed members 114 of the base member 110 (e.g., eight coupling tabs 124). In addition, the coupling tabs 124 typically align with the recessed members 114 of the base member 110 to enable the housing 120 to be axially inserted within the interior region of the base member 110.

A distal end of the coupling tabs 124 extends radially outward so that a radially extending tab is formed in the distal end of the coupling tabs 124. An upper surface 125 of the radially extending tab is often chamfered, sloped, or arcuate in order to facilitate detachment of the housing 120 and base member 110 as described below. In some instances, an inner wall of the housing 120 includes a radially inward lip 126 that contacts an upper flange surface of the spool 130 as described in the '788 patent application incorporated by reference herein. The housing 120 also includes a port, channel, or recess 127 that is configured to be positioned axially above one of the larger openings 116 of the recessed member 114 in order to facilitate detachment of the housing 120 from the base member 110. More commonly, the housing 120 includes a pair of ports, channels, or recesses 127 within which a force application tool may be positioned to apply a force to the housing 120 that causes the housing to move axially out of the interior region of the base member 110.

Figure 5A:
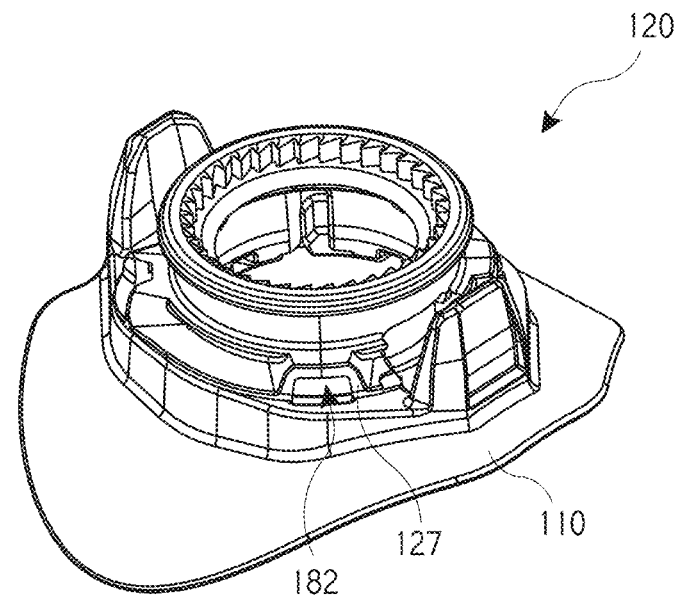
FIGS. 5a-b illustrate perspective views of the housing and the base member in an uncoupled state.
Figure 5B:
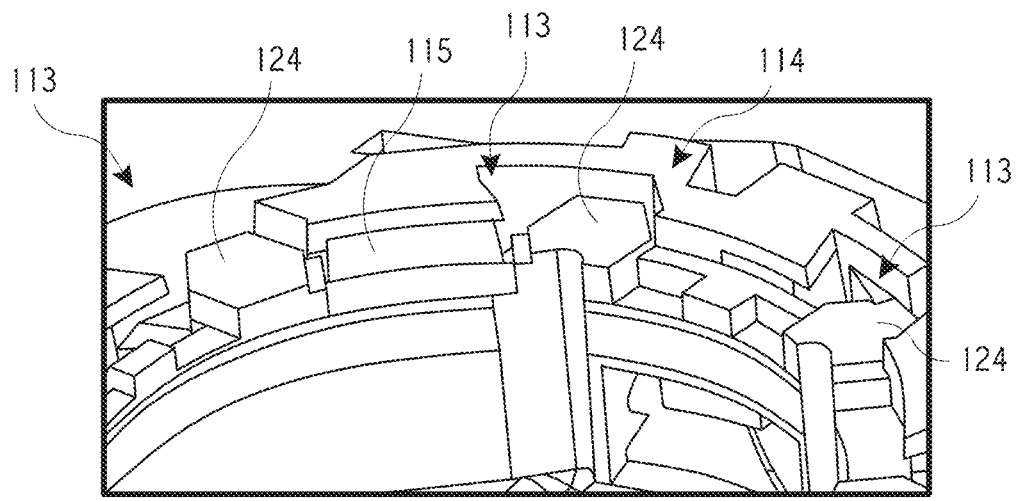

Referring now to FIGS. 5a and 5b, illustrated are perspective views of the housing 120 and the base member 110 in a first or uncoupled state. The first or uncoupled state means that the housing 120 and base member 110 are not secured or locked into engagement with one another. The first or uncoupled state may occur before the housing 120 is axially inserted within the interior region of the base member 110 or may occur after the housing is axially inserted within the interior region of the base member 110, but prior to rotating the housing 120 relative to the base member 110, which rotation secures or locks the housing 120 about the base member 110. In FIGS. 5a and 5b, the housing 120 is illustrated as being axially inserted within the interior region of the base member 110, but the housing 120 has not been rotated relative to the base member 110 and thus, the housing 120 and base member 110 are in the first or uncoupled state. In the first/uncoupled state, the housing 120 is coaxially aligned with the base member 110 and is rotationally aligned with the base member 110 so that each of the coupling tabs 124 are aligned with a corresponding recessed member 114 of the base member 110. With the coupling tabs 124 and recessed members 114 aligned, the housing 120 may be moved axially downward so that each coupling tab 124 is inserted within a respective opening 113 of the corresponding recessed member 114 as illustrated in FIGS. 5a and 5b. The enlarged cross-sectional perspective view of FIG. 5b illustrates three coupling tabs 124 positioned within an opening 113 of corresponding recessed members 114. In FIG. 5b, each coupling tab 124 is positioned on a right side of a corresponding channel 115 of the recess member 114. As described in greater detail below, a counterclockwise rotation of the housing 120 causes each coupling tab 124 to rotate into a corresponding channel 115 and to be positioned under a lip or protrusion of the base member 110, which secures the housing 120 to the base member 110. FIG. 5a illustrates that when the housing 120 is assembled with the base member 110, the recess 127 of the housing 120 forms a slot 182 within which the force application tool (e.g., screwdriver) can be positioned in order to detach the housing 120 from the base member 110.

Figure 6A:
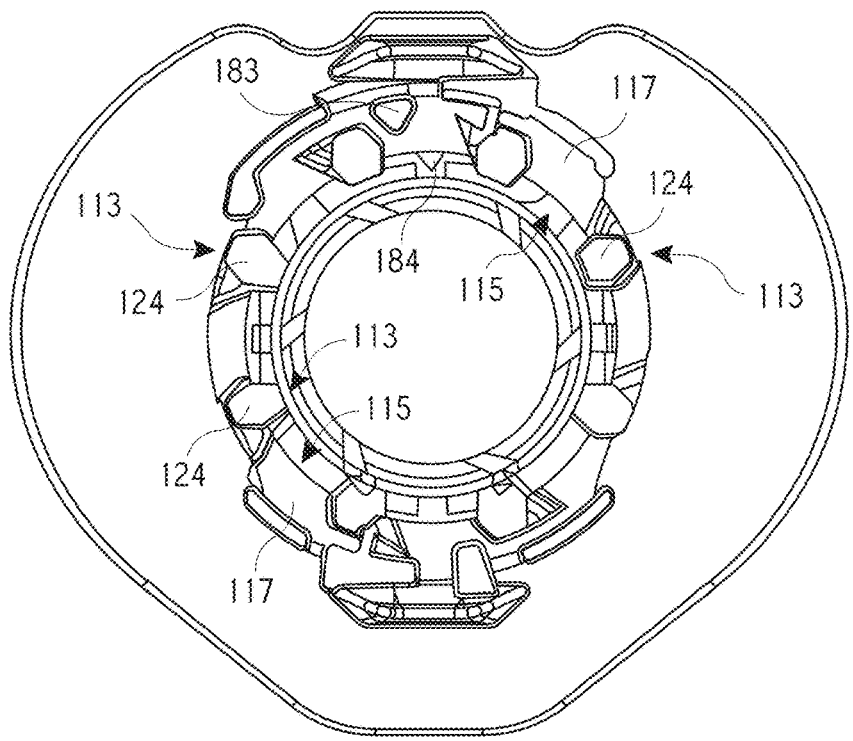
FIGS. 6a-b illustrate top views of the assembled housing and base member.
Figure 6B:
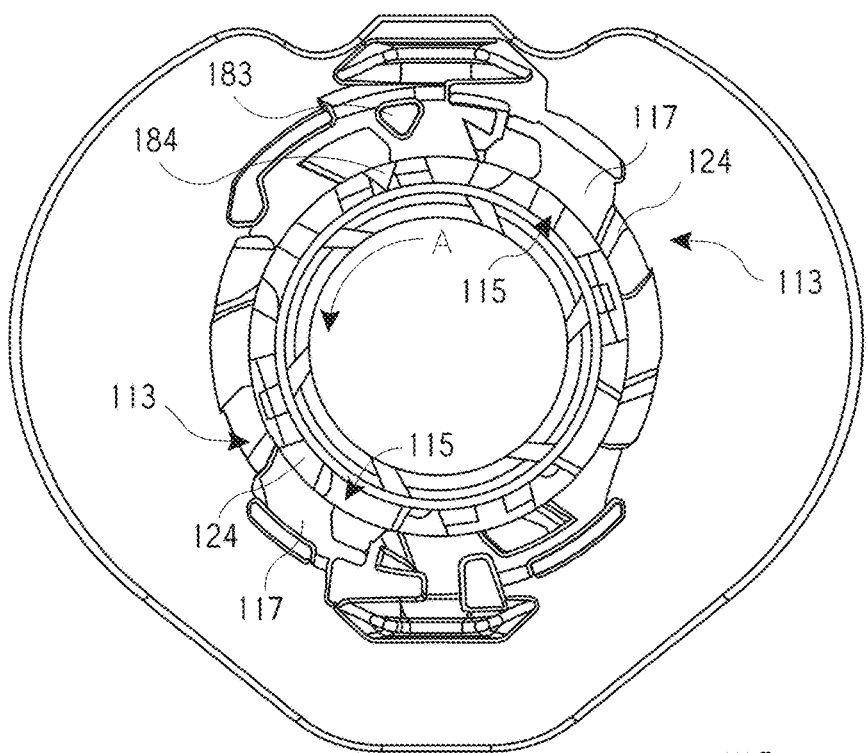

Referring now to FIGS. 6a and 6b, illustrated are top views of the assembled housing 120 and base member 110. The upper portion of the housing 120 is removed so that the coupling tabs 124 are visible in the figures. FIGS. 6a and 6b illustrate the assembly of the housing 120 and base member 110 in a manner that fixedly secures the housing 120 to the base member 110. FIG. 6a illustrates the housing 120 and the base member 110 in the first/uncoupled state of FIGS.

5a-b and FIG. 6b illustrates the housing 120 and base member 110 in a second or coupled state. As shown in FIG. 6a, each of the coupling tabs 124 (i.e., eight coupling tabs in the illustrated embodiment) are positioned within a corresponding opening 113 of the recessed members 114 (i.e., eight recessed members in the illustrated embodiment). The coupling tabs 124 are positioned within the corresponding openings 113 of the recessed members 114 by aligning the housing 120 and base member 110 and by axially inserting the housing 120 within the interior region of the base member 110. In order to fixedly attach the housing 120 to the base member 110, the housing is rotated with respect to the base member 110. FIG. 6b illustrates that the housing 120 is rotated in the direction of arrow A (e.g., counterclockwise direction), which causes the coupling tabs 124 to rotate out of the opening 113 and within a corresponding channel 115 of the recessed members 114. Rotation of the coupling tabs 124 within the channels 115 causes each of the coupling tabs 124 to be positioned axially under the material lip or protrusion 117 of the recessed members 114, which prevents the housing 120 from being moved axially upward and uncoupled from the base member 110.

A pair of alignment arrows or indicia, 183 and 184, that are positioned on the base member 110 and housing 120, respectively, may be used in properly aligning and attaching the housing 120 and base member 110. For example, the arrows or indicia, 183 and 184, may be used to properly orient the housing 120 about the base member 110 by positioning the indicia 184 of the housing in alignment with, or on the right side of, the indicia 183 of the base member 110. The housing 120 may then be rotated so that the indicia 184 of the housing 120 is on the left side of, or in alignment with, the indicia 183 of the base member 110. In this manner, an assembler of the closure system 100 may ensure that the base member 110 and housing 120 are properly aligned and/or fixedly attached. In some instances, the knob 102 may be used to both insert the housing 120 within the base member 110 and to rotate the housing 120 into locked engagement with the base member 110.

Figure 4B:
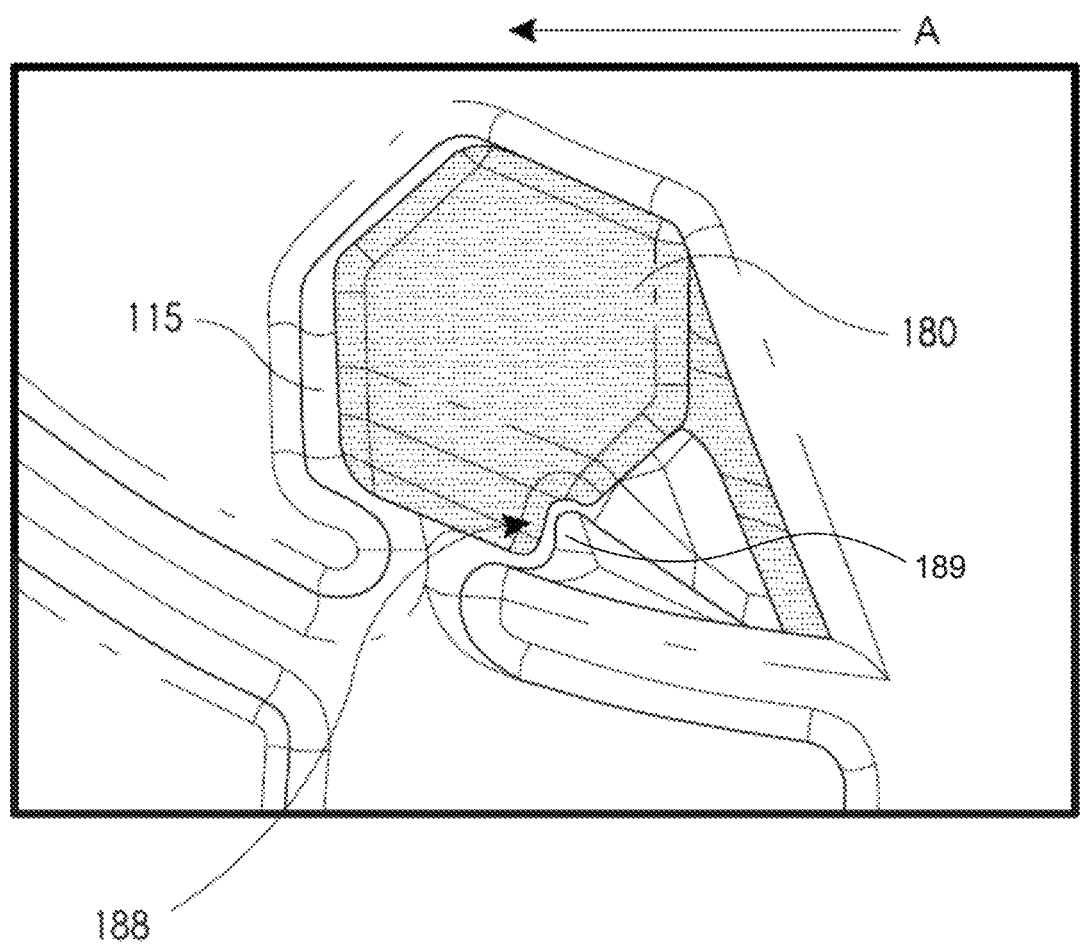
FIG. 4b illustrates a mechanical engagement of a coupling tab of a housing and a channel of a base member.

The coupling tabs 124 may be secured within the channels 115 of the recessed members 114 via mechanical engagement of one or more of the coupling tabs 124 with the channels 115. Specifically, as shown in FIG. 4a, one or more of the coupling tabs (referred to by reference numeral 180) may be designed to lock into engagement with the corresponding channel. In the illustrated embodiment, two of the coupling tabs 180 are designed to lockingly engage with the corresponding channels 115 of the base member 110, although more or fewer coupling tabs may be employed to lock or secure the housing 120 within the interior region of the base member 110. FIG. 4b illustrates the locking engagement of a coupling tab 180 and a corresponding channel 115 in greater detail. Specifically, FIG. 4b illustrates an anti-rotation member, barb, or protrusion 189 that is formed in the channel 115 that mechanically engages with a distal lip or edge 188 of the coupling tab 180 to prevent a counter rotation of the housing 120 relative to the base member 110, which secures the housing 120 within the interior region of the base member 110.

The distal lip or edge 188 may be curved upward slightly to increase the locking engagement of the coupling tab 180 and channel 115. In some instance, the distal lip or edge 188 may have a slight recess that aligns and engages with a similar recess on the anti-rotation barb or protrusion 189 of the channel 115. The coupling tab 180 may be a flexible, resilient, or compliant material that snaps into engagement with the anti-rotation barb or protrusion 189. The anti-rotation barb or protrusion 189 may cause the coupling tab 180, or the distal lip or edge 188, to flex axially downward as the coupling tab 180 is rotated into position within the channel 115 and over the anti-rotation barb or protrusion 189. Arrow A in FIG. 4b illustrates the direction the coupling tab 180 rotates with respect to the channel 115. Because the anti-rotation barb or protrusion 189 is positioned in the path of rotation of the coupling tab 180, the coupling tab 180 and/or the distal lip or edge 188 is forced to rotate over the anti-rotation barb or protrusion 189, which may cause the coupling tab 180 and/or the distal lip or edge 188 to flex or displace axially downward to some degree. After the distal lip or edge 188 snaps into engagement with the anti-rotation barb or protrusion 189, the coupling tab 180 is locked in position so that counter-rotation of the coupling tab 180 (i.e., rotation that would disengage the coupling tab 180 and channel 115) is prevented. The housing 120 is locked into engagement with the base member 110 due to the locking engagement of the coupling tab 180 and channel 115.

Figure 7:
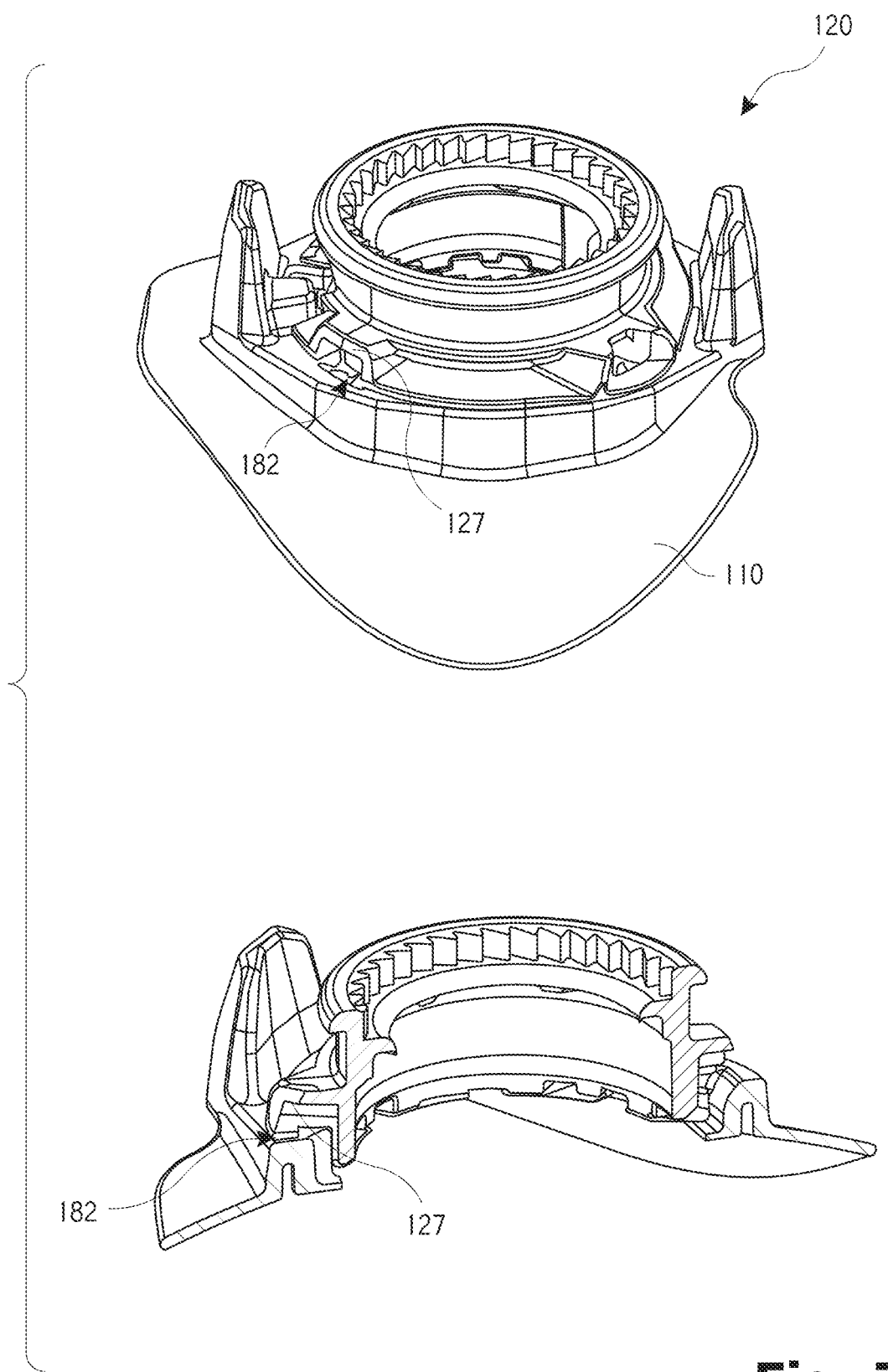
FIG. 7 illustrates the housing and the base member in a coupled state.

Referring now to FIG. 7, illustrated are the housing 120 and base member 110 in the second/coupled state with the coupling tabs 124 fixedly secured within the channels 115 of the recessed members 114 as described above. With the housing 120 and base member 110 in the second/coupled state, the housing 120 is essentially locked or secured to the base member 110 so that uncoupling or detachment of these components is substantially prevented. The use of the term "substantially prevented" in describing the attachment of the housing 120 and base member 110 implies that the base member 110 and housing 120 may be uncoupled from one another, but that under normal conditions these components will not detach or uncouple from one another. Stated differently, the use of the term "substantially prevented" in describing the attachment of the housing 120 and base member 110 implies that the components may only be detached due to substantial forces being imparted on the closure system 100 or under controlled situations as described below.

FIG. 7 illustrates that in the second/coupled state, the recess 127 of the housing 120 forms a slot 182. While FIG. 7 illustrates only a single slot 182, it should be realized that in the instant embodiment, the housing 120 includes two recesses 127, which would form two slots 182. The second slot (not shown) is positioned on an opposite side of the assembled components and thus, is not visible in FIG. 7, although the second slot may be positioned elsewhere as desired. The housing 120 may include more or fewer recesses 127 as desired. As briefly described above, the slots 182 are employed for detaching the housing 120 from the base member 110. Detachment of the components is achieved by inserting a force application tool (e.g., a slotted screwdriver, bar, or other tool) into the slot 182 and applying an axially upward force on the housing 120. A pair of tools (not shown) are typically used with each tool being inserted within one of the slots 182. In other instances, a single tool could be used sequentially with each slot 182 to apply the axially upward force. The slots 182 enable the tools to be used as levers in applying the axially upward force on the housing 120. With the application of a sufficient axial upward force, the housing 120 detaches from the base member 110 due to the coupling tabs 124 being forced out of the channels 115 of the recessed members 114. The detachment of the housing 120 from the base member 110 is achieved without requiring a rotation of the housing 120 relative to the base member 110. Rather, the housing 120 is axially moveable relative to the base member 110 to detach the housing from the base member.

In forcing the coupling tabs 124 out of the channels 115, the bottom end of the housing 120 and/or the bottom end of the base member 110 may flex, deflect, bend, or displace to some degree. The chamfered, sloped, or arcuate upper surface 125 of the coupling tabs 124 may aid in detachment of the housing 120 from the base member 110 by allowing the coupling tabs 124 to slide out of engagement with the channels 115. In some embodiments, the channels 115 may have corresponding chamfers, slopes, or arcuate surfaces that also aid in detachment of the housing 120 and base member 110.

The housing 120 and base member 110 may also be detached due to a substantial force being imparted on the closure system 100. For example, if the knob 102 or housing 120 are contacted by an external object with sufficient force, an axially upward force may be imparted on the housing that causes the coupling tabs 124 to be displaced from within the channels 115. The housing 120 and other components of the closure system 100 (i.e., the knob 102, pawl disc 140, spool 130, and coupling member 150) may then be detached from the base member 110. Detachment of the housing 120 and base member 110 in this manner may prevent the housing 120, base member 110, knob 102, or other components from breaking due to extreme forces being imparted on the closure system 100. The detached housing 120 may be reassembled with the base member 110 in the manner described above. If the housing 120 or another component breaks due to the imparted force, the housing 120, spool 130, pawl disc 140, and/or coupling member 150 may be replaced and reattached to the base member 110 as described above.

In some embodiments, the base member 110 may be configured so that the housing 120 is only coupleable with the base member in one of a few defined orientations. In such embodiments, the housing 120 must be aligned with the base member 110 in one of the defined orientations in order to couple the housing 120 with the base member 110. If the housing 120 is not properly aligned with the base member 110, such as by axially inserting housing 120 within the interior region of the base member 110 in an orientation other than one of the few defined orientations, the housing 120 may be prevented from rotating into engagement with the base member 110. FIGS. 7*a-d* illustrate an embodiment in which the base member 110 is configured so that the housing 120 may be coupled with the base member 110 in one of a few defined orientations and so that the housing 120 cannot be rotated into engagement with the base member 110 unless a proper alignment of the components is achieved.

Figure 7A:
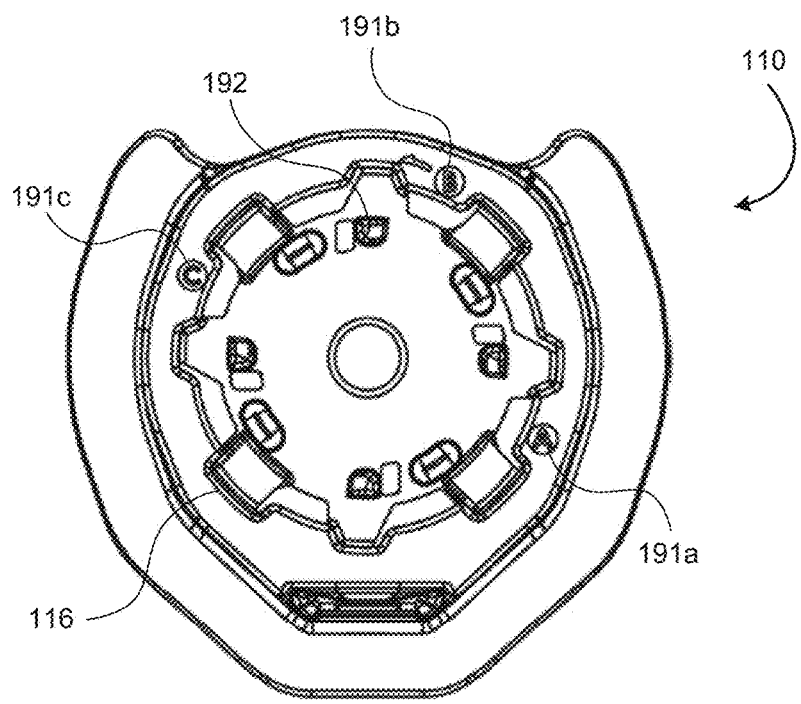
FIGS. 7a-d illustrate an embodiment of the base member in which the housing is only coupleable with the base member in one of a few defined orientations.

Specifically, FIG. 7*a* illustrates the base member 110 including axially protruding member 192 that are configured to contact a bottom surface of the housing 120 and prevent the housing 120 from being fully inserted within the interior region of the base member 110 if the housing 120 is not properly aligned with the base member 110. FIG. 7*a* illustrates the base member 110 includes 4 equally spaced axially protruding members 192, although more or fewer of such members may be employed as desired. To enable the housing 120 to be fully inserted within the interior region of the base member 110 when the housing 120 is properly aligned with the base member 110, the bottom surface of the housing 120 includes circumferentially extending slots (not shown) within which the axially protruding members 192 are positioned. The circumferentially extending slots are wide enough and long enough that the axially protruding members 192 remain within the slots as the housing 120 is rotated into engagement with the base member 110.

The use of the axially protruding members 192 and the circumferentially extending slots allows the housing 120 to be coupled with the base member 110 in multiple different orientations, but prevents the housing 120 from being coupled with the base member 110 in an orientation that is not intended. The coupling of the housing 120 with the base member 110 in this manner allows a single base member 110 to be used to attach the closure system 100 to an article in various different orientations relative to the article and/or an opening of the article that will be closed and tightened by the closure system 100. For example, in footwear applications, the coupling of the base member 110 and the housing 120 in the different orientations allows the same base member 110 to be used to position the closure system 100 on the medial side of the footwear's upper, on the lateral side of the footwear's upper, and on the tongue portion of the footwear. In conventional systems, different base members are typically required to position the closure devices on the opposing sides of the footwear and/or on the footwear's tongue.

To aid an installer in properly aligning the housing 120 and the base member 110, the base member 110 includes indicia, 191*a-c*, that aids the installer in identifying when the housing 120 is properly aligned. The indicia, 191*a-c*, also aides the installer in determine how to couple the housing 120 with the base member 110 so that a desired orientation of the housing 120 and base member 110 is achieved. In addition, since the housing 120 is coupled with the base member 110 in multiple different orientations, the base member 110 includes additional openings 116 that facilitate in detachment of the housing 120 from the base member 110 as described above. In particular, the use of the additional openings 116 ensures that a pair of openings 116 will align with the pair of recesses 127 of the housing 120 regardless of the coupled orientation of the housing 120 and base member 110. FIG. 7*a* illustrates the base member 110 includes 4 equally spaced openings 116, although more or fewer openings 116 may be employed as desired.

Figure 7B:
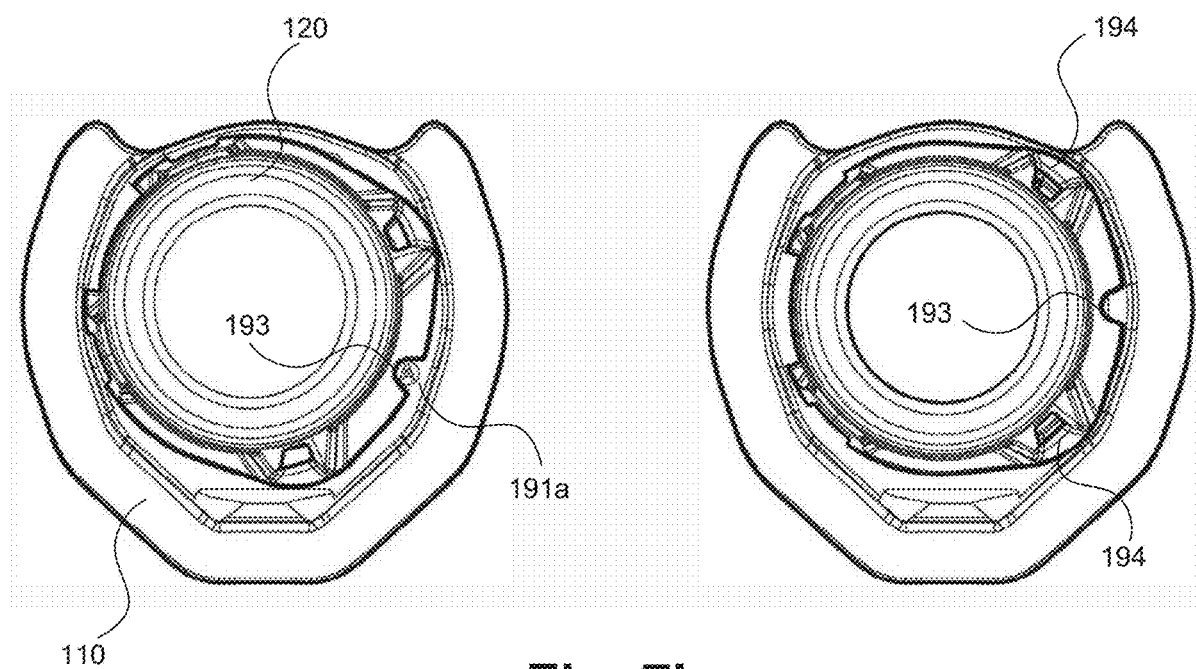
Figure 7C:
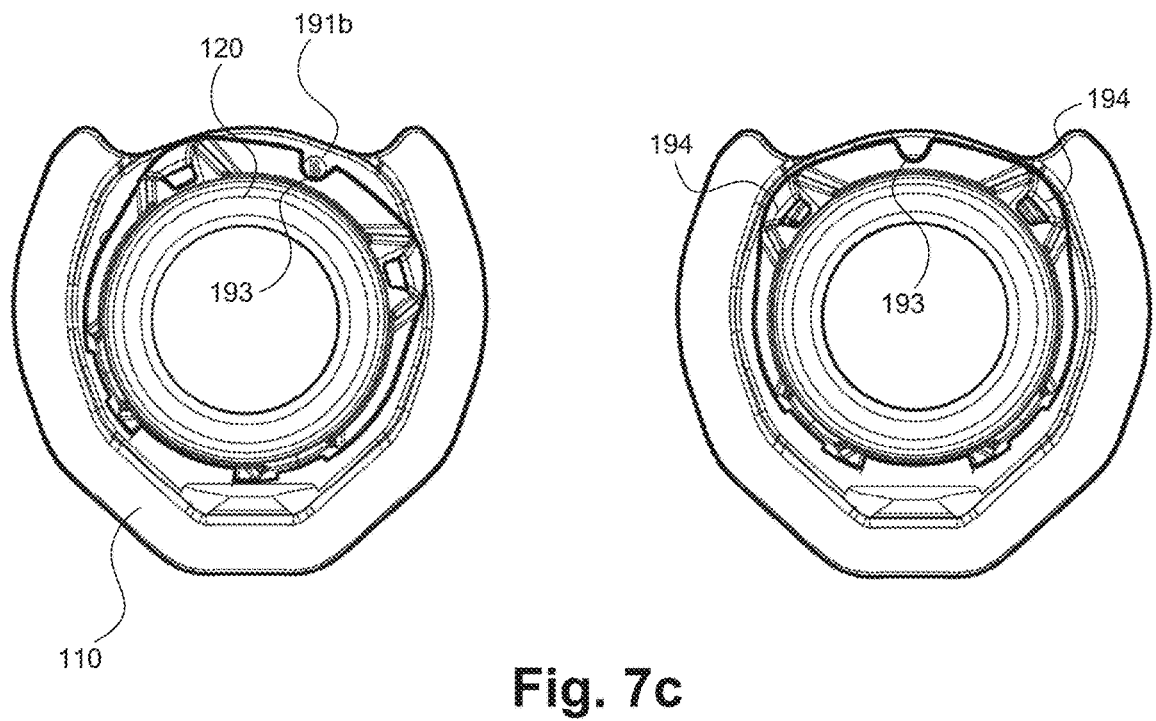
Figure 7D:
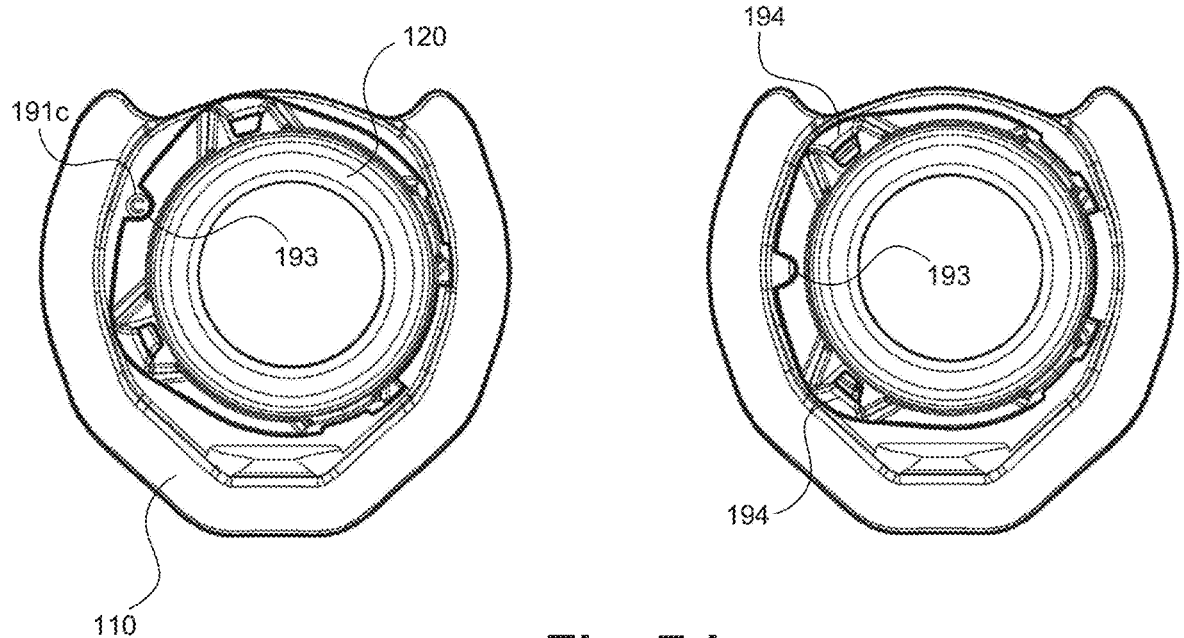

FIGS. 7*b-d* illustrate three different coupled orientations of the housing 120 and base member 110 that may be achieved due to the design of the base member 110 of FIG. 7*a*. In FIG. 7*b*, the left hand image shows the housing 120 axially inserted within the interior region of the base member 110 in the first/uncoupled state. A first indicia 191*a* of the base member 110 is visible through a window 193 or cutout portion of the housing 120, which aids an installer in recognizing that the housing 120 is properly aligned with the base member 110 and further recognizing that coupling of the housing 120 and base member 110 will results in a first defined orientation of the housing 120 about the base member 110. The right hand image of FIG. 7*b* illustrates the housing 120 and base member 110 in the second/coupled state in which the housing 120 has been rotated into engagement with the base member and in which the housing 120 is positioned in the first defined orientation relative to the base member 110. In the first defined orientation, a pair of lace ports 194 of the housing 120 face the right hand side of the base member 110 as illustrated.

In FIG. 7*c*, the left hand image shows the housing 120 axially inserted within the interior region of the base member 110 in the first/uncoupled state. A second indicia 191*b* of the base member 110 is visible through the window 193 of the housing 120, which aids the installer in recognizing that the housing 120 is properly aligned with the base member 110 and further recognizing that coupling of the housing 120 and base member 110 will results in a second defined orientation of the housing 120 about the base member 110. The right hand image of FIG. 7*c* illustrates the housing 120 and base member 110 in the second/coupled state in which the housing 120 has been rotated into engagement with the base member and in which the housing 120 is positioned in the second defined orientation relative to the base member 110. In the second defined orientation, the pair of lace ports 194 of the housing 120 face forward relative to the base member 110 as illustrated.

In FIG. 7d, the left hand image shows the housing 120 axially inserted within the interior region of the base member 110 in the first/uncoupled state. A third indicia 191c of the base member 110 is visible through the window 193 of the housing 120, which aids the installer in recognizing that the housing 120 is properly aligned with the base member 110 and further recognizing that coupling of the housing 120 and base member 110 will results in a third defined orientation of the housing 120 about the base member 110. The right hand image of FIG. 7d illustrates the housing 120 and base member 110 in the second/coupled state in which the housing 120 has been rotated into engagement with the base member and in which the housing 120 is positioned in the third defined orientation relative to the base member 110. In the third defined orientation, the pair of lace ports 194 face the left hand side of the base member 110 as illustrated.

Although not illustrated, the housing 120 may similarly be coupled with the base member 110 so that the pair of lace ports 194 face backward relative to the base member 110. The housing 120 is not coupleable with the base member 110 in an orientation other than those described. For example, the housing 120 cannot be coupled with the base member 110 so that the pair of lace ports 194 are positioned between the left hand side of the base member and the front of the base member.

Figure 8A:
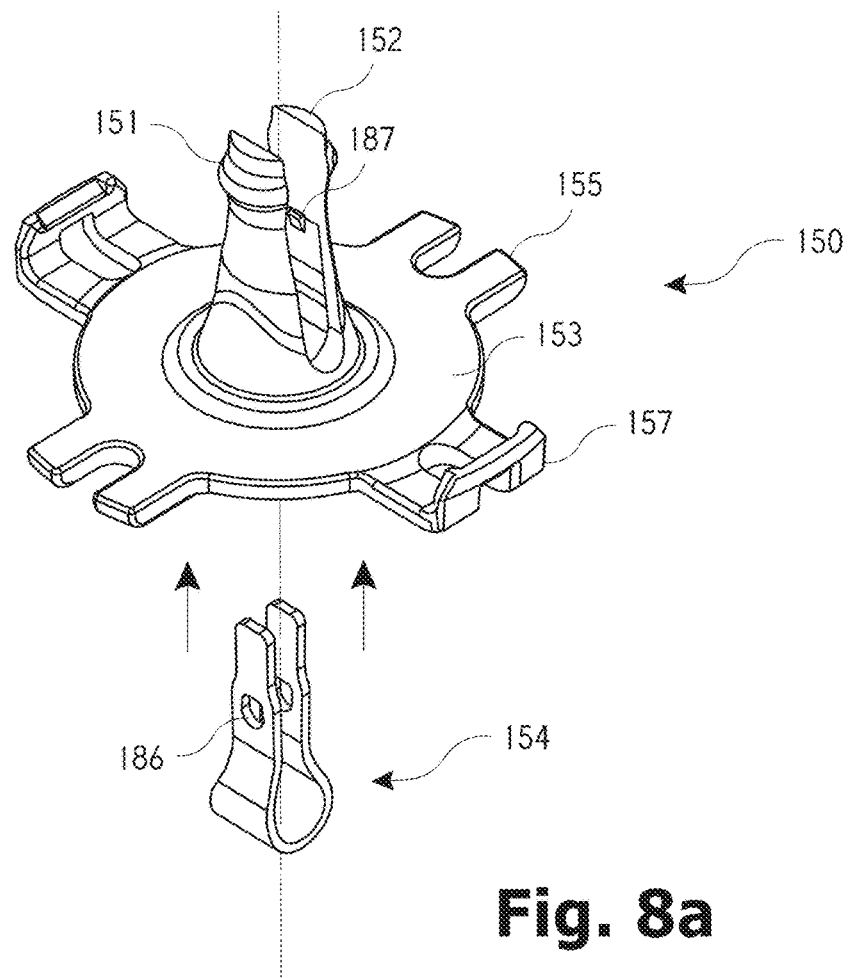
FIGS. 8a-b illustrate perspective views of a coupling member and a reinforcement spring.
Figure 8B:
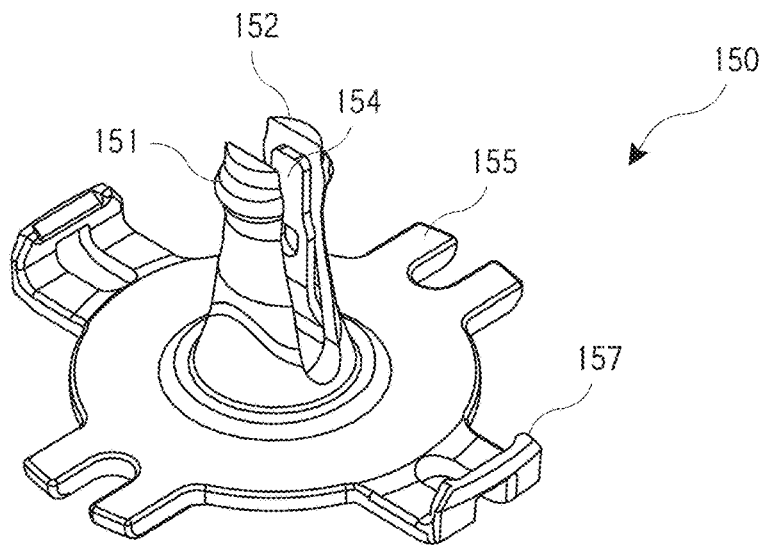

Referring now to FIGS. 8a and 8b, illustrated are perspective views of the coupling member 150 and a reinforcement spring that is employed to strengthen and reinforce the pair of fingers of the top end 152 of the coupling member 150. FIG. 8a illustrates an exploded perspective view of the coupling member 150 and reinforcement spring 154, while FIG. 8b illustrate an assembled perspective view of the components. The reinforcement spring 154 is inserted axially within an axially extending gap between the pair of fingers of the top end 152 of the coupling member 150. The reinforcement spring 154 is made of a flexible and resilient material, such as spring steel or a metal free (e.g., PEAK) material. The reinforcement spring 154 aids in resiliently deflecting the pair of fingers of the top end 152 of the coupling member 150 as the pawl disc 140 is moved axially upward and downward about the annular projection 151. The reinforcement spring 154 may also stiffen the pair of fingers and prevent the pair of fingers from plastically deforming due to extended use of the closure system 100. As illustrated, the reinforcement spring 154 has a U-shaped configuration.

The reinforcement spring 154 includes an aperture 186 that engages with a small projection 187 that is positioned on the inner surface of the pair of fingers. Engagement of the aperture 186 and projections 187 locks or retains the reinforcement spring 154 in position relative to the pair of fingers. The reinforcement spring 154 may be inserted axially through a bottom aperture of the coupling member 150 to position the reinforcement spring 154 between the pair of fingers.

Figure 9:
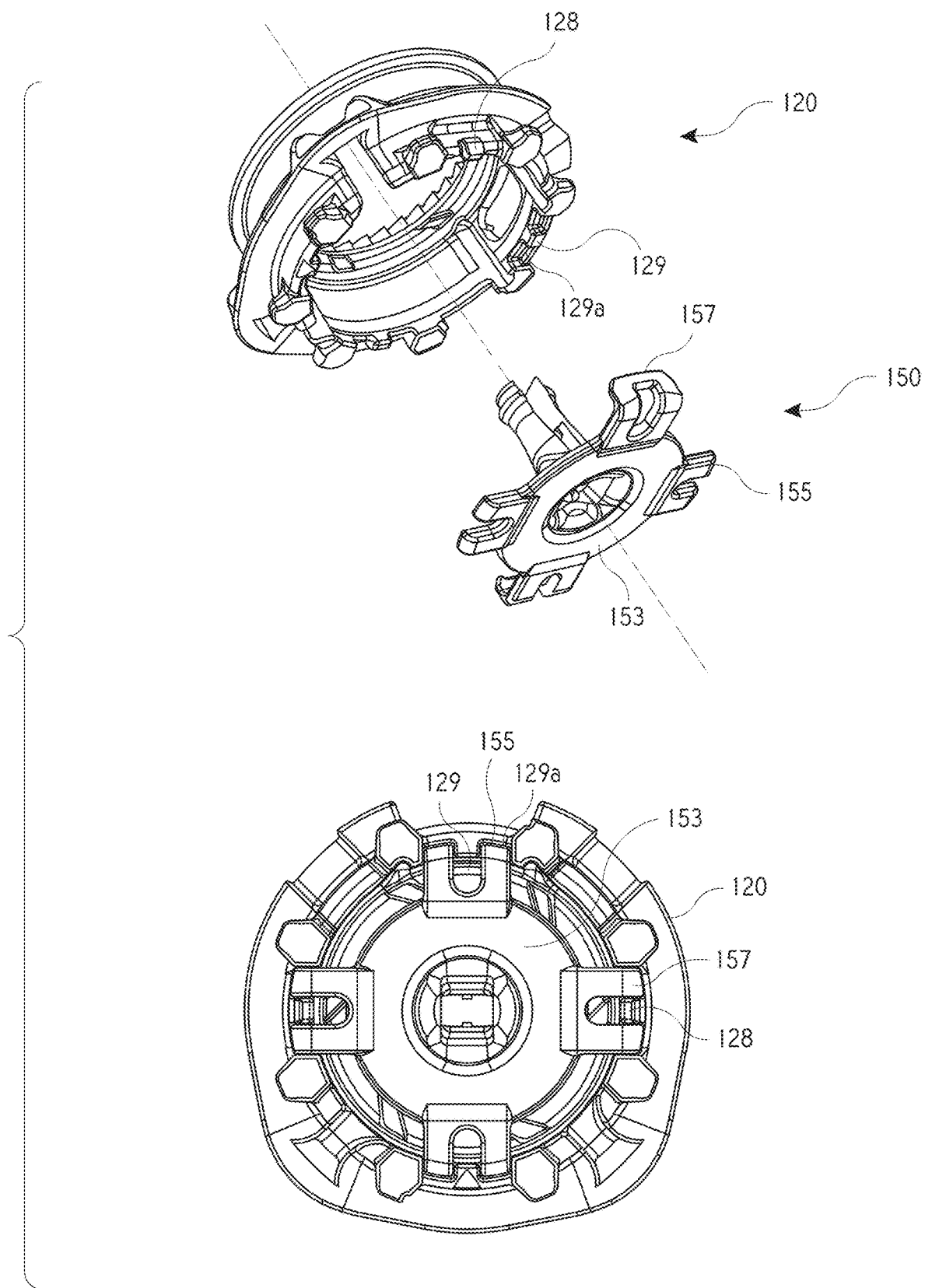
FIG. 9 illustrates a bottom view and a bottom exploded perspective view of the coupling member and housing.

Referring now to FIG. 9, illustrated is a bottom exploded perspective view of the coupling member 150 and housing 120 and a bottom view of the coupling member 150 and housing 120 in an assembled configuration. FIG. 9 illustrates how the coupling member 150 is attached to the housing 120. As shown in FIG. 9, and illustrated in greater detail in FIGS. 8a-b, the base 153 of the coupling member 150 includes several radial extending arms, tabs, or projections, 155 and 157, that orient and couple the coupling member 150 with the housing 120. Specifically, the coupling member 150 includes a pair of first radially extending arms or tabs 155 (hereinafter first radial tabs) and a pair of second radially extending arms or tabs 157 (hereinafter second radial tabs). The first radial tabs 155 extend radially outward with a gap or space between opposing sides of the radial tabs. The second radial tabs 157 also extend radially outward, but the second radial tabs 157 include an upward turned lip. The second radial tabs 157 may also include a radially extending space or gap between the opposing side of the radial tabs 157. The radially extending space or gap may extend from near the central boss and to the upward turned lip.

The radial tabs, 155 and 157, are configured to couple with corresponding features of the bottom end or surface of the housing 120. For example, the first radial tabs 155 are configured for positioning within a recess 129a of the bottom surface of the housing 120. A small boss or projection 129 may be positioned within the gap or space between the opposing sides of the first radial tab 155 when the radial tab is positioned within the recess 129a. The second radial tabs 157 are likewise positioned about the side of the housing 120 within a recess of the bottom surface of the housing 120. The upward turned lip of the second radial tabs 157 is configured to flex, bend, or curve around or over a bottom edge of the housing 120 to secure the coupling member 150 in position relative to the housing. A small boss or projection 128 may be positioned within the gap or space of the second radial tabs 157. When the second radial tabs 157 are positioned about the side of the housing 120, an upper edge of each upward turned lip is positioned axially above the respective boss or projection 128, which helps secure the coupling member 150 to the bottom end of the housing 120.

Figure 10:
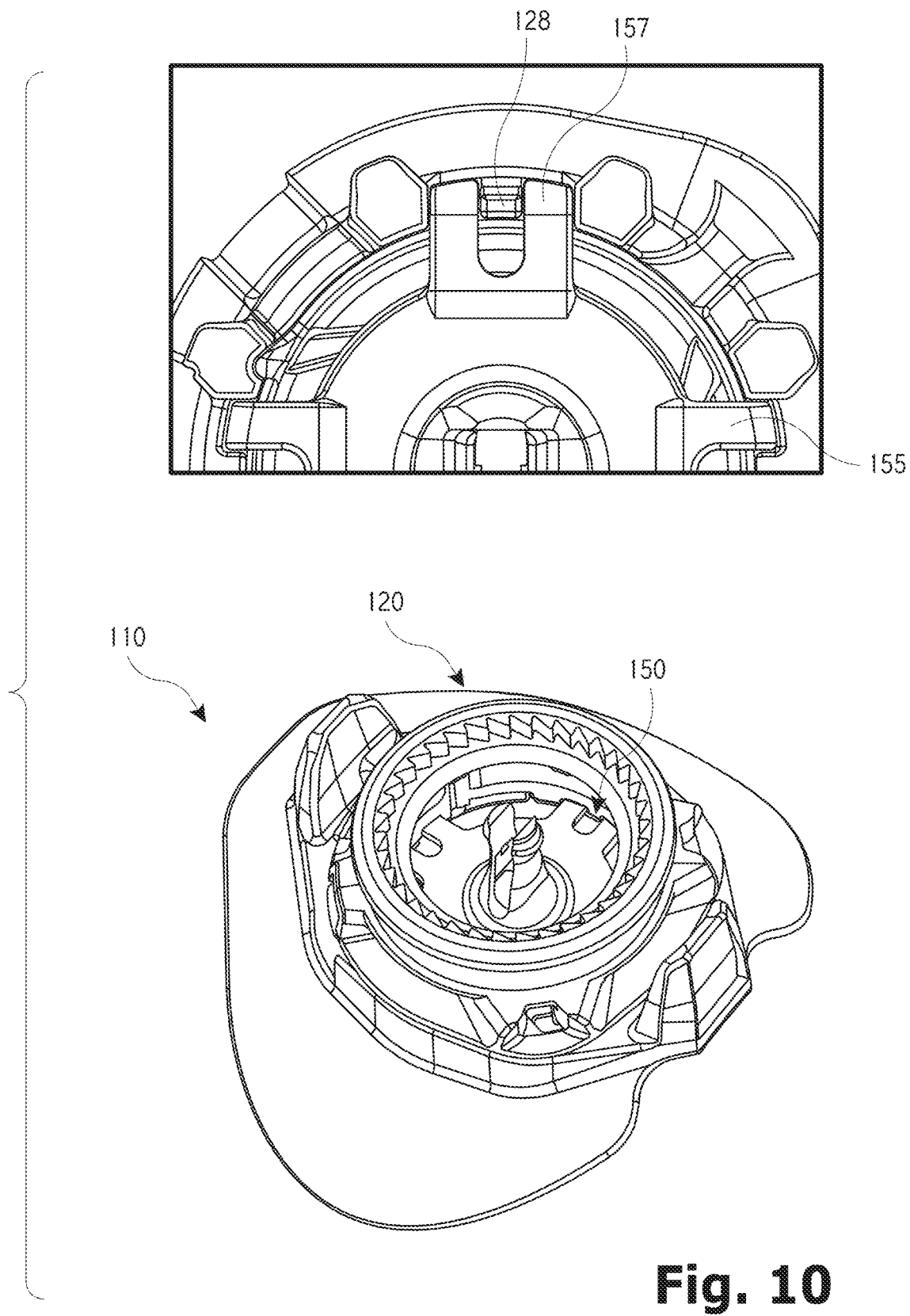
FIG. 10 illustrates a detailed view of a radial tab coupled about the side of the housing and also illustrates a perspective view of the assembled base member and housing.

The second radial tabs 157 may be detached from the side of the housing 120 by flexing or bending the upward turned lip radially outward while applying an axial downward force to the coupling member 120. Uncoupling of the second radial tabs 157 from the housing 120 causes the coupling member 150 to uncouple from the housing 120, which allows the coupling member 150 to be removed from the closure system 100. FIG. 10 illustrates the coupling of the second radial tabs 157 about the side of the housing in greater detail. FIG. 10 also provide a perspective view of the assembled coupling member 150, housing 120, and base member 110 with the spool 130 removed from the assembly so that the base 153 of the coupling member and a portion of the first and second radial tabs are visible. Detachment of the coupling member 150 from the housing 120 requires detachment of the housing 120 from the base member 110.

Figure 11:
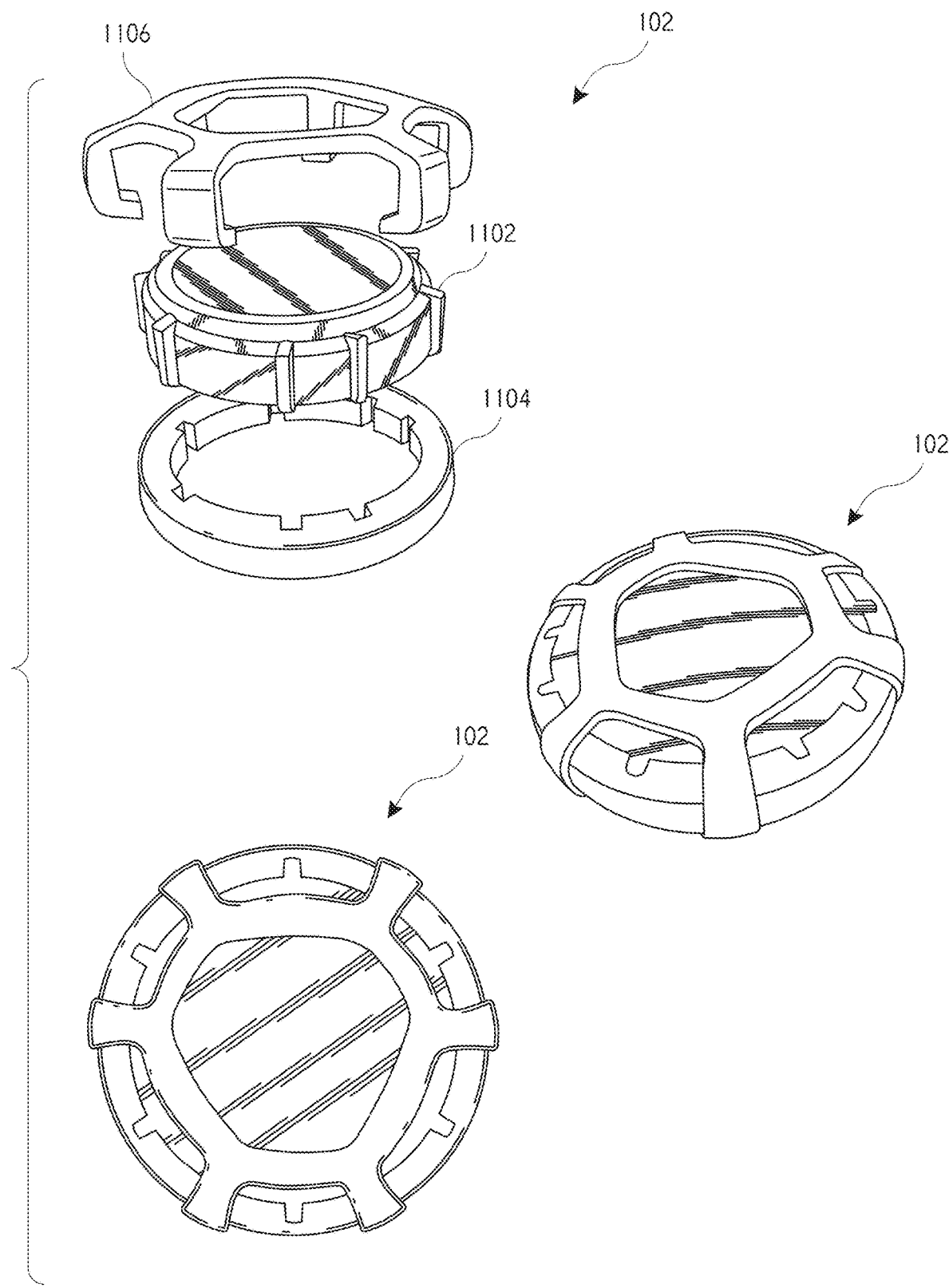
FIG. 11 illustrates an exploded perspective view and a top view of a knob.

Referring now to FIG. 11, illustrated is an exploded perspective view and a top view of the knob 102. The exploded perspective view of the knob 102 illustrates several components of the knob 102 in an unassembled state while the top view illustrates the components in an assembled state. The knob 102 includes or is formed of three components: a main body 1102, a first over mold 1104, and a second over mold 1106. The first and second over molds, 1104 and 1106, are materials that aid a user in gripping the knob 1102. The first over mold 1104 may be an annular ring that is disposed about the outer perimeter of the main body 1102. The second over mold 1106 may be in the form of a cage having an annular ring that is positioned atop a portion of the main body 1102 and fingers or projections that wrap around and over the side of the main body 1102 and first over mold 1104. The second over mold 1106 may help prevent peeling or delamination of the main body 1102 and first over mold 1104. The first and second over molds, 1104 and 1106, may be different materials that have different frictional characteristics to aid the user in gripping the knob 102. In a specific embodiment, the main body 1102 and/or second over mold 1106 may be a polycarbonate material while the first over mold 1104 may be a thermoplastic elastomer (TPE) material.

In a specific embodiment, each of the three components is formed in a separate mold process, which is typically an injection mold process. For example, the main body 1102 may be formed via injection molding and then the first over mold 1104 may be injection molded atop the main body 1102. The second over mold 1106 may then be injection molded atop the main body 1102 and the first over mold 1104. The mold process may be used to provide an aesthetic appeal, or may be used to provide other desired properties, such as an increased grip surface. When the three components are injection molded in the manner described above, the three components form a unitary knob 102 having an enhanced grip surface.

Referring now to FIGS. 12a-20, illustrated are lace coupling components that aid in fixedly attaching the tension member or lace to the spool 130 and closure system 100. The coupling components are separate from the lace and frictionally engages with a distal end of the lace so that the coupling component are removably fixed about the distal end of the lace. As described in greater detail below, and in the '788 patent application incorporated by reference herein, the housing 120 includes lace entrance and exit ports that align with a coupling feature (e.g., lumen) of the spool 130. The alignment of the housing's lace ports and the spool's lumen allows the lace to be inserted through the housing and spool for coupling or attachment of the lace with the spool. The coupling components illustrated in FIGS. 12a-20, greatly simplify the process of attaching the lace to the spool 130.

Each of the of the coupling components of FIGS. 12a-20 includes a main body and at least one aperture through which the lace is inserted to frictionally engage the lace with the coupling component. In most embodiments, the main body of the coupling component includes at least two apertures through which the lace is inserted. The coupling components are configures so that the lace frictionally engages with the coupling component without require a knot to be tied in the lace and without require any other alteration of the lace. The coupling component frictionally may engage with the distal end of the lace so that no trimming or cutting of the lace is required after the coupling component is secured to the lace. The aperture(s) of the coupling component have a diameter that is slightly larger than a diameter of the tension member. The diameter of the aperture(s) may be between 2 and 20% larger than the diameter of the lace, and more commonly between 5 and 15% larger, or between 5 and 10% larger. In some embodiments, the coupling component is configured to frictionally engage with opposing ends of the lace so that the coupling component is fixedly secured to both ends of the lace.

Figure 12A:
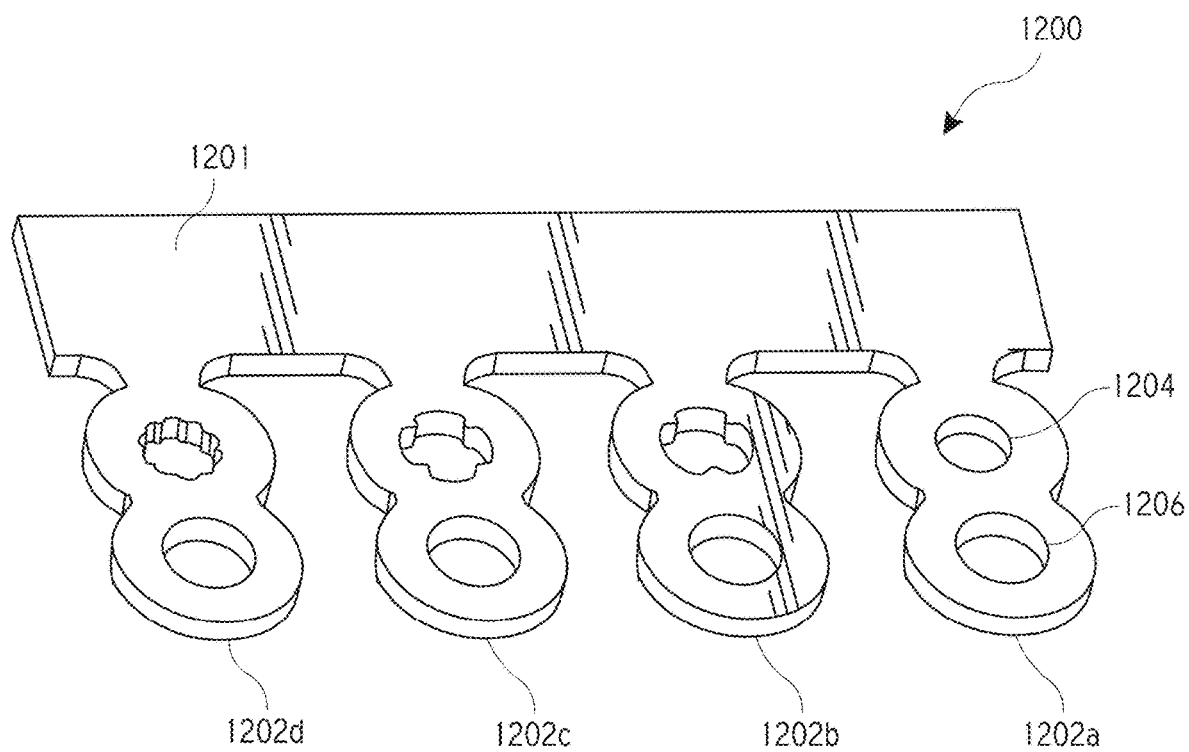
FIGS. 12a-b illustrate a lace coupling component.
Figure 12B:
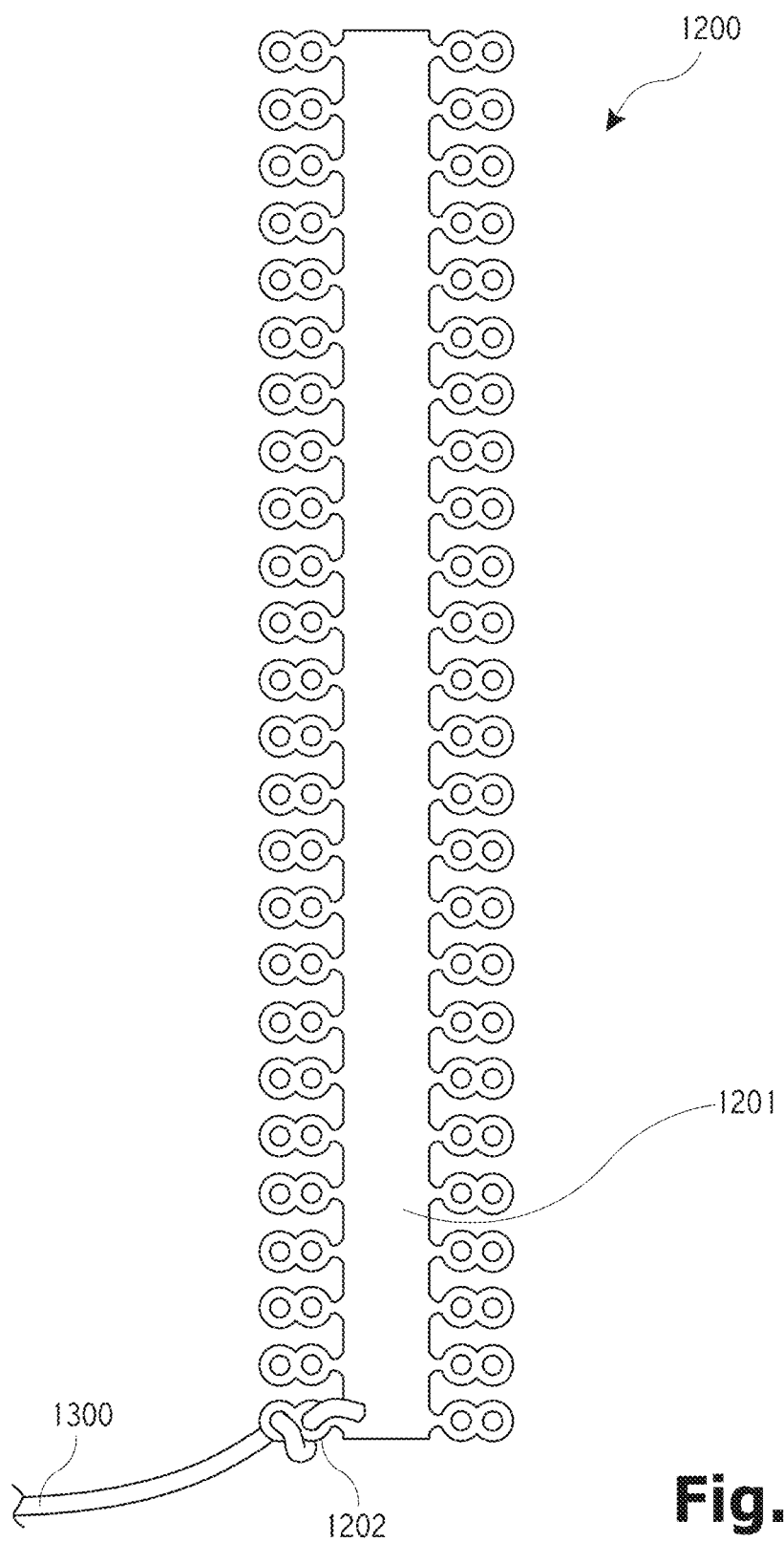

Referring to FIGS. 12a and 12b, illustrated is an embodiment of a lace coupling component 1200. FIG. 12a shows four component variations, 1202a-d, of the lace coupling component 1200. The configuration of each of the components, 1202a-d, is substantially similar except for the configuration of the apertures. Each of the components, 1202a-d, is formed of a main body that may be in the shape of a "FIG. 8". In other instances, the components, 1202a-d, may have an oval, rectangular, or circular shape. Each of the components, 1202a-d, includes a pair of apertures, 1204 and 1206, through which a lace 1300 is inserted. The apertures, 1204 and 1206, are typically sized slightly larger than the lace 1300 to enable easy insertion of the lace 1300 through the apertures. The components, 1202a-d, are typically made of a material that is flexible enough to enable easy insertion of the lace 1300, yet stiff enough that the lace is firmly secured about the component 1202 after being inserted through or otherwise coupled with the component. Exemplary materials include most metal materials, and more commonly non-corrosive metals such as stainless steel or aluminum. Other suitable materials include fiber reinforced plastic, fiberglass, carbon fiber, elastomers, and the like.

In a first component variation 1202a, the pair of apertures, 1204 and 1206, have circular configurations. The pair of apertures, 1204 and 1206, may have similar sized diameters, or more commonly different sized diameters where one of the apertures (e.g., 1204) is smaller than the other aperture. The different diameter sizes of the pair of apertures, 1204 and 1206, may aid in cinching or securing the lace 1300 within the component 1202a. In a second component variation 1202b, one or both of the apertures include small radial projections. The radial projections may bite or grip into the lace 1300 to help secure the lace in position about the component 1202b. In a third component variation 1202c, one or both of the apertures include slightly larger radial projections so that a cross section of the aperture(s) has a roughly T-shaped configuration. In a fourth component variation 1202d, one or both of the apertures includes numerous radial projections so that an inner surface of the aperture(s) has a toothed configuration. The specific component that is employed among the component variations, 1202a-d, may be selected based on the lace 1300 material and other factors of the closure system 100. FIGS. 12a-b illustrate that the component 1202 may be formed from a main body 1201. A small material bridge may connect the component 1202 with the main body 1201. The material bridge may be easily severed or broken to remove an individual component 1202 from the main body 1201. An advantage of employing the main body 1201 is ease of handling by a user.

Figure 13A:
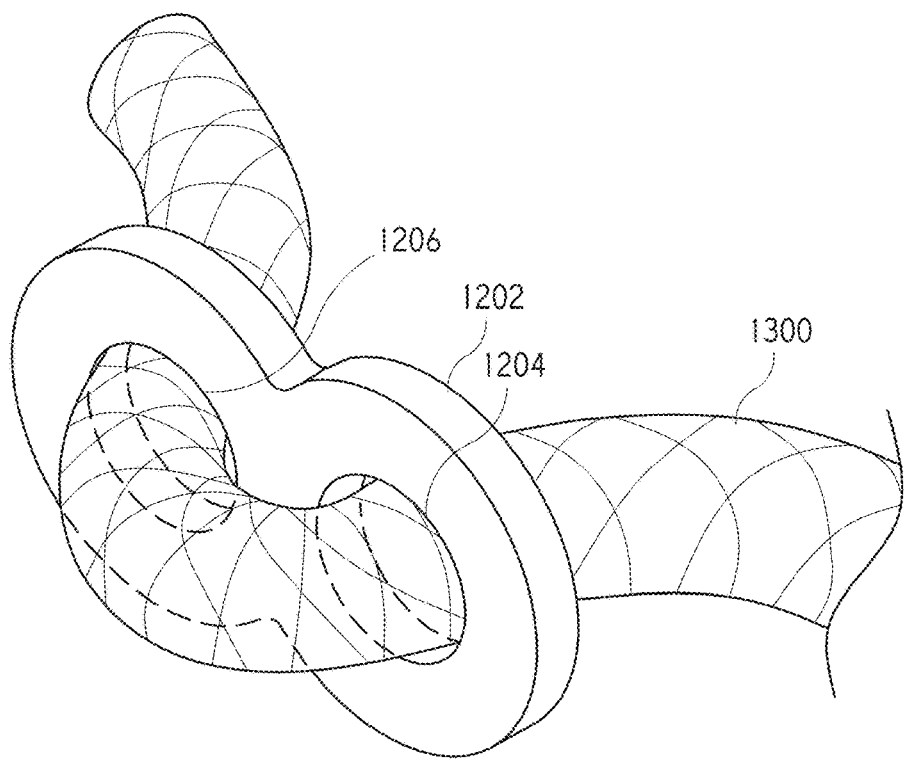
FIGS. 13a-b illustrate various configurations of coupling a lace with the lace coupling component of FIGS. 12a-b.
Figure 13B:
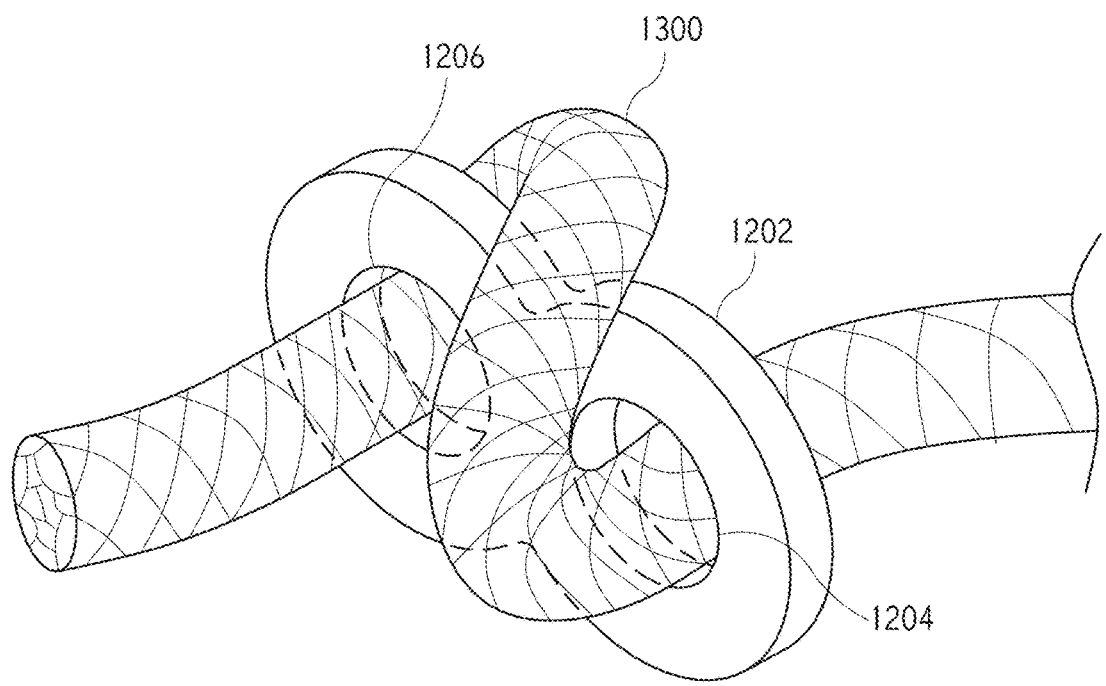

Referring to FIGS. 13a and 13b, illustrated are various configuration of inserting the lace 1300 through the apertures, 1204 and 1206, of the component 1202. In FIG. 13a, the lace 1300 is inserted through the first aperture 1204 and then immediately looped over the midsection of the component 1202 before being inserted through the second aperture 1206. In FIG. 13b, the lace 1300 is inserted through the first aperture 1204 and is then wrapped around the component 1202 in a helical manner before being inserted through the second aperture 1206. Other variations of inserting the lace 1300 through the apertures, 1204 and 1206, may likewise be employed.

Figure 14:
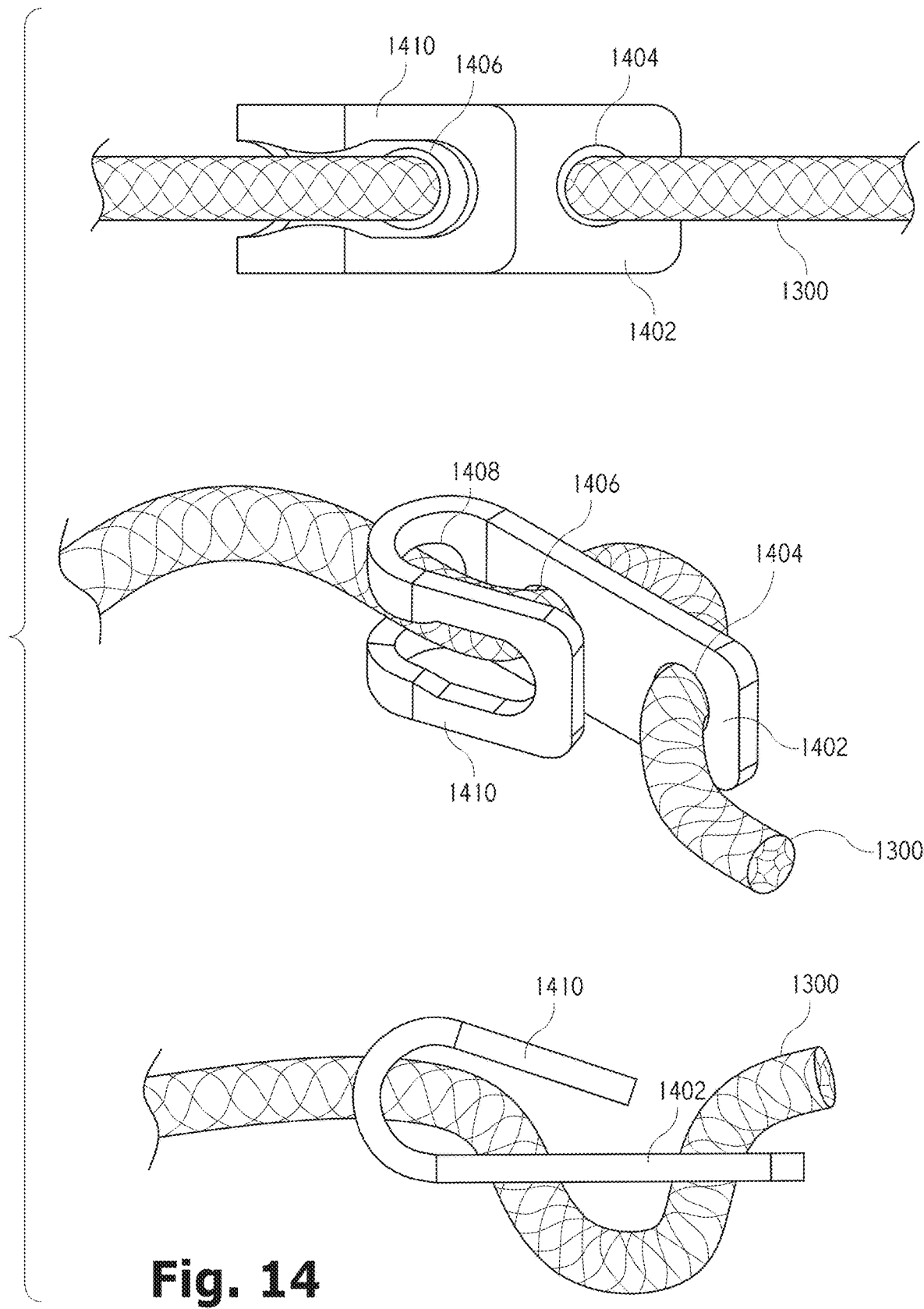
FIG. 14 illustrates another embodiment of a coupling component.

Referring now to FIG. 14, illustrated is another embodiment of a component 1402 that may be used in securing the lace 1300 to the spool 130 of the closure system 100. The component 1402 has a roughly rectangular shape with a hooked or bent distal end 1410. The component 1402 include a first aperture 1404 and a second aperture 1406 through which the lace 1300 is inserted as previously described. The hooked end 1410 includes a slot or channel 1408 through which the lace 1300 is also inserted. The slot or channel 1408 may include wide and narrow portions to enable insertion of the lace 1300 and crimping or pinching of the lace. For example, the lace 1300 may be inserted through a wide portion of the channel 1408 and threaded through the first and second apertures, 1404 and 1406. The lace 1300 may then be moved or pulled downward into one of the narrow portions of the slot 1408 so that the lace 1300 is pinched or squeezed in the narrow portion of the slot 1408, which may aid in securing the lace 1300 within or about the component 1402. The hooked end 1410 may also aid in retaining the component 1402 within the lumen of the spool 130.

Figure 15A:
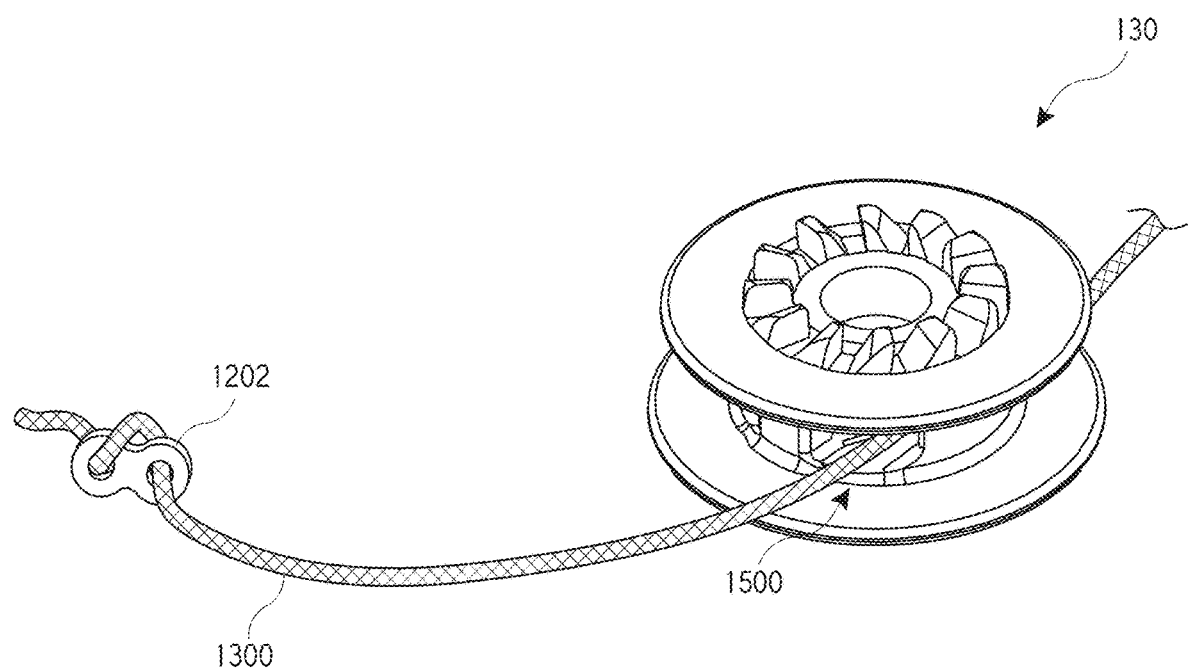
FIGS. 15a-f illustrate the components of FIGS. 12a-14 being employed to secure a lace within a spool of a closure system.
Figure 15B:
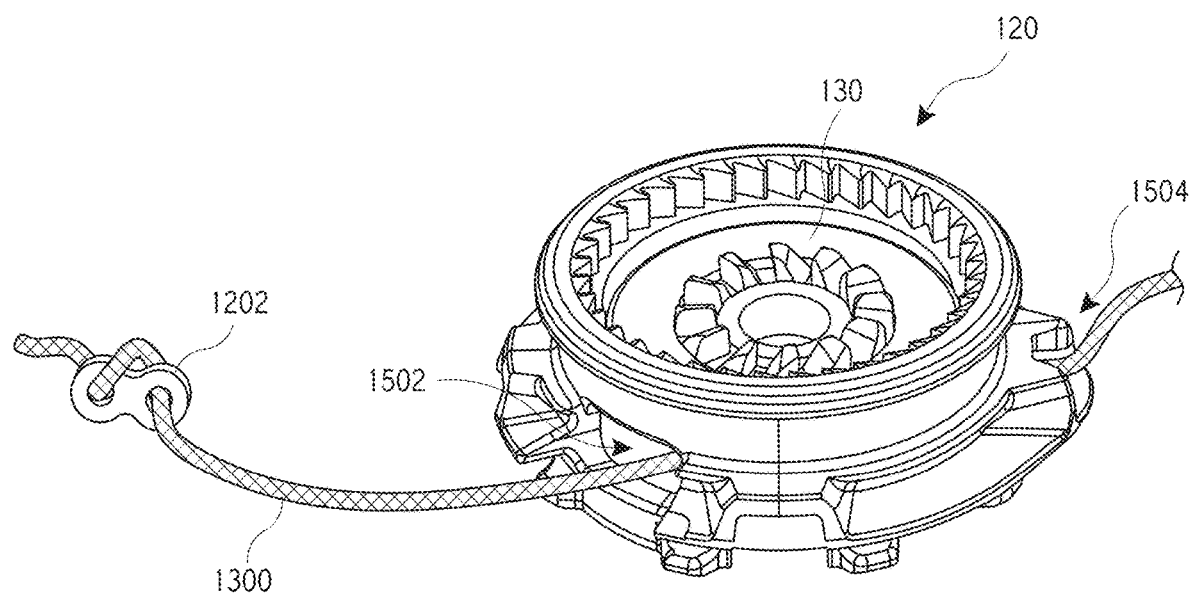
Figure 15C:
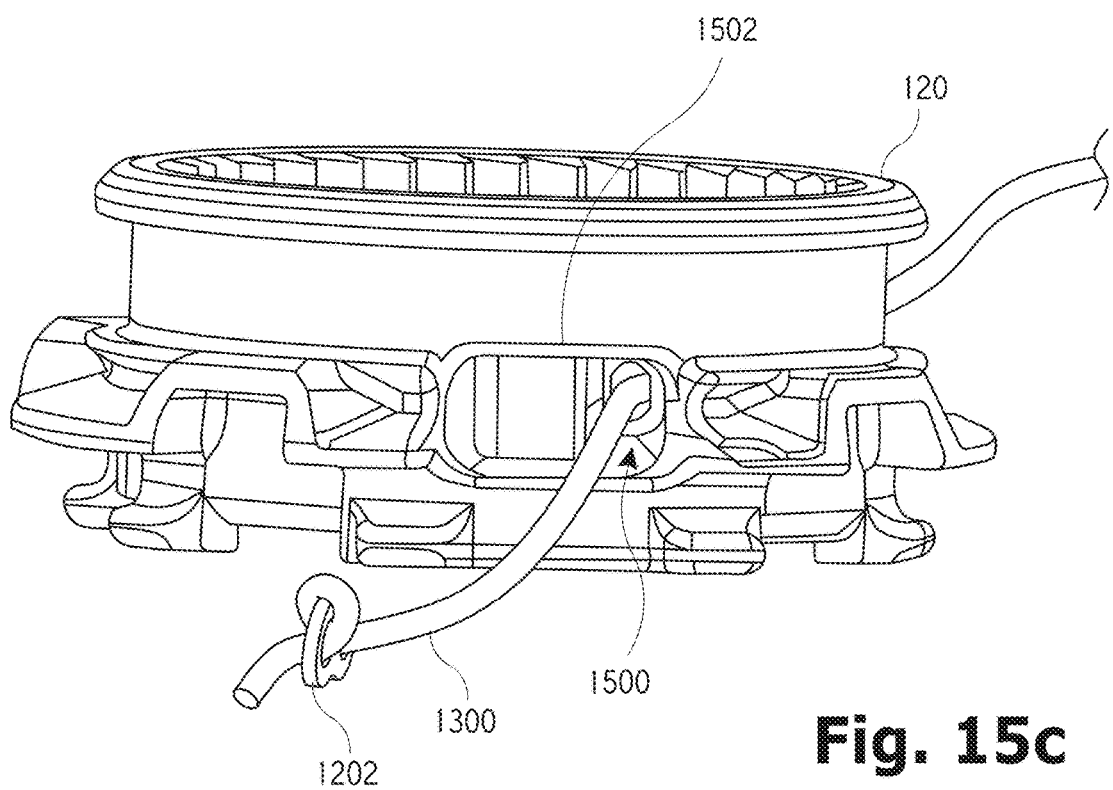
Figure 15D:
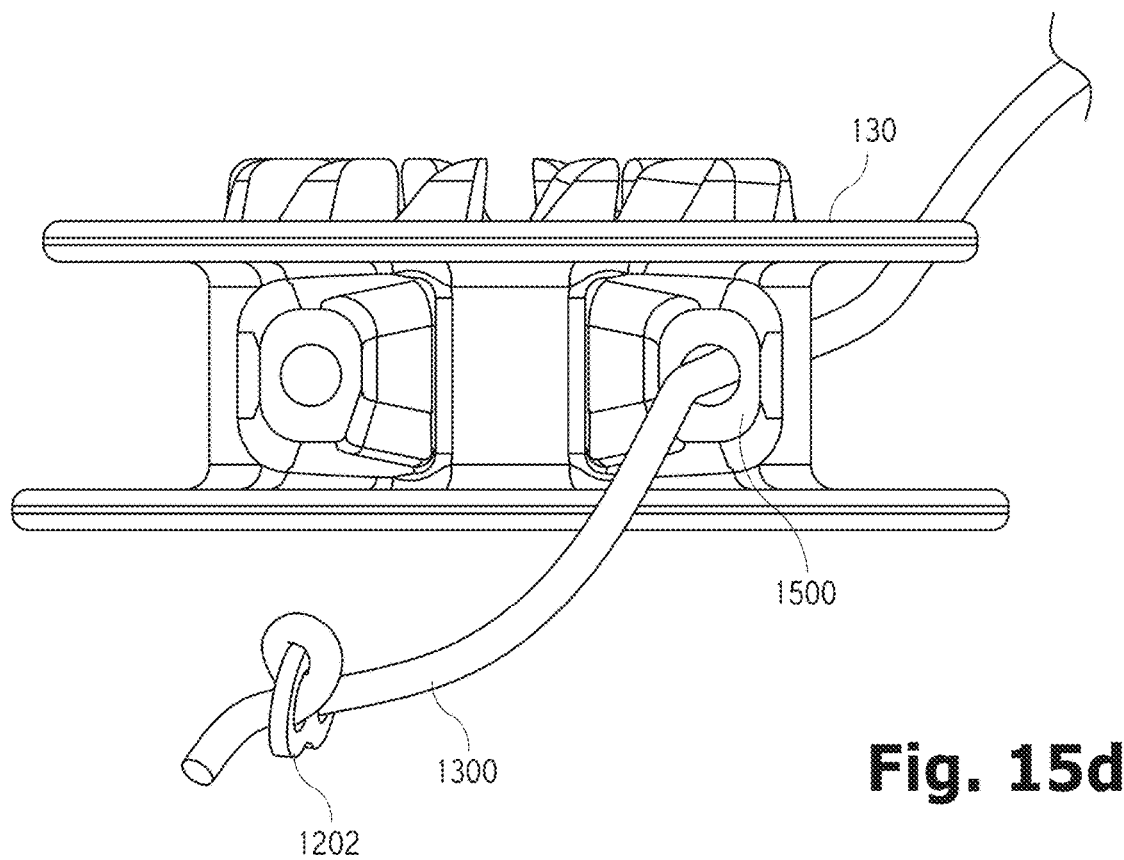

Referring now to FIGS. 15*a-f*, illustrated is a representation of the components of FIGS. 12*a*-14 being employed to secure the lace 1300 within the spool 130 of the closure system 100. Specifically, the component 1202 is illustrated in securing the lace 1300 within the coupling feature of the spool 130 in order to operationally attach or couple the lace 1300 to the closure system 100. The coupling feature is a channel or lumen 1500 (hereinafter lumen 1500) that extends through a centrally positioned cylindrical wall or body member of the spool 130. FIG. 15*a* illustrates the lace 1300 attached to the component 1202 as described above. The lace 1300 is inserted through the lumen 1500 of the spool 130. FIG. 15*b* illustrates the spool 130 positioned within the interior region of the housing 120 and aligned with the housing 120 so that the lumen 1500 of the spool 130 is aligned with an entrance port 1504 and an exit port 1502 of the housing 120. Alignment of the spool's lumen 1500 with the housing entrance port 1504 and exit port 1502 allows the lace 1300 to be inserted through the entrance port 1504, through the lumen 1500 of the spool 130, and through the exit port 1502. In this manner the lace 1300 is positioned on opposing sides of the spool 130 and housing 120 and may be operationally coupled with the spool 130. Operationally coupling the lace 1300 with the spool 130 means that the lace 1300 is attached to the spool 130 in a manner so that rotation of the spool 130 within the housing 120 in the tightening direction causes the lace 1300 to be wound about the central portion or channel 132 of the spool 130, which effects tensioning of the lace 1300. FIGS. 15*c* and 15*d* illustrate the insertion of the lace 1300 through the spool's lumen 1500 and the alignment of the spool's lumen 1500 and the housing's entrance and exit ports, 1504 and 1502, in greater detail.

Figure 15E:
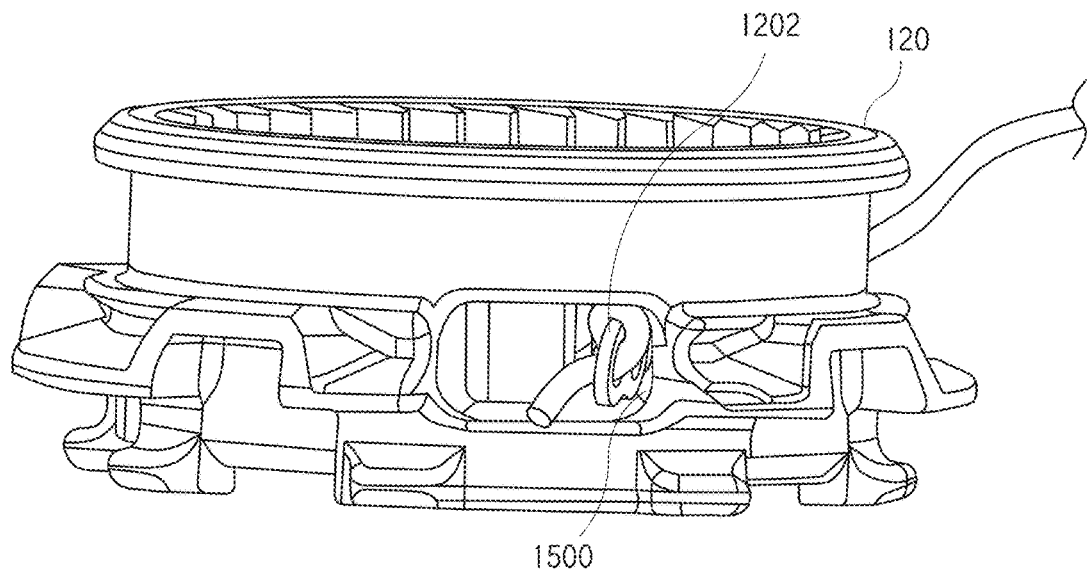
Figure 15F:
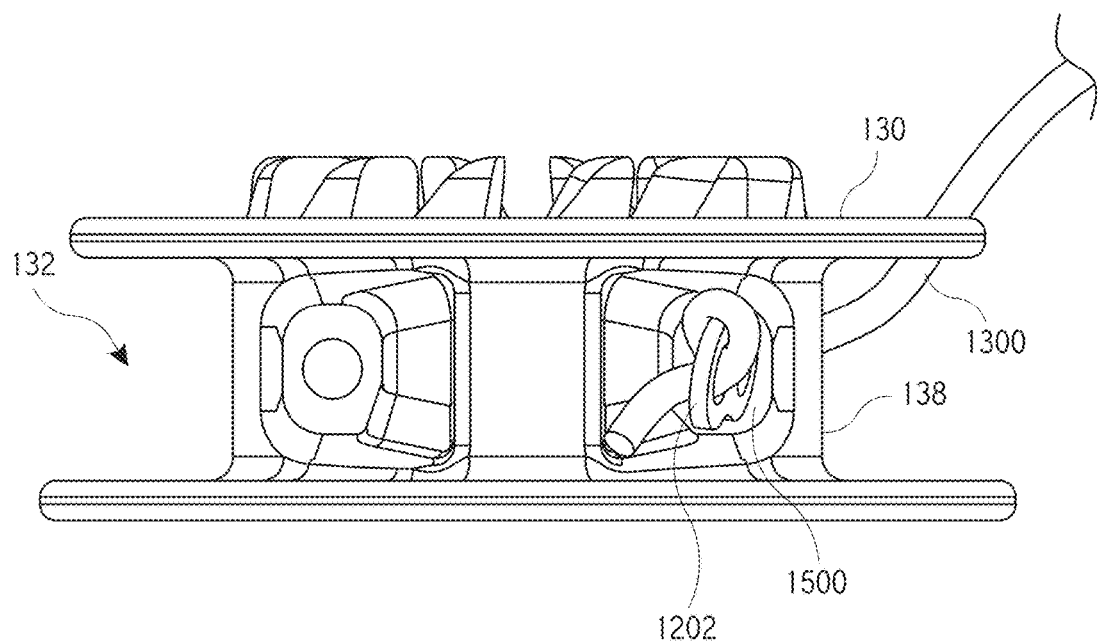

After the lace is inserted through the housing's entrance and exit ports, 1504 and 1502, and through the spool's lumen 1500, the component 1202 may be attached to the distal end of the lace 1300 as shown. The lace 1300 and component 1202 are then ready to be retracted through the exit port 1502 and secured within the spool's lumen 1500. FIGS. 15*e* and 15*f* illustrate the lace 1300 and component 1202 retracted through the housing exit port 1502 and secured within the spool's lumen 1500. As shown in FIG. 15*f*, The spool's lumen 1500 has a tapered configuration in which the lumen's diameter or opening is largest near a cylindrical wall 138 of the spool 130 and in which the lumen 1500 tapers and narrows as it projects inward from the cylindrical wall 138. The lumen's opening near the cylindrical wall 138 is larger than a width and thickness of the component 1202 so that the entire component 1202 may be retracted within the lumen 1500. Stated differently, the component 1202 is sufficiently small so that when the component 1202 is retracted within the spool's lumen 1500, the component 1202 does not extend radially outward beyond an outer wall of the spool's centrally positioned cylindrical body member or wall.

The component 1202, however, is larger than the narrow end of the lumen 1500 in order to prevent the component 1202 from being retracted entirely through the lumen 1500. Since the component 1202 is larger than the narrow end of the lumen 1500, retraction of the component 1202 within the lumen 1500 causes the component to lodge, wedge, and/or anchor into the lumen 1500, which fixes and secures the component 1202 and lace 1300 to the spool 130. Stated differently, the component 1202 is larger than a smallest diameter of the spool's lumen so that when coupled with the lace, the component 1202 prevents the lace from being retracted through the spool's lumen 1500 and uncoupled from the spool 130. The length of the component 1202 is such that the entire component 1202 is typically positioned within the lumen 1500 so as to avoid interfering with the lace 1300 as the lace is wound about the spool's central portion or channel 132. The component 1202 may have a tapered configuration that corresponds to the taper of the lumen 1500 to facilitate in insertion of the component 1202 within the lumen 1500.

Figure 16:
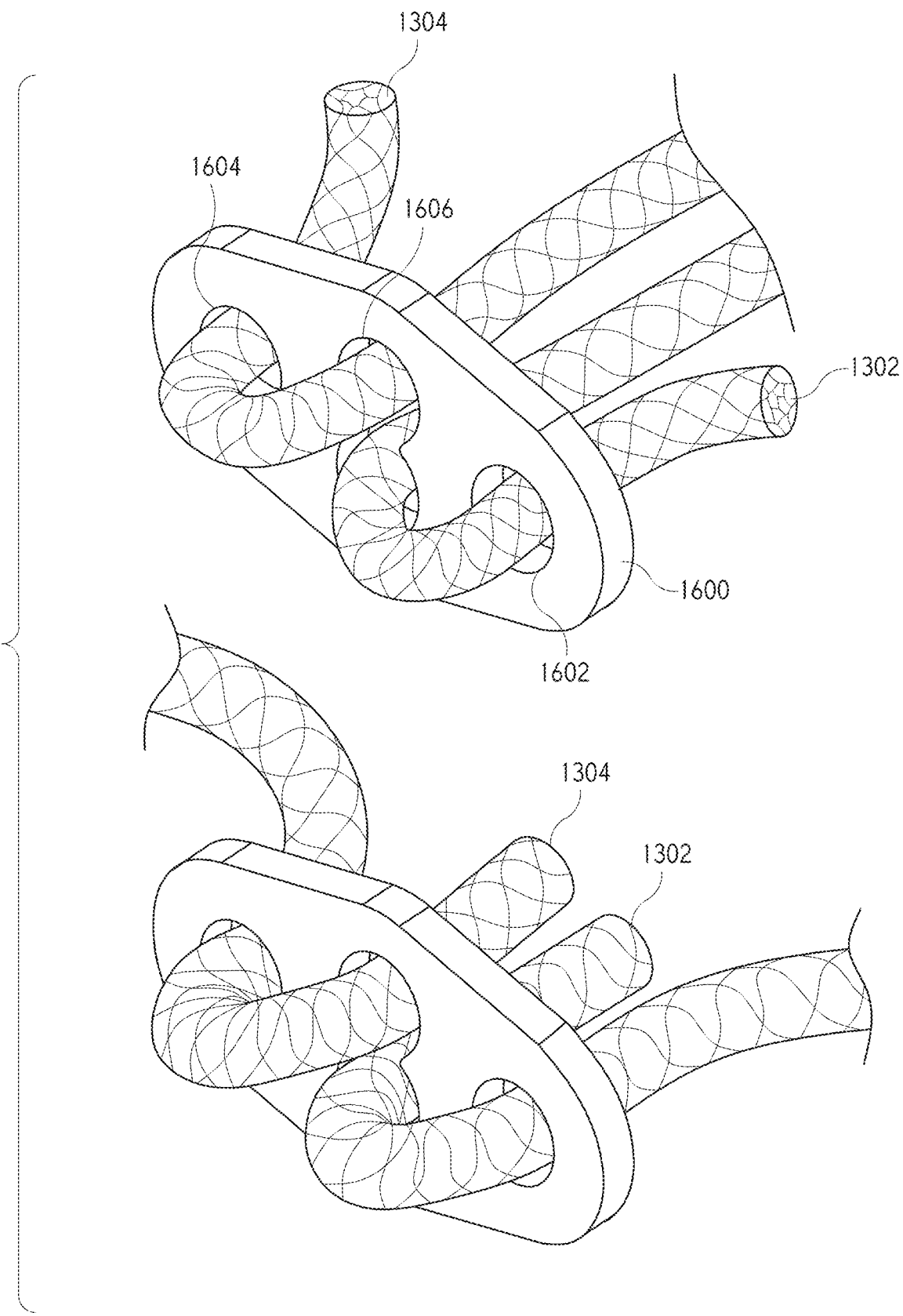
FIG. 16 illustrates another embodiment of a coupling component that is coupleable with opposing ends of a lace.

Referring now to FIG. 16, illustrated is another embodiment of a component 1600 that may be coupled with two lace ends, 1302 and 1304. Typically, the lace ends, 1302 and 1304, are opposite ends of the same lace, although the lace ends, 1302 and 1304, may be ends of separate laces. The component 1600 includes a first aperture 1602, a second aperture 1604, and a third aperture 1606. The first aperture 1602 and second aperture 1604 are positioned on opposite sides of the component 1600 while the third aperture 1606 is positioned within or near the center of the component 1600. The third aperture 1606 includes two circular or other shaped holes that are connected on one side. In some embodiments, the two circular holes may be separated from one another. The component 1600 is configured so that one of the lace ends 1302 is inserted through the first aperture 1602 and through one of the holes of the third aperture 1606 while the other lace end 1304 is inserted through the second aperture 1604 and through the other hole of the third aperture 1606. As shown in FIG. 16, the lace ends, 1302 and 1304, may be inserted through the first and second apertures, 1602 and 1604, first or may be inserted through the third aperture 1606 first. The various apertures of the component 1600 may have different diameters or shapes to aid in securing the lace ends, 1302 and 1304, about the component 1600.

Figure 17:
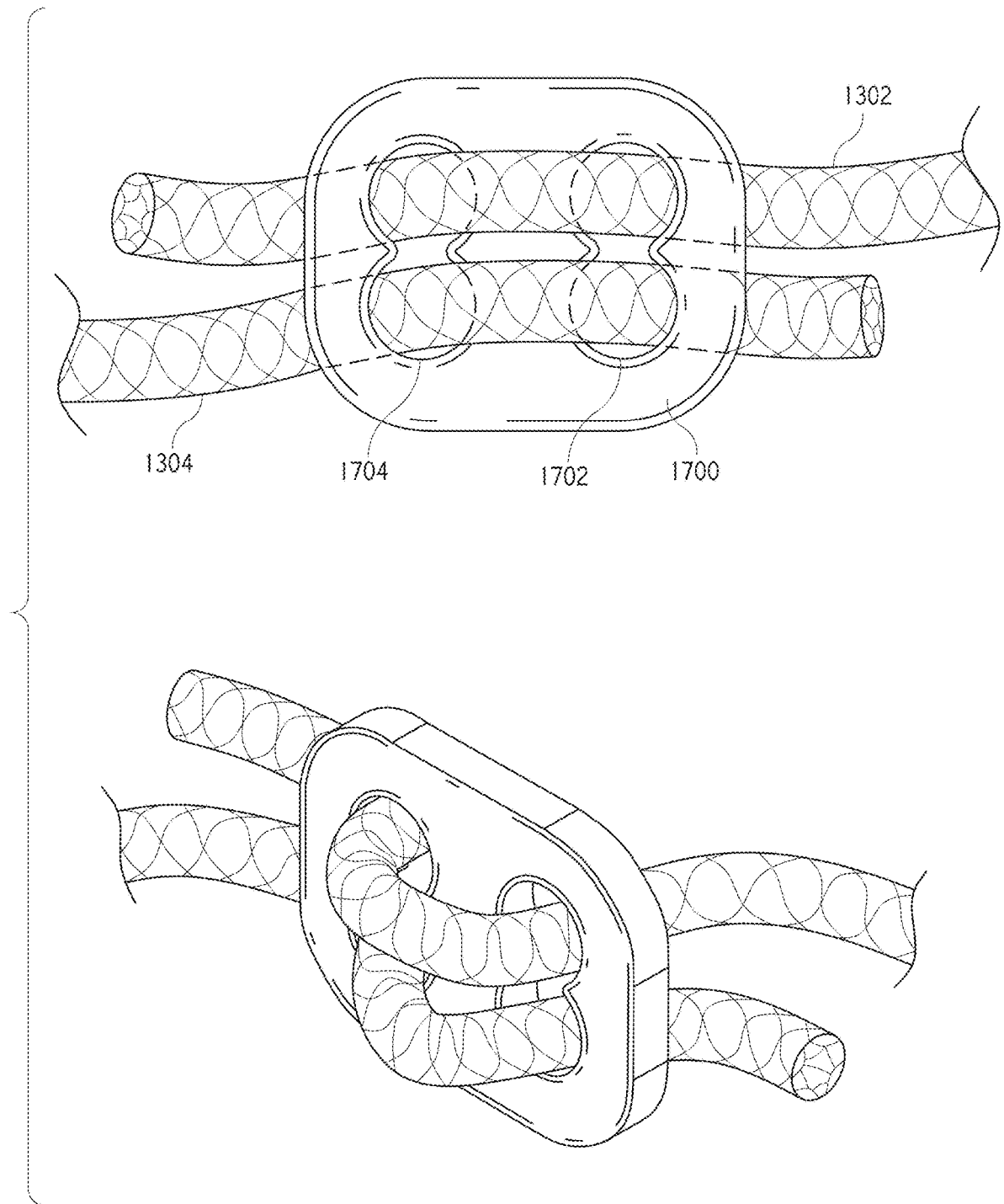
FIGS. 17-19 illustrate various embodiments of coupling components.

FIG. 17 illustrates a similar component 1700 except that the component 1700 includes a first aperture pair 1702 and a second aperture pair 1704. Each aperture pair, 1702 and 1704, includes circular holes or openings that are connected on one side. In another embodiment, each of the holes or openings of the aperture pairs, 1702 and 1704, may be separate from one another so that the component 1700 includes four separate holes or openings. The lace ends, 1302 and 1304, may be attached to the component 1700 by inserting one of the lace ends 1302 through one hole/opening of each aperture pair, 1702 and 1704, and by inserting the other lace end 1304 through the other hole/opening of each aperture pair, 1702 and 1704. As illustrated, the lace ends, 1302 and 1304, may be inserted in opposite directions through the holes/openings of each aperture pair, 1702 and 1704. In other embodiments, the lace ends, 1302 and 1304, may be inserted in the same direction through the holes/opening of each aperture pair, 1702 and 1704.

Figure 18:
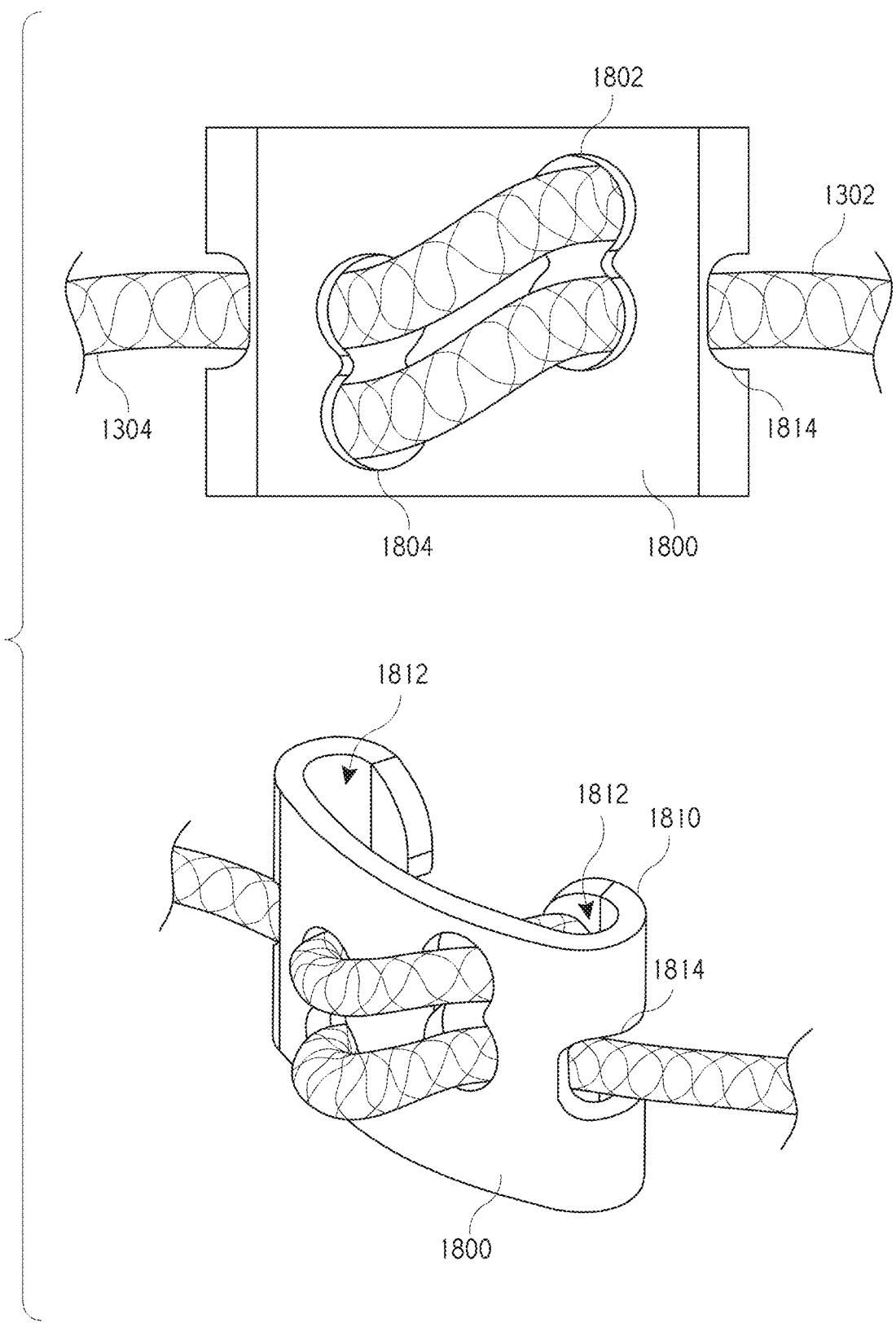

FIG. 18 illustrates a component 1800 that is similar to the component 1700 of FIG. 17. The component 1800 includes a first aperture pair 1802 and a second aperture pair 1804 having holes/openings that may be connected or separate from one another. The aperture pairs, 1802 and 1804, may be vertically offset from one another as illustrated or may be vertically aligned as desired. The component 1800 is curved and may include opposing hooked ends 1810. The lace ends, 1302 and 1304, may be inserted through the aperture pairs, 1802 and 1804, as previously described and the distal ends of the lace ends, 1302 and 1304, may be positioned within pockets or cavities 1812 that are formed from the hooked ends 1810 of the component 1800. Since the opposing ends 1810 of the component 1800 are hooked or curved, the component 1800 may include slots or apertures 1814 through which the lace ends, 1302 and 1304, are inserted.

Figure 19:
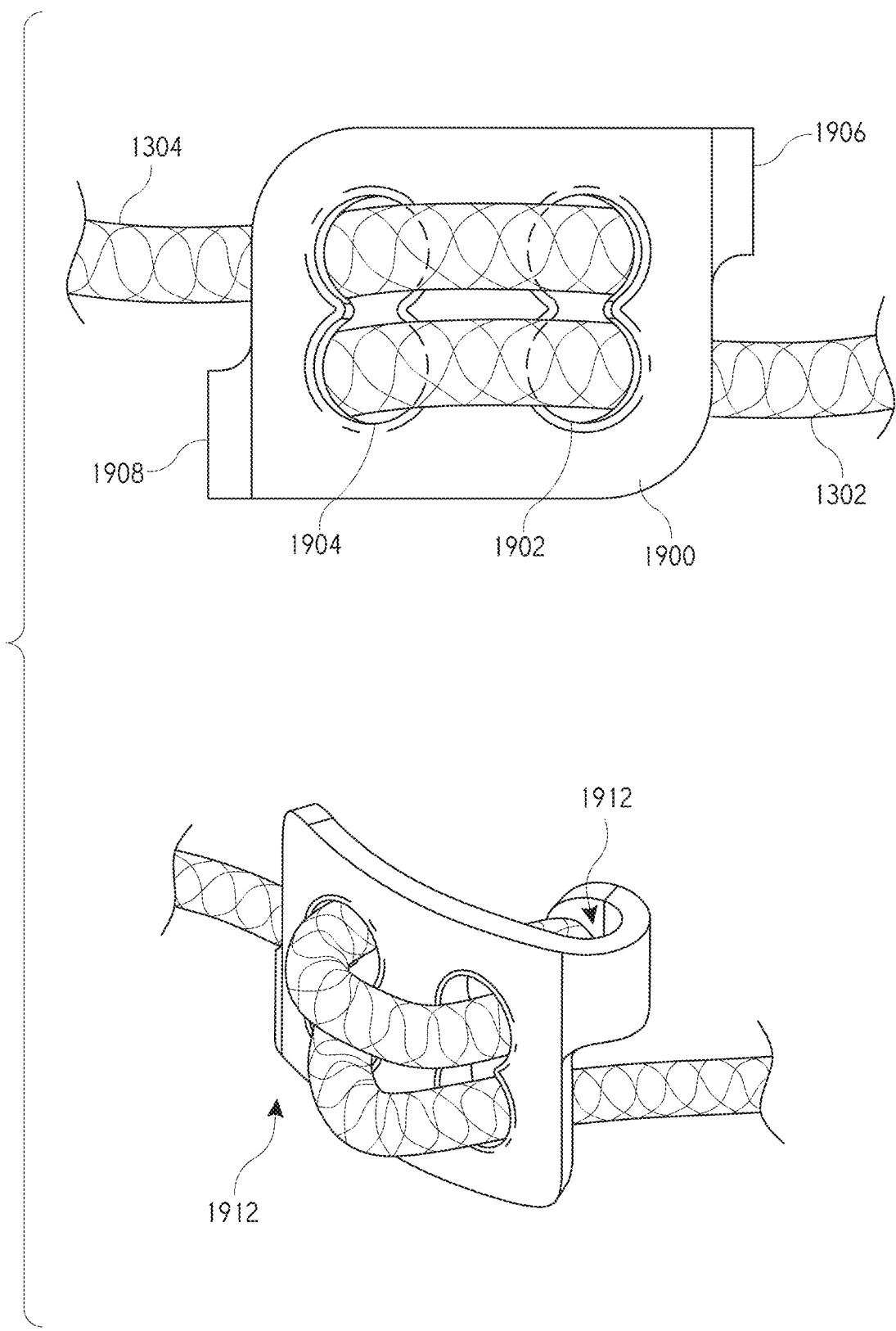

FIG. 19 illustrates a component 1900 that is similar to the component 1800 of FIG. 18. The component 1900 includes a first pair of apertures 1902 and a second pair of apertures 1904 through which the lace ends, 1302 and 1304, are inserted as previously described. The component also includes opposing hooked ends 1906 and 1908 except that the hooked ends, 1906 and 1908, do not traverse along the entire lateral width of the component 1900. Rather, the hooked ends, 1906 and 1908, only extend along a portion of the lateral width and are positioned on opposing sides of the component 1900. Since the hooked ends, 1906 and 1908, only extend along a portion of the lateral width, the component 1900 does not need to include a slot or aperture (e.g., slot 1814) within the hooked ends. The distal end of the lace ends, 1302 and 1304, may be positioned within pockets or cavities 1912 that are formed from the hooked ends, 1906 and 1908.

Figure 20:
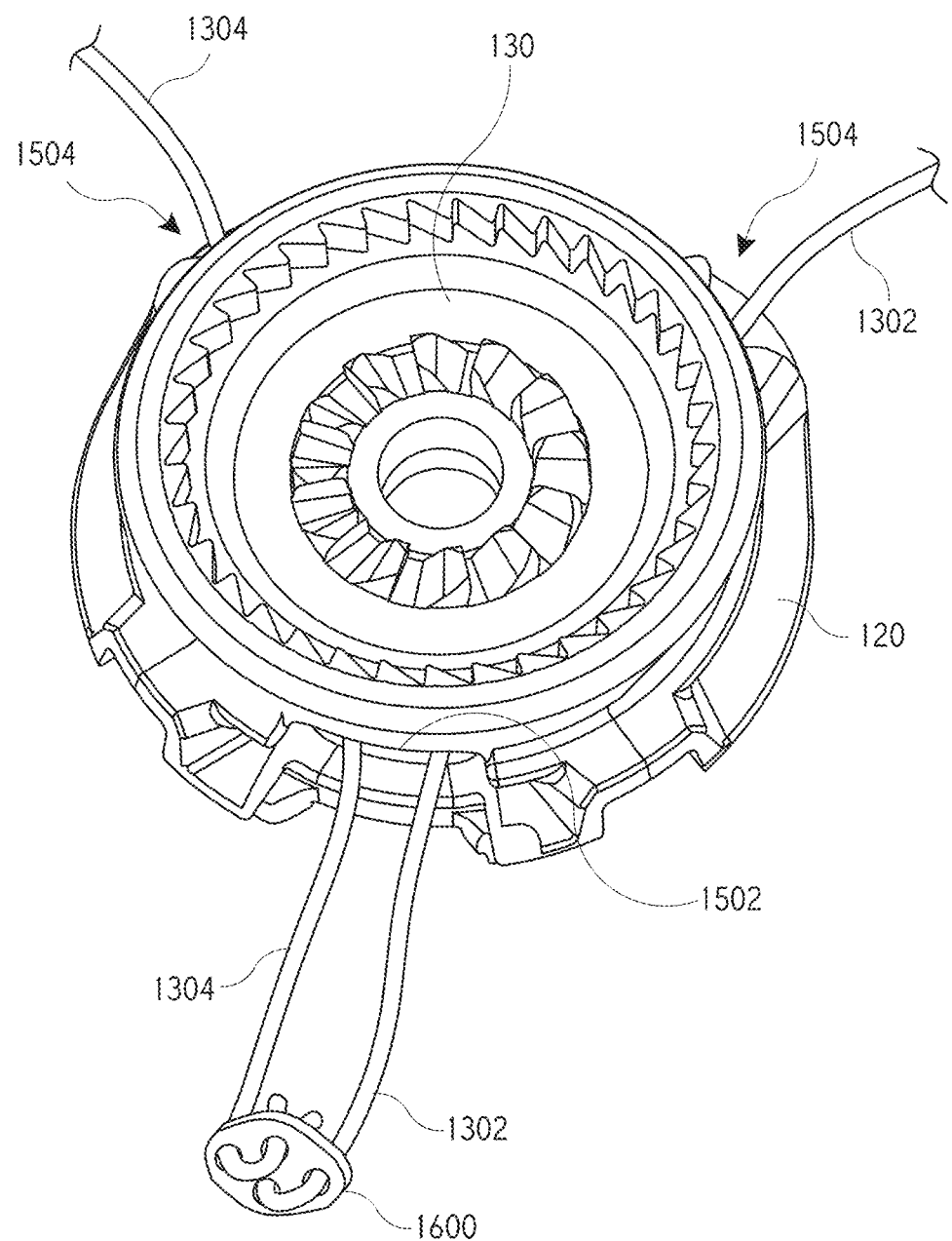
FIG. 20 illustrates the components of FIGS. 16-19 being employed to secure opposing ends of a lace with a spool of a closure system.

Referring now to FIG. 20, illustrated is a representation of the components of FIGS. 16-19 being used to couple the lace ends, 1302 and 1304, with the spool 130 of the closure system 100. The spool 130 is positioned within the interior region of the housing 120 and is aligned with the housing 120 so that the spool's lumens (not shown) are aligned with the housing's entrance ports 1504 and the exit port 1502. The lace ends, 1302 and 1304, are inserted through the entrance ports 1504, through the spool's lumens, and through the exit port 1502. The component 1600 is coupled with the lace ends, 1302 and 1304. The component 1600 and lace 1300 may then be retracted through the exit port 1502 and within the lumen of the spool 130 to operationally couple the lace ends, 1302 and 1304, with the spool 130 and closure system 100.

Figure 21A:
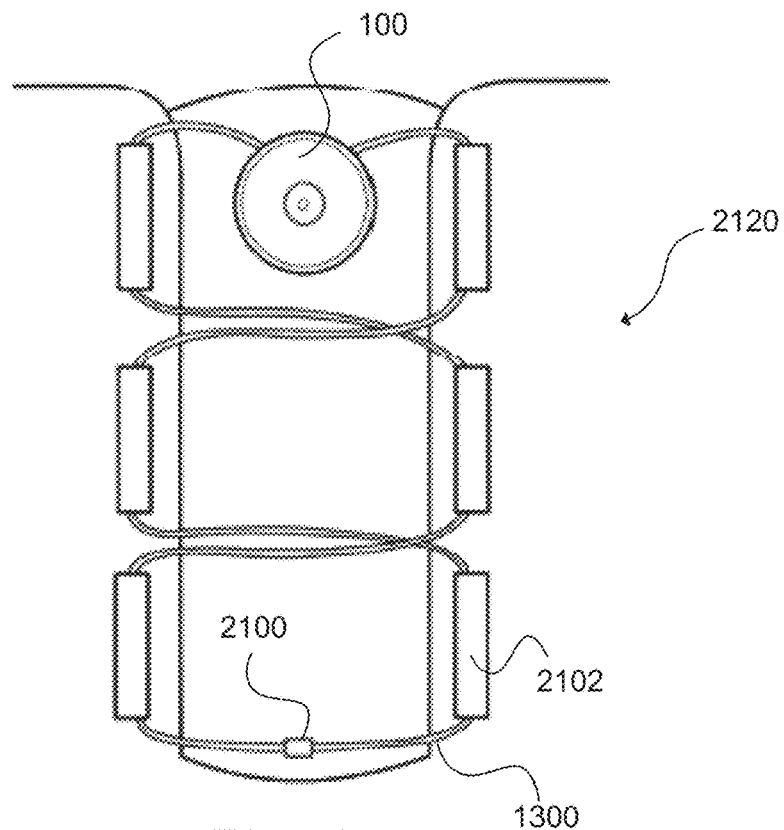
FIGS. 21a-b illustrate an additional use of the lace coupling components of FIGS. 12a-14 and FIGS. 16-19.
Figure 21B:
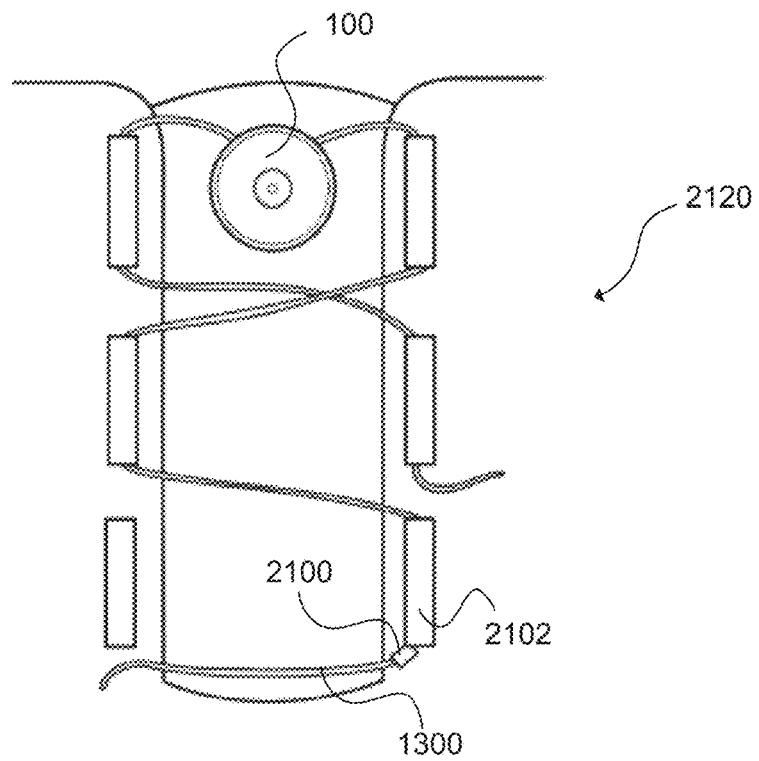

Referring now to FIGS. 21*a* and 21*b*, illustrated is an additional use of the lace coupling components of FIGS. 12*a*-14 and 16-19. In FIGS. 21*a-b*, the lace coupling components are identified by the reference number 2100, although it should be realized that the lace coupling component 2100 may represent any of the components illustrated and described in FIGS. 12*a*-14 and 16-19.

The component 2100 is employed in FIGS. 21*a-b* as a lace stop member that maintains the tightness of an article when the lace breaks. In FIG. 21*a*, a closure system 100 is attached to an article 2120, such as a shoe. The lace 1300 is operationally coupled with the closure system 100 so that operation of the closure system 100 adjusts the tension in the lace 1300 and thereby adjusts the tightness of the article 2120. The lace 1300 is guided about a lace path along the article 2120 via a plurality of guide members 2102. The guide members 2102 are configured to allow the lace 1300 to slide, shift, or move in relation to the guide members 2102 with minimal frictional interference.

The component 2100 is coupled to the lace 1300 so that it is positioned between two guide members 2102 near the distal end of the lace path. The component 2100 is coupled with the lace 1300 as described herein, such as by inserting the lace through apertures of the component 2100. The component 2100 is flexible enough so that the lace 1300 may be easily coupled with the component 2100, but is stiff enough that it remains secured about the lace 1300 in operation. The component 2100 is typically positioned equidistant between opposing ends of the lace 1300, but may be positioned elsewhere as desired. In some embodiments, an outer surface of the component 2100 may include a logo or other indicia to provide a desired visual appeal.

FIG. 21*b* illustrates the component 2100 being utilized to maintain a tension in the lace 1300 upon breakage of the lace 1300. Specifically, breakage of the lace 1300 will cause the lace 1300 to shift and slide through the lace guides 2102 due to the tension in the lace 1300 and in the article 2120. Since the component 2100 is secured about the lace 1300, sliding of the lace 1300 through the lace guides 2102 will cause the component 2100 to contact and engage with one of the lace guides 2102. Similar to the lumen 1500 of the spool 130, the component 2100 is larger than a channel or opening of the lace guide 2102 and thus, the component 2100 is not able to slide within or through the channel or opening of the lace guide 2102. Rather, the component 2100 becomes wedged and/or anchored to the lace guide 2102, which prevents further sliding or shifting of the lace 1300 through the lace guide 2102. The article 2120 may be slightly less tight or secure due to the broken lace 1300, but the article will be substantially more tight and secure than would otherwise occur due to the broken lace 1300. In addition, with the component 2100 secured about the lace guide 2102, the closure system 100 may be operated to further tension the lace 1300 and tighten the article 2120.

Figure 22:
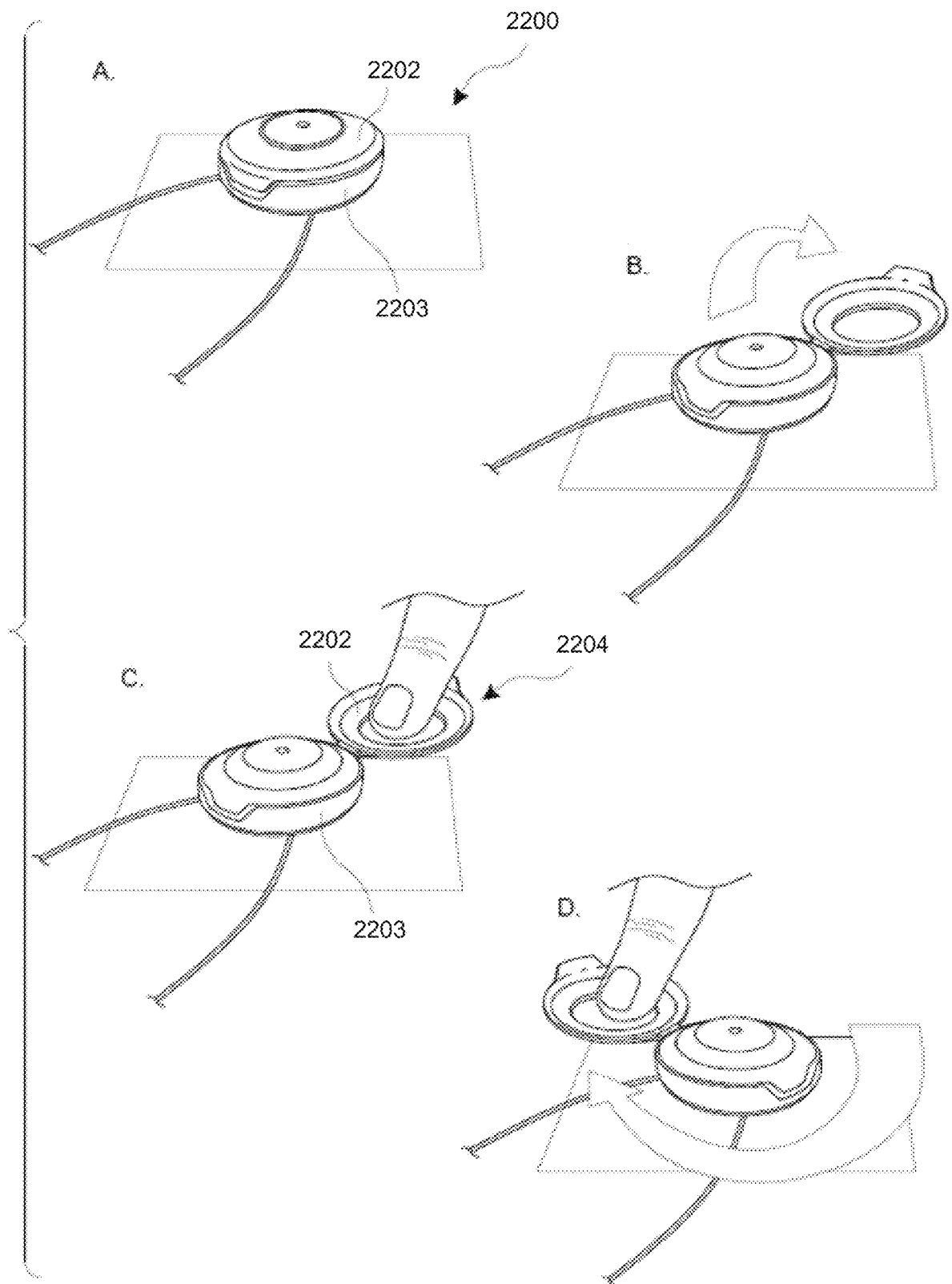
FIG. 22 illustrates a reel based closure system that includes a cap that may be pivotably coupled with a knob or housing of a reel based system.

Referring now to FIG. 22, illustrated is a reel based closure system 2200 that includes a cap 2202 that may be pivotably coupled with the knob or housing 2203 of the reel based system 2200. The cap 2202 may be in the shape of an annular or dome shaped ring. In operation, the cap 2202 is folded backward about a pivot point. The cap 2202 is then employed to rotate the knob of the reel based closure system 2200. For example, the cap 2202 may be used as a handle to rotate the knob or another component of the reel based closure system 2200. In some instance, the cap 2202 may be operationally coupled with the spool (not shown) so that rotation of the cap 2202 directly causes rotation of the spool within the reel based closure system 2200. The cap 2202 may have a recessed central portion 2204 that is configured to accommodate a finger of a user, or that otherwise allows the cap 2202 to be easily grasped and rotated. In other embodiments, the reel based closure system 2200 may include a lever, hinged component, wind-up component, or some other component that aids in rotating the knob or spool of the reel based closure system 2200. In some embodiment, rotation of the knob or spool in a tightening or loosening direction may be prohibited when the cap 2202 is in a closed position.

Figure 23A:
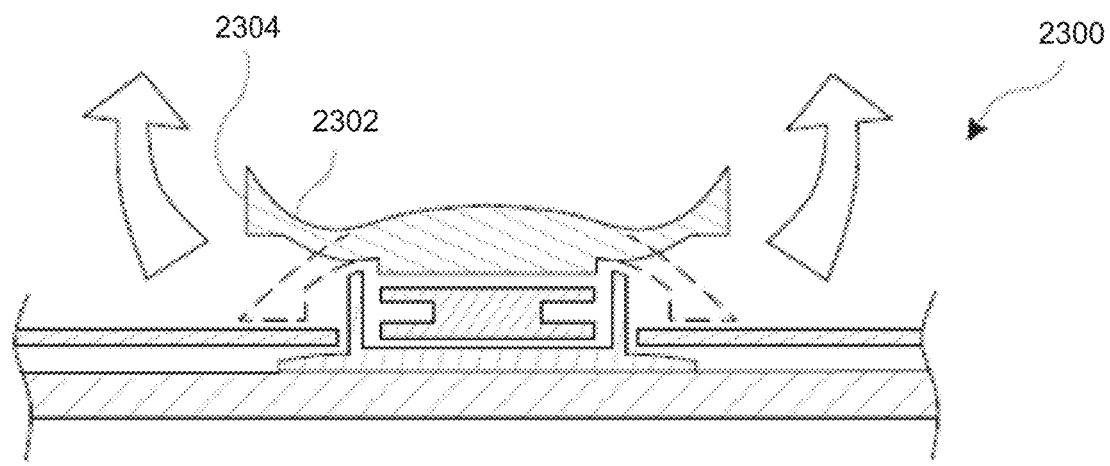
FIGS. 23a-c illustrate a reel based closure system that includes an invertible knob.
Figure 23B:
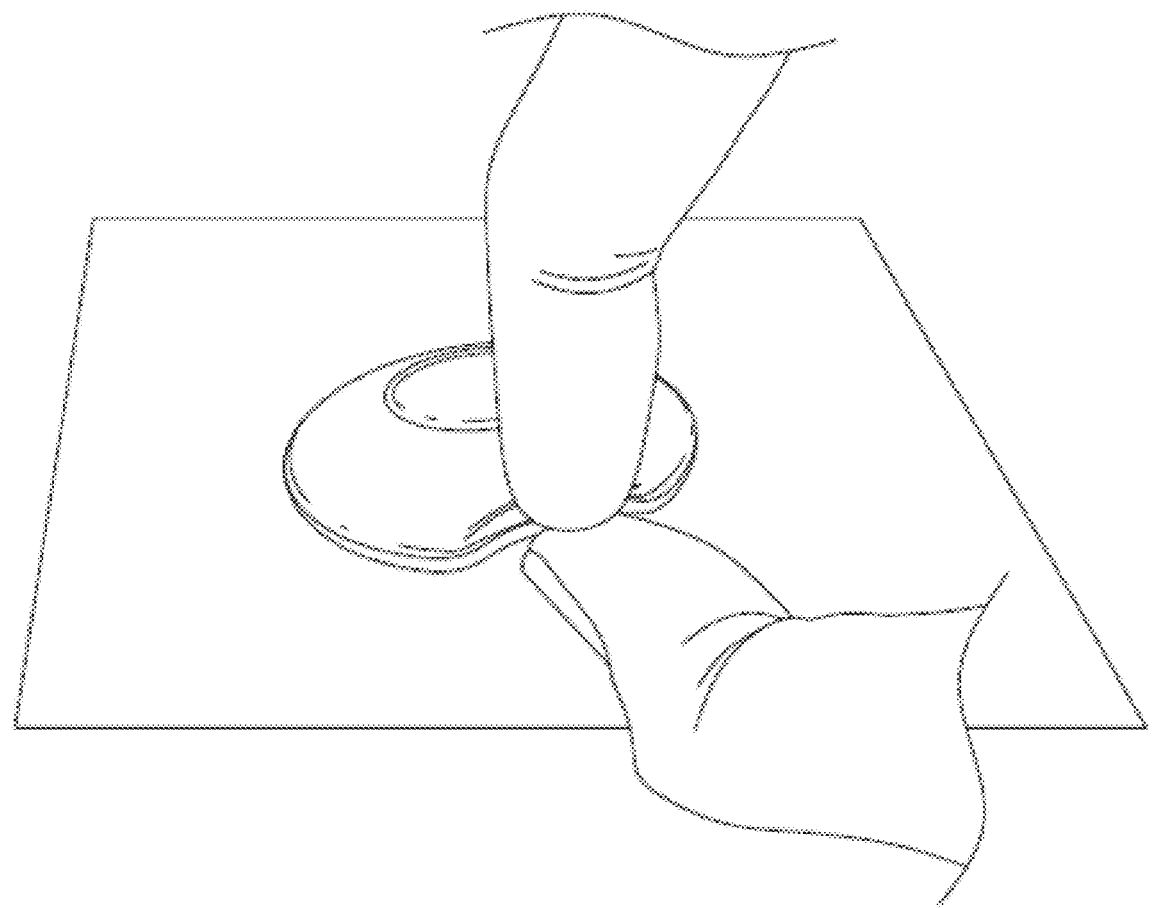
Figure 23C:
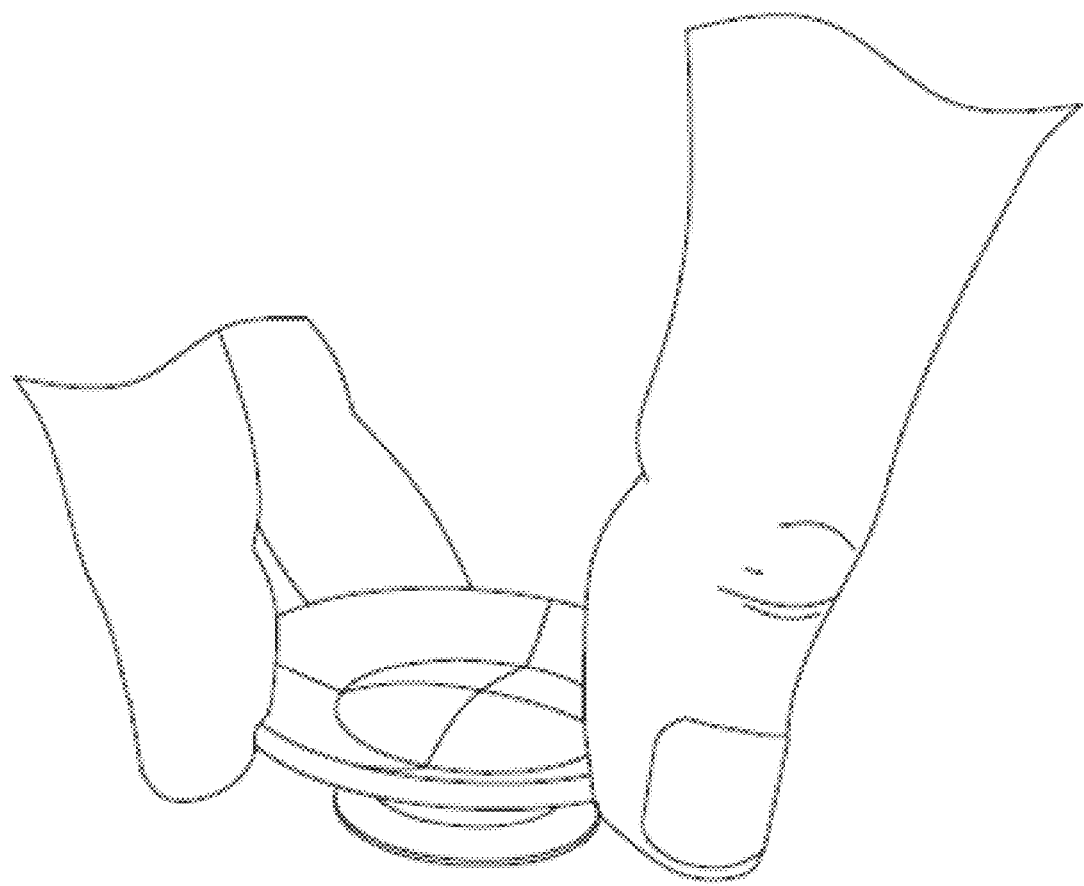

Referring now to FIGS. 23*a-c*, illustrated is a reel based closure system 2300 that includes an invertible knob 2302. Specifically, the knob 2302 is made of a flexible or resilient material that allows the knob 2302 to be inverted between two positions or configurations. In a first configuration, the knob 2302 may have a relatively low profile and domed shaped. In the low profile configuration, an inner edge or lip 2304 of the knob 2302 may be positioned against or adjacent the outer surface of a shoe or article. The domed or low profile shape of the knob 2302 may help to conceal the reel based closure system 2300 and may prevent accidental opening or operation of the system or knob 2302, thereby minimizing access to the system or knob 2302. To invert the knob 2302, a user may place their finger or another object under the lip or edge 2304 of the knob 2302 and pull the outer edge of the knob 2302 upward. The knob 2302 may spring or bend into an outward expanded configuration in which the lip or edge 2304 is easily accessible to a user. The user may grasp the lip or edge 2304 in order to rotate the knob 2302 and thereby tension a tension member (not shown) of the system. The lip or edge 2304 may be made of a tacky material that is easy to grasp in the outward expanded configuration and that grips the surface of the shoe or article in the low profile configuration. The knob 2302 should be made of a material that is rigid enough to enable a user to grasp and rotate the knob 2302 in the expanded configuration, but flexible enough to allow the knob 2302 to be inverted as described. In some instances, the knob 2302 may be configured to only rotate when in the expanded configuration, which may further minimize accidental operation of the system.

Figure 24A:
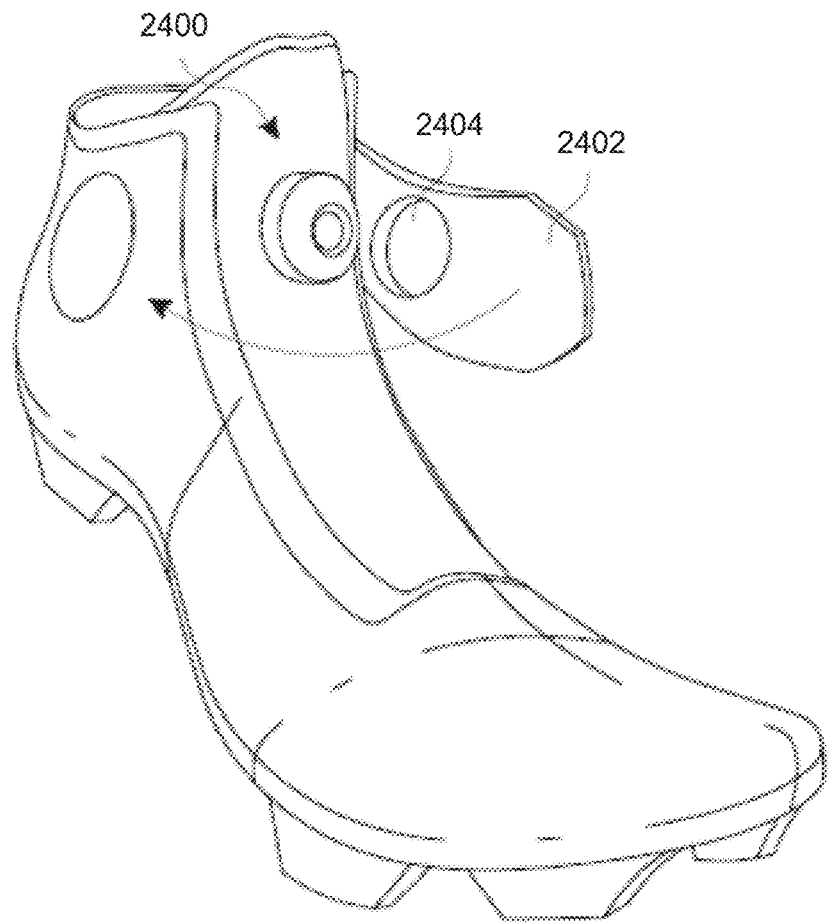
FIGS. 24a-b illustrate a strap that is positionable over a reel based closure system to prevent or minimize accidental operation of the reel based closure system.
Figure 24B:
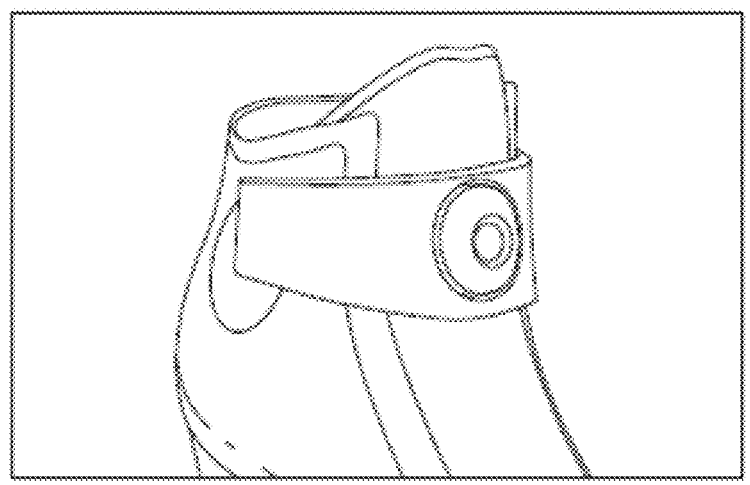

Referring now to FIGS. 24*a-b*, illustrated is a strap 2402 that may be positioned over a reel based closure system 2400 in order to prevent or minimize accidental operation of the reel based closure system and/or loosening or tightening of a lace/tension member. The strap 2402 includes a fixed end that is attached to the shoe or article and a free end that is foldable over the reel based closure system 2400. The free end is fixable to the shoe or article after it is folded over the reel based system 2400. In some embodiments, the strap 2402 includes a recessed portion or garage 2404 that is sized and shaped to accommodate the reel based closure system 2400. Specifically, the recessed portion 2404 is configured so that the reel based closure system 2400 easily fits within the recessed area, which minimizes or prevents the strap 2402 from applying a downward pressure on the reel based closure system 2400 that may be uncomfortable or irritating to an underlying foot. The fixed end of the strap 2402 is typically made of a less flexible material to ensure that the recessed portion or garage 2404 is positioned directly over the reel based closure system when the strap 2402 is folded about the shoe or article.

In other embodiments, a different portion of the shoe (e.g., the tongue) may be folded over the reel based closure system, or other components may be used to cover and conceal the reel based closure system, such as a pair of bars or straps, a rigid member, and the like.

Figure 25A:
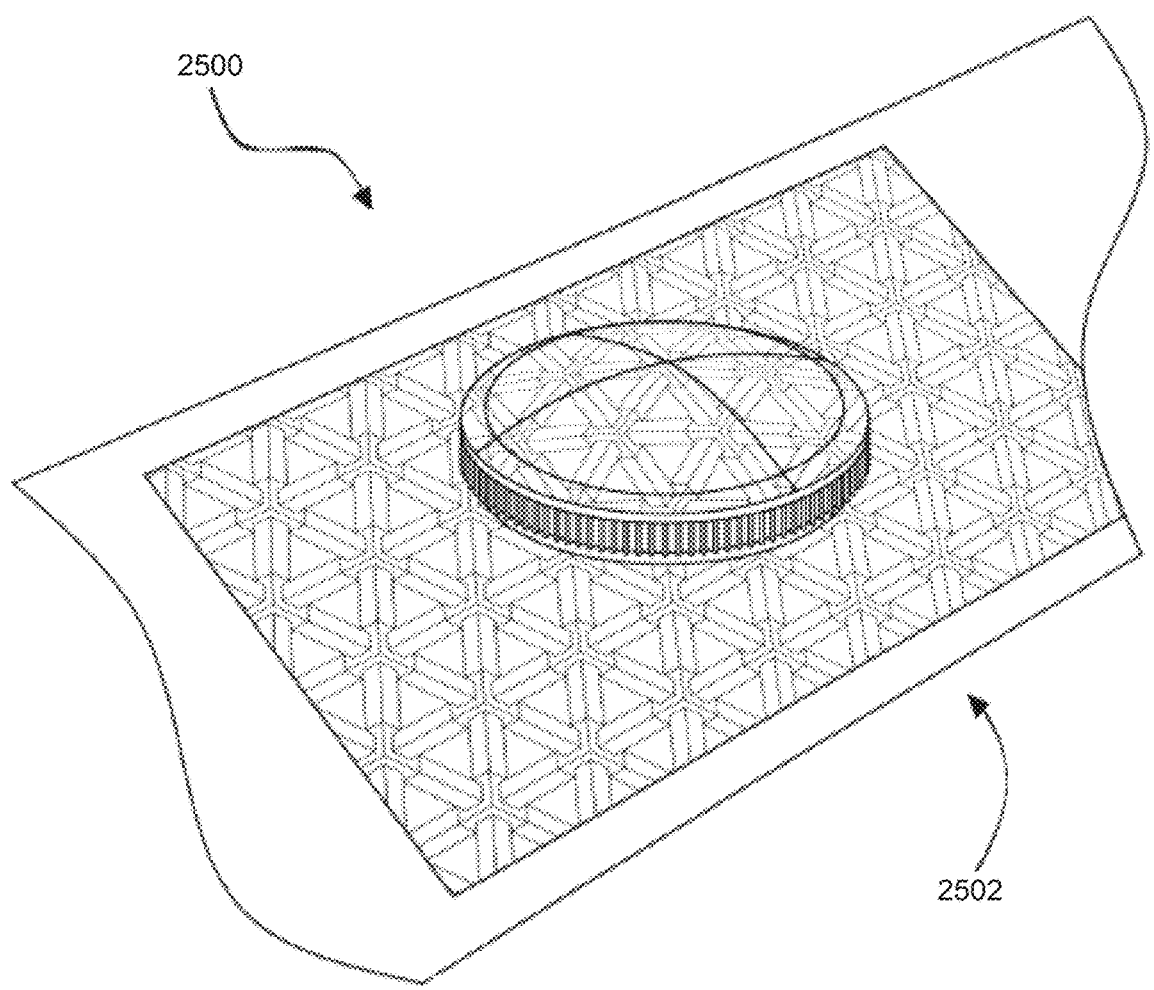
FIGS. 25a-b illustrate a reel based closure system that is configured to be color and/or pattern matched with an underlying article.
Figure 25B:
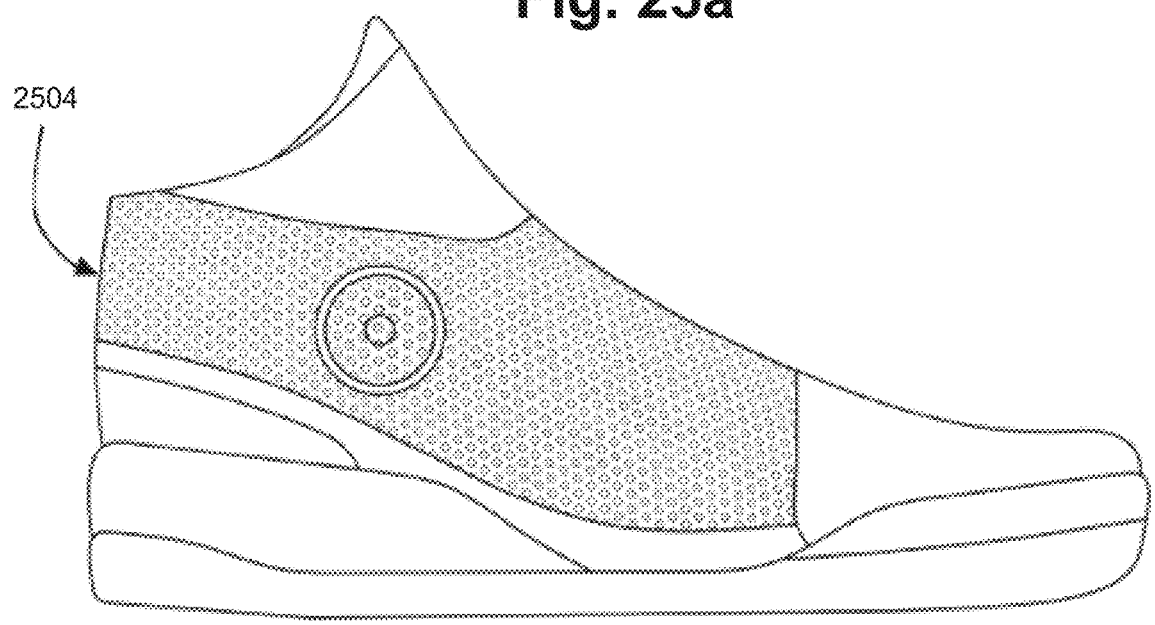

Referring now to FIGS. 25*a-b*, illustrated is a reel based closure system 2500 that is configured to be color and/or pattern matched with an underlying article 2502 or shoe 2504. Specifically, an upper surface of the knob of the reel based closure system 2500 may be UV painted to match the color and/or pattern of the article or shoe. The matched color and/or pattern of the knob may enable the reel based closure system 2500 to appear as an integrated component of the article or shoe. The ability to match the color and/or pattern may provide the article 2502 or shoe 2504 with a desirable aesthetic appearance.

Figure 26A:
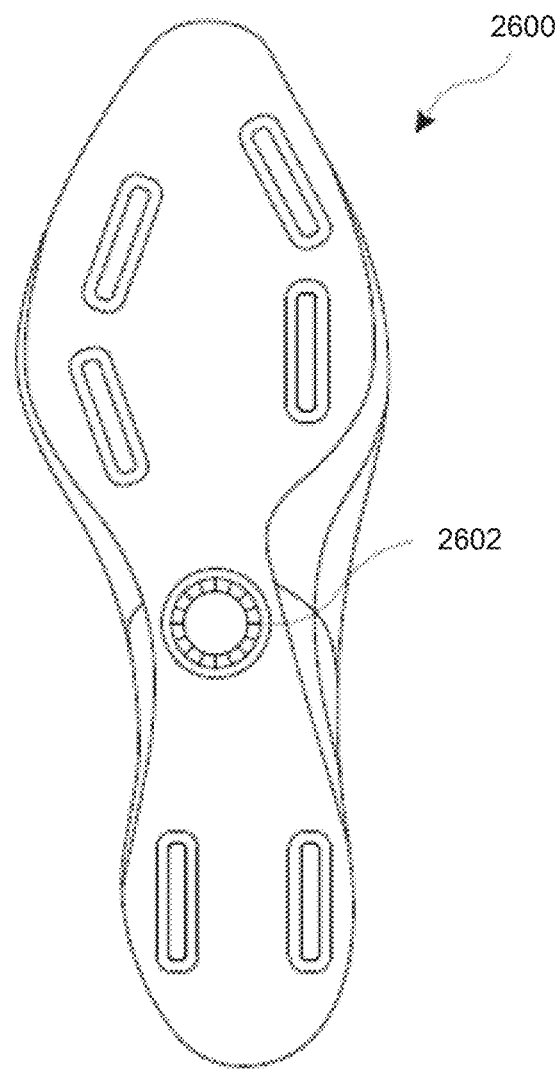
FIGS. 26a-d illustrate alternative placements of a reel based closure system about a shoe.
Figure 26B:
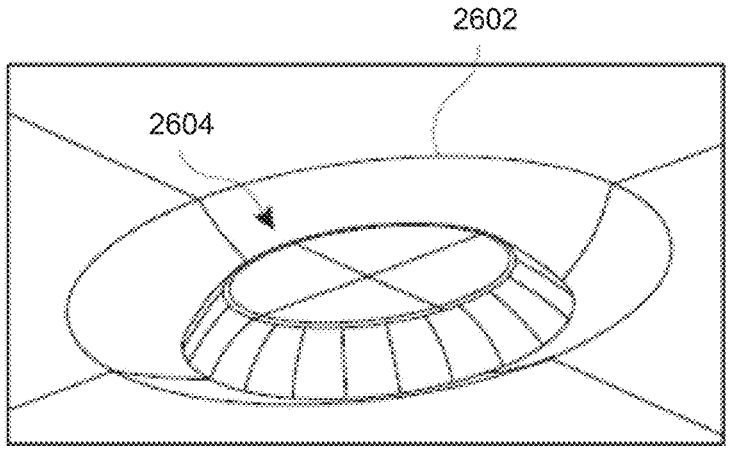

Referring now to FIGS. 26*a-d*, illustrated are alternative placements of a reel based closure system about a shoe. In FIGS. 26*a-b*, a reel based closure system 2602 is positioned on a bottom surface of the shoe 2600. The reel based closure system 2602 is illustrated as being positioned roughly midpoint about the bottom surface of the shoe 2600, although in other embodiments the reel based closure system 2602 may be positioned closer to the heel or forefront of the shoe 2600. The reel based closure system 2602 may be positioned within a recessed area 2604 of the bottom surface of the shoe so that a top of the knob of the reel based closure system 2602 is prevented from contacting the ground as the user walks or wears the shoe. The recessed area 2604 may be wide enough to enable a user to easily grasp and rotate the knob within the recessed area. Positioning the reel based closure system 2602 on the bottom of the shoe 2600 hides or conceals the reel based closure system 2602 from view and may also prevent accidental operation of the reel based closure system 2602.

Figure 26C:
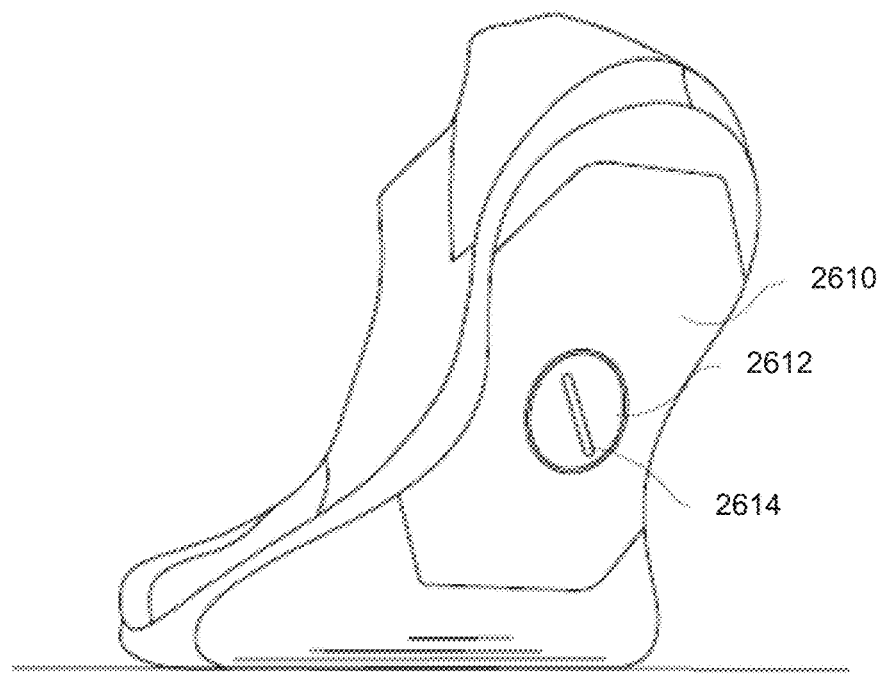
Figure 26D:
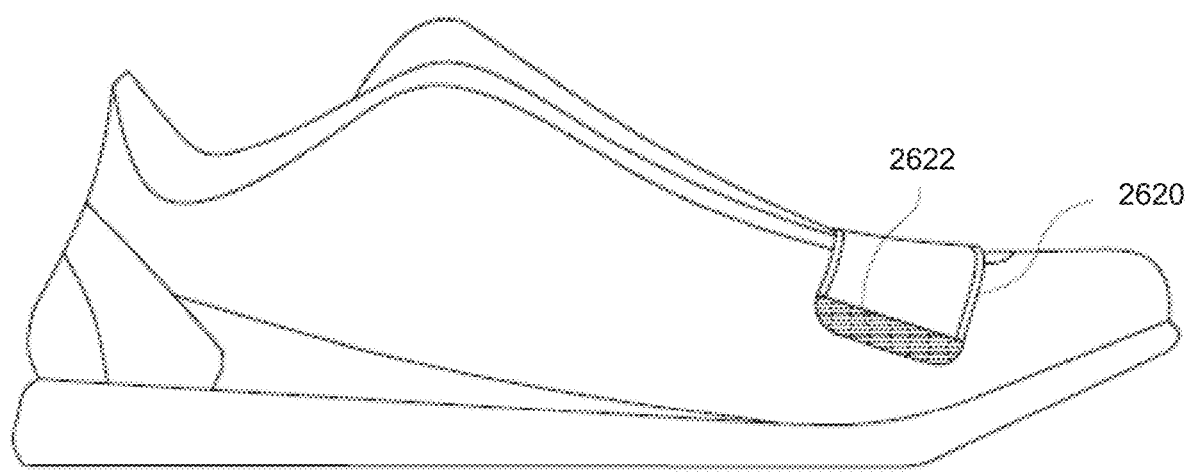

FIGS. 26*c-d* illustrates another reel based closure system 2612 that is positioned on the bottom of a shoe 2610. Like the system of FIGS. 26*a-b*, the reel based closure system 2612 of FIGS. 26*c-d* may be positioned within a recessed area as desired. The reel based closure system 2612 includes a slot or key 2614 that is configured for use as an torque input feature. The reel based closure system 2612 may be configured so that the knob may only be rotatable via the slot or key 2614. In some instances, the slot or key 2614 may be shaped and sized so that a common object, such as a quarter or screw driver, may be inserted within the slot or key 2614 to provide the input torque that rotates the knob. In other embodiments, the slot or key 2614 may be designed to require the use of a specialty tool. In some instances, the shoe 2610 may include the tool that is required or used to operate the reel based closure system 2612. For example, a distal end 2622 of a strap 2620 that is attached to the shoe 2610 may be shaped and sized so that the distal end 2622 of the strap 2620 may be inserted within the slot or key 2614 of the reel based closure system 2612. The distal end 2622 of the strap 2620 may be relatively rigid to enable the input torque to be applied to the reel based closure system 2612. The distal end 2622 of the strap 2620 may be attached to the shoe 2610 via hook and loop fasteners, mechanical fasteners, magnets, and the like. In other instances, the key or tool that is used for the slot or key 2614 may be removably attached to the shoe 2610.

Figure 27A:
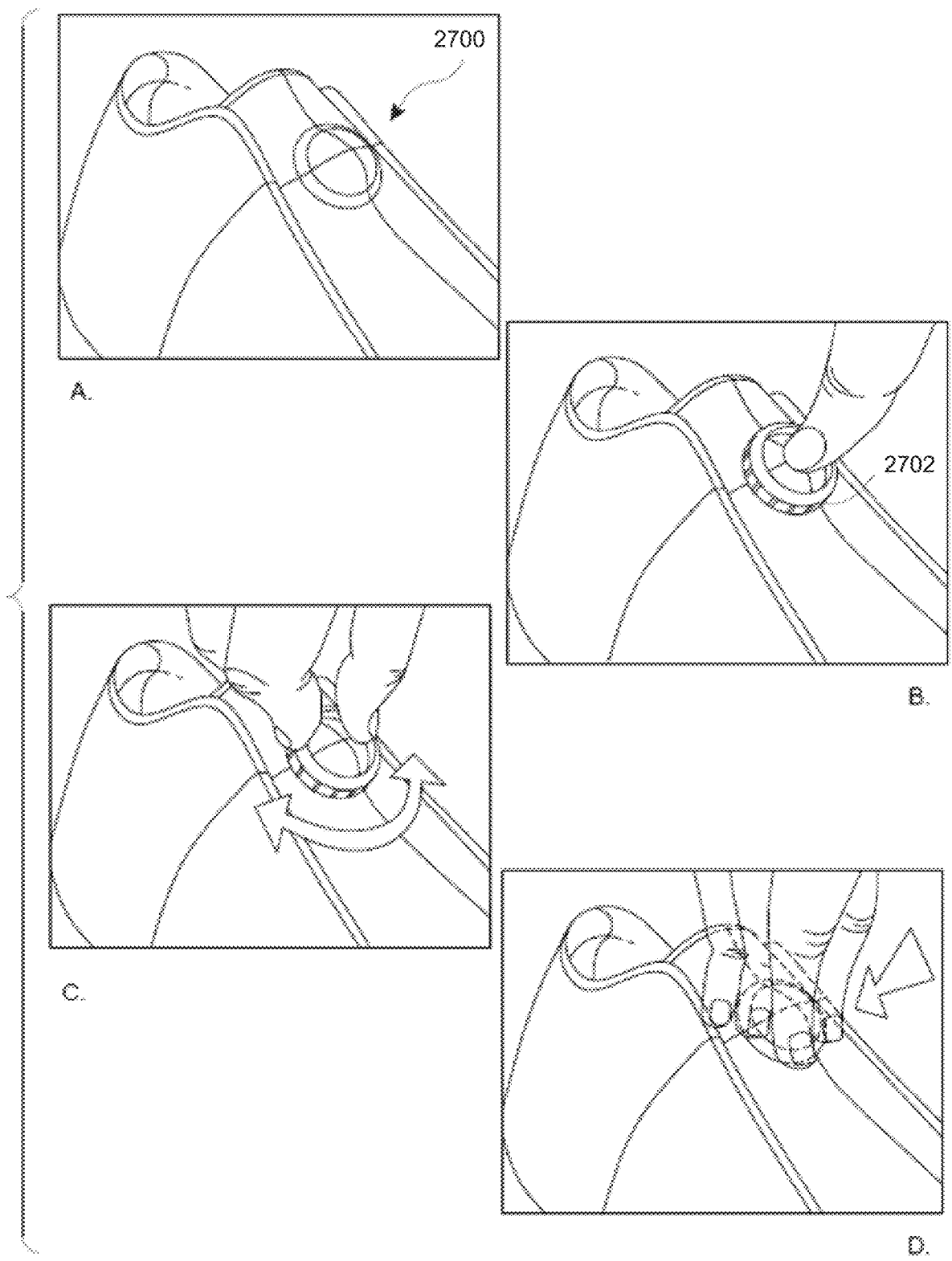
FIGS. 27a-b illustrate a reel based closure system that includes an outer annular ring that is used to rotate a spool of the reel based closure system.
Figure 27B:
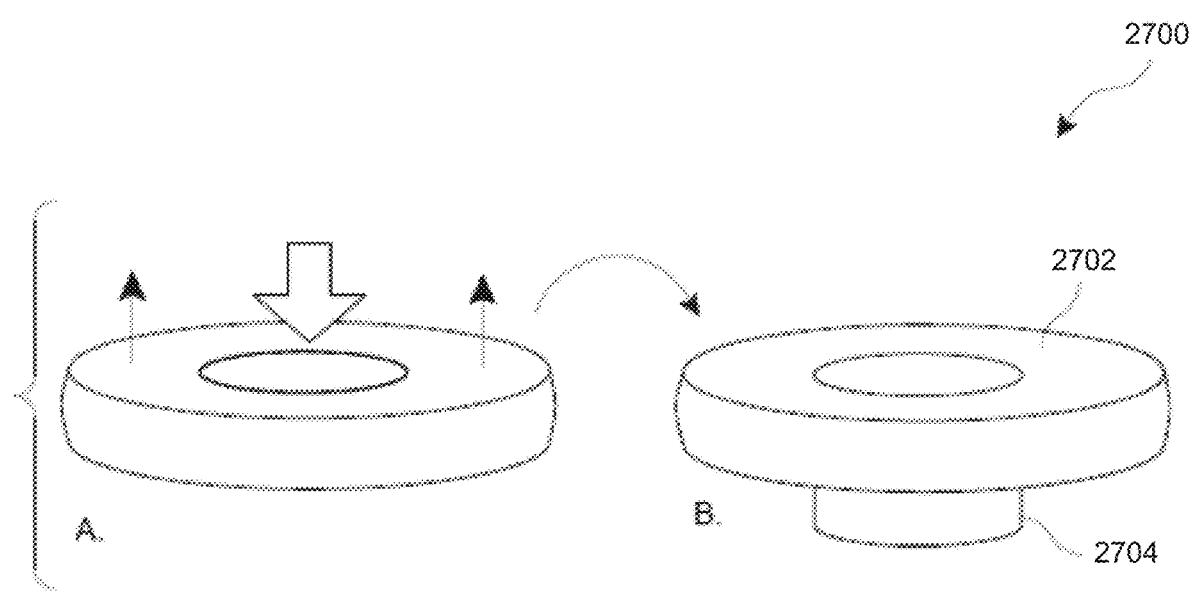

Referring now to FIGS. 27*a-b*, illustrated is a reel based closure system 2700 that includes an outer or annular ring 2702 that is used to rotate the spool and thereby tension a lace/tension member of the reel based closure system 2700. The ring 2702 is axially moveable between an engaged or locked stated and a disengaged or unlocked state. For example, the ring 2702 may initially be in the engaged or locked state in which tension on the lace is maintained and/or the ring is inoperable to further tension or loosen the lace. To unlock or disengage the system, a center portion or member 2704 of the knob may be pressed axially downward (or the ring 2702 may be pulled axially upward) to cause the ring 2702 to extend axially upward (e.g., spring or pop axially upward) from the center portion or member 2704 of the knob. With the system disengaged, the tension in the lace/tension member may automatically release, or the ring 2702 may be employed to incrementally tighten or loosen the tension of the lace/tension member. To incrementally tighten or loosen the lace/tension member, the ring 2702 may be rotated in the clockwise or counter-clockwise direction. Once a desired lace tension is achieved, or the lace tension is fully released, the ring 2702 may be pressed axially downward so that the ring 2702 aligns with the center portion or member 2704 of the knob, which locks or engages the system and maintains the tension in the lace/tension member.

Figure 28A:
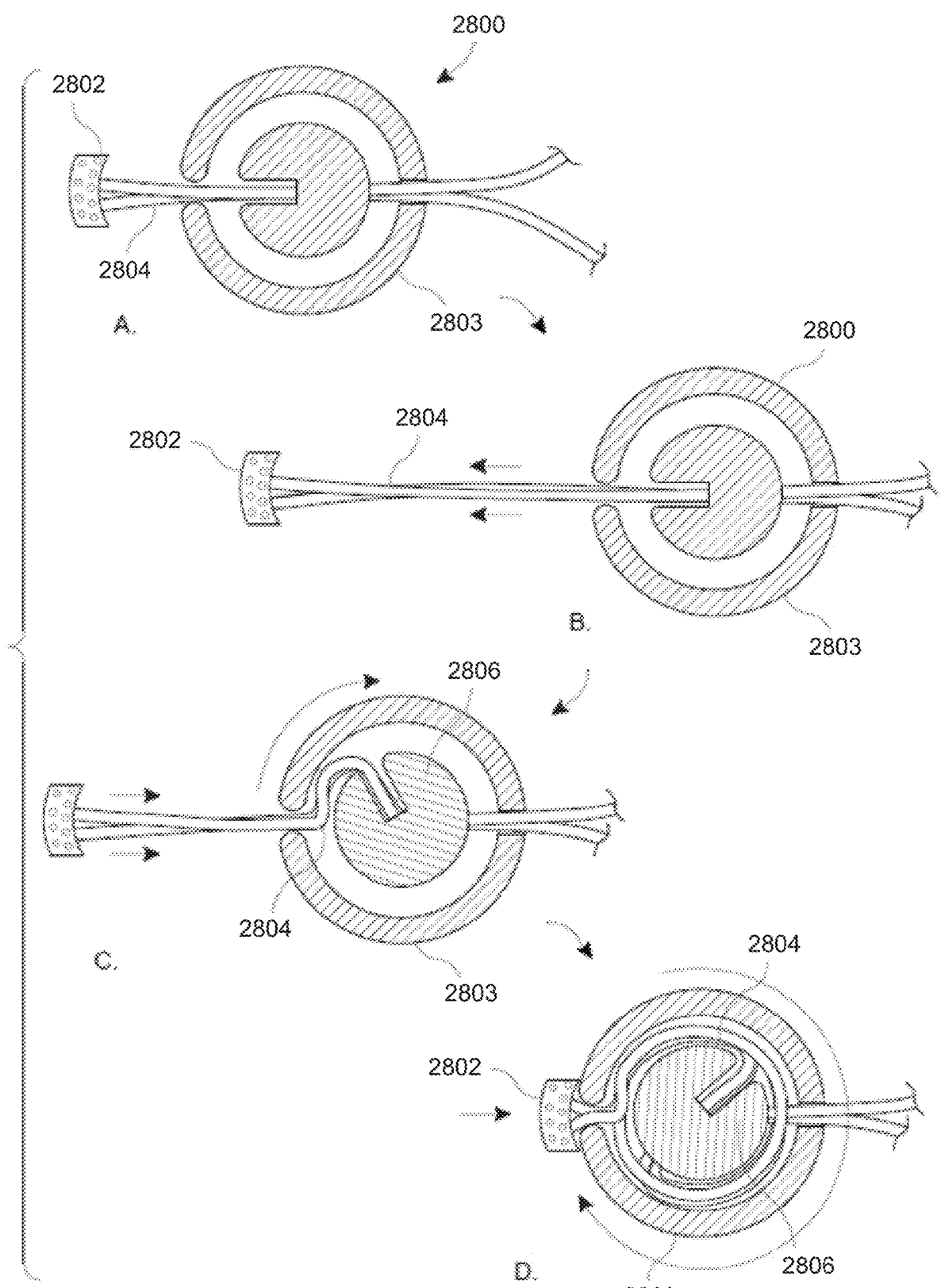
FIGS. 28a-b illustrate a reel based closure system that includes both a pull cord component and a rotary component.
Figure 28B:
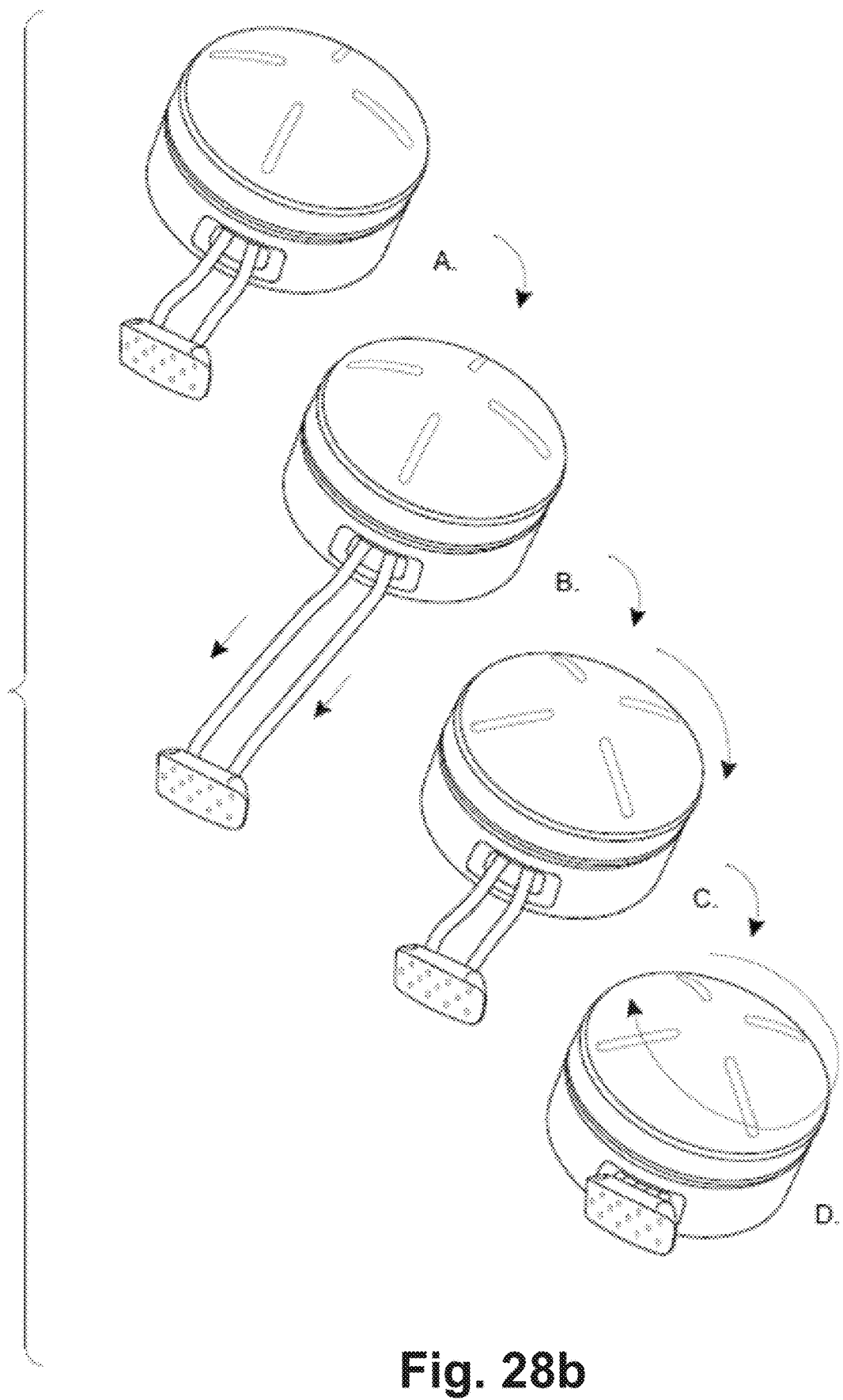

Referring now to FIGS. 28*a-b*, illustrated is a reel based closure system 2800 that includes both a pull cord component and a rotary component. The pull cord component is employed to tension a lace 2804 while the rotary component is employed to wind up the lace and/or further tension the lace 2804. The pull cord component includes a pull tab 2802 that is coupled or attached to a distal end of the lace 2804. The lace is slidably positioned through a housing 2803 and spool 2806 component of the rotary component. To tension the lace 2804 a user grasps and pulls distally on the pull tab 2802, which causes the lace 2804 to be pulled through the housing 2803 and spool 2806 of the rotary component. A knob (not shown) of the rotary component may then be rotated to rotate the spool 2806 within the housing 2803, which winds the lace 2804 about the spool 2806. The knob may be rotated until the pull tab 2802 is positioned adjacent the outer surface of the housing 2803. In some instances, winding of the lace 2804 about the spool 2806 may also additionally tension the lace 2804 and thereby additional tighten a shoe or article about which the reel based closure system 2800 is used.

The pull cord component may be used mainly for tensioning of the lace 2804 while the rotary component is mainly used for lace management to ensure that excess lace does not interfere or entangle with surrounding objects. Releasing or loosening of the system may occur in a manner opposite to that described. For example, the knob may be counter-rotated to unwind the lace 2804 from the spool 2806. The lace 2804 may be unwound until it is able to freely slide through the housing 2803 and spool 2806, at which time the lace tension may be loosened.

Figure 29:
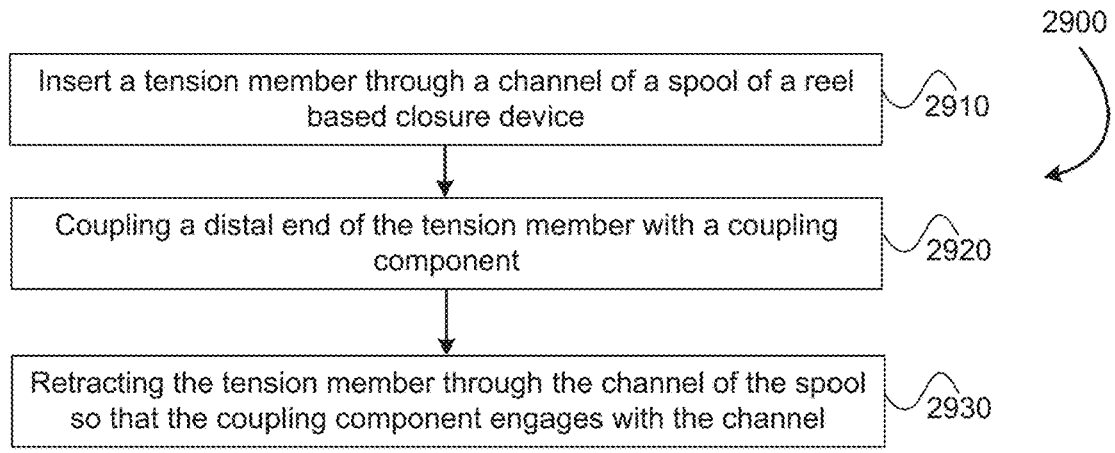
FIG. 29 illustrates a method of coupling a tension member with a reel based closure device.

Referring to FIG. 29, illustrated is a method 2900 of coupling a tension member with a reel based closure device. At block 2910, the tension member is inserted through a channel of a spool component of the reel based closure device. At block 2920, a distal end of the tension member is coupled with a coupling component that is separate from the tension member and that frictionally engages with the distal end of the tension member to fix the coupling component about the distal end of the tension member. The coupling component frictionally engages with the tension member without require a knot to be tied in the tension member and without require any other alteration of the tension member. The coupling component also frictionally engages with the distal end of the tension member so that no trimming or cutting of the tension member is required after the coupling component is secured to the tension member. At block 2930, the tension member is retracted through the channel of the spool component so that the coupling component engages with the channel and thereby prevents the tension member from being pulled through the spool component's channel.

As described herein, the coupling component includes a main body having at least one aperture. As such, coupling the distal end of the tension member with the coupling component includes inserting the distal end of the tension member through the aperture to frictionally engage the distal end of the tension member with the coupling component. In some embodiments, the main body includes at least two apertures. In such embodiments, the method may include inserting the distal end of the tension member through each aperture of the main body to frictionally engage the tension member with the coupling component. In other embodiments, the method may include inserting opposing ends of the tension member through one aperture so that the coupling component is fixedly secured to both ends of the tension member. The tension member may be retracted within the channel of the spool component so that the coupling component does not extend radially outward beyond an outer wall of a cylindrical body member of the spool component.

Figure 30:
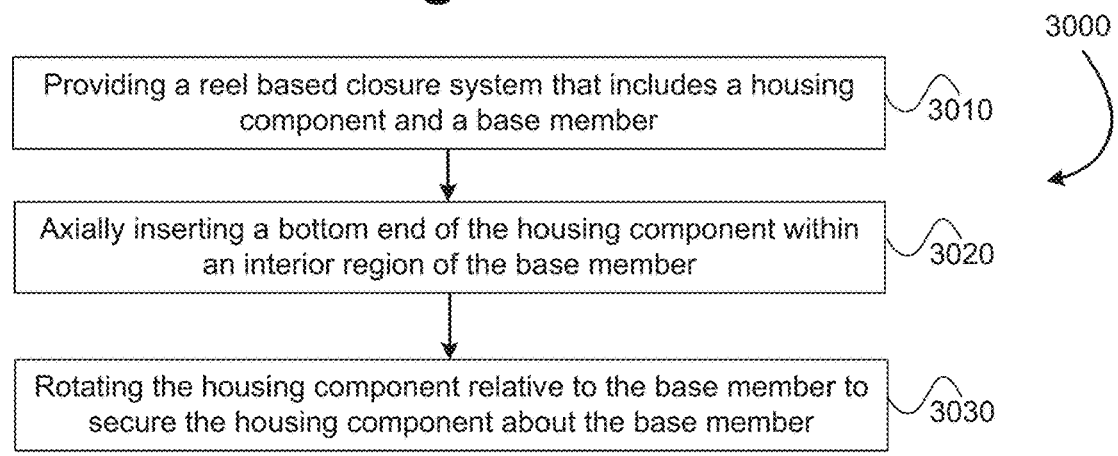
FIG. 30 illustrates a method of assembly of a reel based closure system.

Referring now to FIG. 30, illustrated is a method 3000 of assembly of a reel based closure system. At block 3010, a reel based closure system is provided. The reel based closure system includes a base member that defines an interior region, a housing component, a spool component rotatably positioned within the housing component, and a tightening component that is rotatably coupled with the housing component and that is operably coupled with the spool component to cause the spool component to rotate within the housing component upon an operation of the tightening component. At block 3020, a bottom end of the housing component is axially inserted within the interior region of the base member. At block 3030, the housing component is rotated relative to the base member to secure the housing component about the base member. After the housing component is secured to the base member, the housing component is detachable from the base component without requiring a counter rotation of the housing component relative to the base member.

The housing component may be detachable from the base component upon an application of a force to the housing component that causes the housing component to move axially out of the interior region of the base member. The axial movement of the housing component relative to the base member may require a deflection of at least a portion of the base member. The base member may include a pair of ports or channel and in such embodiments, the method may also include inserting a force application tool within each port or channel and applying a force to the housing component via the force application tool to cause the housing component to move axially relative to the base member. Axially inserting the bottom end of the housing component within the interior region of the base member may include inserting a plurality of radially extending tabs of the housing component within corresponding radially extending channels of the base member. In such embodiments, rotation of the housing component relative to the base member may cause each radially extending tab to be moved under a lip or protrusion of the base member.

The base member and the housing component may be configured so that the housing component must be aligned with the base member in one of a few defined orientations in order to couple the housing component with the base member. The base member and housing component may be configured to prevent rotation of the housing component relative to the base member when the housing component is axially inserted within the interior region of the base member in an orientation other than one of the few defined orientations.

Figure 31:
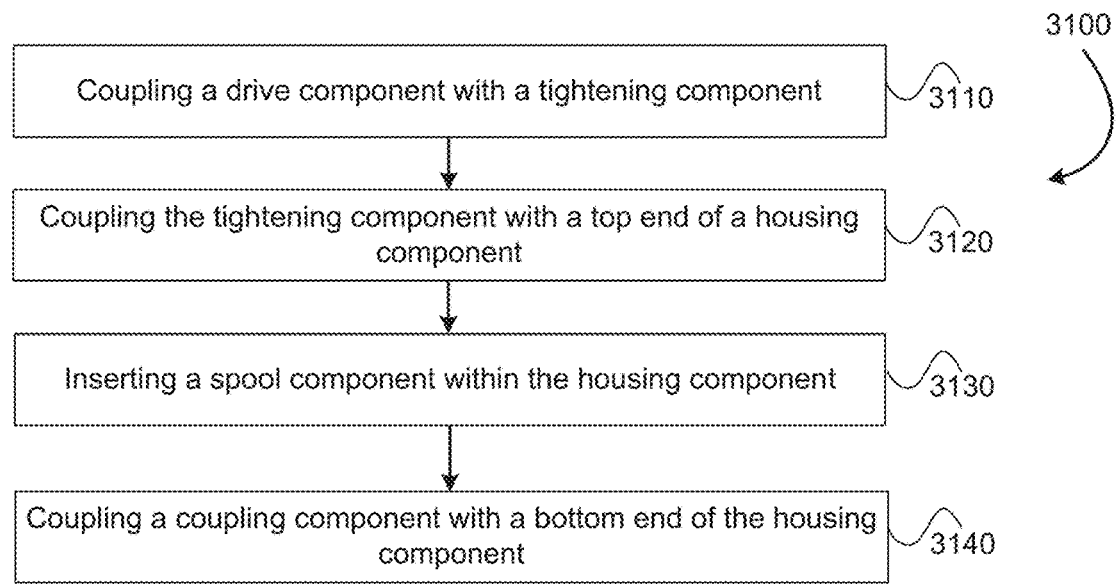
FIG. 31 illustrates a method of assembling a reel based closure device.

Referring now to FIG. 31, illustrated is a method 3100 of assembling a reel based closure device. At block 3110, a drive component is coupled with a tightening component. At block 3120, the tightening component is coupled with a top end of a housing component so that the drive component faces an interior region of the housing component. At block 3130, a spool component is inserted within the housing component so that a top end of the spool component faces a bottom surface of the drive component. At block 3140, a coupling component is coupled with a bottom end of the housing component so that a central boss of the coupling component extends into the interior region of the housing component. The coupling component includes a pair of arms that extend radially outward from the central boss and that attach to the bottom end of the housing component and a distal end of each arm includes a lip or tab that curves upward and detachably couples with the housing component when the pair of arms are attached to the bottom end of the housing component.

In some embodiments, the method may also include inserting the central boss through an aperture of the spool component and through an aperture of the drive component. In such embodiments, a top end of the central boss may include an annular projection that has a diameter that is greater than a diameter of the drive component's aperture. In some embodiments, inserting the spool component within the housing component includes inserting the spool component within the bottom end of the housing component. In some embodiments, the central boss may include an axially extending gap. In such embodiments, the method may also include inserting a reinforcement spring within the axially extending gap of the central boss. Coupling the tightening component with a top end of a housing component may include snapping a lip of the tightening component over a corresponding lip of the housing component.

While several embodiments and arrangements of various components are described herein, it should be understood that the various components and/or combination of components described in the various embodiments may be modified, rearranged, changed, adjusted, and the like. For example, the arrangement of components in any of the described embodiments may be adjusted or rearranged and/or the various described components may be employed in any of the embodiments in which they are not currently described or employed. As such, it should be realized that the various embodiments are not limited to the specific arrangement and/or component structures described herein.

In addition, it is to be understood that any workable combination of the features and elements disclosed herein is also considered to be disclosed. Additionally, any time a feature is not discussed with regard in an embodiment in this disclosure, a person of skill in the art is hereby put on notice that some embodiments of the invention may implicitly and specifically exclude such features, thereby providing support for negative claim limitations.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A reel based closure system comprising:
   a base member that defines an interior region;
   a housing component that is positionable within the interior region of the base member and that is releasably coupleable with the base member;
   a spool component rotatably positioned within the housing component, the spool component being configured so that a tension member is windable about the spool component;
   a tightening component rotatably coupled with the housing component and operably coupled with the spool component such that an operation of the tightening component causes the spool component to rotate within the housing component to wind the tension member about the spool component and thereby tighten an article;
   wherein the housing component is coupleable with the base member by axially inserting the housing component within the interior region of the base member and rotating the housing component relative to the base member; and
   wherein the housing component is detachable from the base member without requiring a rotation of the housing component relative to the base member.

2. The reel based closure system of claim 1, wherein the housing component is detachable from the base member upon application of a force to the housing component that causes the housing component to move axially out of the interior region of the base member.

3. The reel based closure system of claim 2, wherein the housing component is detachable from the base member via a deflection of at least a portion of the base member.

4. The reel based closure system of claim 2, wherein the base member includes one or more ports or channel within which a force application tool is positionable to apply the force to the housing component that causes the housing component to move axially out of the interior region of the base member.

5. The reel based closure system of claim 1, wherein:
   a bottom end of the housing component that is insertable within the interior region of the base member includes a plurality of radially extending tabs;
   the base member includes a plurality of radially extending channels that align with the radially extending tabs to enable the housing component to be axially inserted within the interior region of the base member; and
   rotation of the housing component relative to the base member causes each radially extending tab to be moved within a circumferential groove or channel and positioned under a lip or protrusion of the base member.

6. The reel based closure system of claim 5, wherein at least one of the radially extending tabs of the housing component is configured to mechanically engage with an anti-rotation member of the circumferential groove or channel of the base member to prevent a counter rotation of the housing component relative to the base member and thereby secure the housing component within the interior region of the base member.

7. The reel based closure system of claim 1, wherein the base member and the housing component are configured so that the housing component must be aligned with the base member in one of a few defined orientations in order to couple the housing component with the base member.

8. The reel based closure system of claim 7, wherein the base member and the housing component are configured to prevent rotation of the housing component relative to the base member when the housing component is axially inserted within the interior region of the base member in an orientation other than one of the few defined orientations.

9. A reel based closure system comprising:
a base member that defines an interior region;
a housing component that is positionable within the interior region of the base member and that is releasably coupleable with the base member;
a spool component rotatably positioned within the housing component, the spool component being configured so that a tension member is windable about the spool component;
a tightening component rotatably coupled with the housing component and operably coupled with the spool component such that an operation of the tightening component causes the spool component to rotate within the housing component to wind the tension member about the spool component;
wherein the housing component is rotatable relative to the base member to secure the housing component within the interior region of the base member; and
wherein the housing component is axially moveable relative to the base member to detach the housing component from the base member without requiring a rotation of the housing component relative to the base member.

10. The reel based closure system of claim 9, wherein the housing component is axially moveable relative to the base member upon application of a force to the housing component that would damage the housing component absent detachment of the housing component from the base member.

11. The reel based closure system of claim 9, wherein the housing component is axially moveable relative to the base member via a deflection of at least a portion of the base member.

12. The reel based closure system of claim 9, wherein the base member includes one or more ports or channel within which a force application tool is positionable to apply a force to the housing component that causes the housing component to move axially relative to the base member.

13. The reel based closure system of claim 9, wherein the base member and the housing component are configured to prevent rotation of the housing component relative to the base member unless the housing component is aligned with the base member in a defined orientation.

14. A method of assembly of a reel based closure system comprising:
providing a reel based closure system comprising:
a base member that defines an interior region;
a housing component;
a spool component rotatably positioned within the housing component; and
a tightening component rotatably coupled with the housing component and operably coupled with the spool component to cause the spool component to rotate within the housing component upon an operation of the tightening component;
axially inserting a bottom end of the housing component within the interior region of the base member; and
rotating the housing component relative to the base member to secure the housing component about the base member;
wherein the housing component is detachable from the base member without requiring a counter rotation of the housing component relative to the base member.

15. The method of claim 14, wherein the housing component is detachable from the base member upon application of a force to the housing component that causes the housing component to move axially out of the interior region of the base member.

16. The method of claim 15, wherein an axial movement of the housing component relative to the base member requires a deflection of at least a portion of the base member.

17. The method of claim 14, wherein the base member includes one or more ports or channel and wherein the method further comprises inserting a force application tool within the one or more ports or channels and applying a force to the housing component via the force application tool to cause the housing component to move axially relative to the base member.

18. The method of claim 14, wherein:
axially inserting the bottom end of the housing component within the interior region of the base member comprises inserting a plurality of radially extending tabs of the housing component within corresponding radially extending channels of the base member; and
rotation of the housing component relative to the base member causes each of the radially extending tabs to be moved under a lip or protrusion of the base member.

19. The method of claim 14, wherein the base member and the housing component are configured so that the housing component must be aligned with the base member in one of a few defined orientations in order to couple the housing component with the base member.

20. The method of claim 19, wherein the base member and the housing component are configured to prevent rotation of the housing component relative to the base member when the housing component is axially inserted within the interior region of the base member in an orientation other than one of the few defined orientations.

* * * * *